US007723045B2

(12) United States Patent
Fogelman et al.

(10) Patent No.: US 7,723,045 B2
(45) Date of Patent: May 25, 2010

(54) ASSAYS TO PREDICT ATHEROSCLEROSIS AND DYSFUNCTIONAL HIGH-DENSITY LIPOPROTEIN

(75) Inventors: Alan M. Fogelman, Beverly Hills, CA (US); Srinivasa T. Reddy, Cerritos, CA (US)

(73) Assignee: The Regents of the University of California, Oakland, CA (US)

( * ) Notice: Subject to any disclaimer, the term of this patent is extended or adjusted under 35 U.S.C. 154(b) by 165 days.

(21) Appl. No.: 11/672,897

(22) Filed: Feb. 8, 2007

(65) Prior Publication Data
US 2007/0218501 A1    Sep. 20, 2007

Related U.S. Application Data

(60) Provisional application No. 60/772,429, filed on Feb. 10, 2006, provisional application No. 60/843,213, filed on Sep. 7, 2006.

(51) Int. Cl.
G01N 33/53    (2006.01)

(52) U.S. Cl. .............. 435/7.1; 435/7.21; 435/7.92; 435/283.1; 435/325; 436/514; 436/518; 436/540; 424/130.1

(58) Field of Classification Search ................ None
See application file for complete search history.

(56) References Cited

U.S. PATENT DOCUMENTS

| | | | |
|---|---|---|---|
| 2003/0077668 A1 | 4/2003 | Uchida et al. |
| 2005/0181398 A1 | 8/2005 | Fung et al. |
| 2005/0244336 A1 | 11/2005 | Low et al. |
| 2008/0268478 A1 | 10/2008 | Sharifi et al. |

FOREIGN PATENT DOCUMENTS

WO    WO 2007/095126 A2    8/2007

OTHER PUBLICATIONS

Van Lanten et al. (Journal of Clinical Investigation, 1995, vol. 96, pp. 2758-2767).*
Miller et al. (Biochimica et Biohysica Acta vol. 1454, pp. 153-164, 1999).*
Navab et al. (Journal of Lipid Research, vol. 45, 2004, pp. 993-1007).*
Ansell et al., (2003) "Inflammatory/Antiinflammatory Properties of High-Density Lipoprotein Distinguish Patients From Control Subjects Better Than High-Density Lipoprotein Cholesterol Levels and Are Favorably Affected By Simvastatin Treatment", *Circulation* 108:2751-2756.
Aristoeli LP et al., (2006) "The monocytic lineage specific soluble CD163 is a plasma marker of coronary therosclerosis", *Atherosclerosis* 184:342-347.
Bakker et al., (2005) "Protease activity of plasma hemopexin", *Kidney International* 68:603-610.
Bakker et al., (2005) "Altered activity of plasma hemopexin in patients with minimal change disease in relapse", *Pediatr Nephrol* 20:1410-1415.
Bergt et al., (2004) "The myeloperoxidase product hypochlorous acid oxidizes HDL in the human artery wall and impairs ABCA1-dependent cholesterol transport", *PNAS USA* 101(35):13032-13037.
Brouwers et al., (2004) "Oxidized low-density lipoprotein, iron stores, and haptoglobin polymorphism", *Atherosclerosis* 176:189-195.
Castellani et al., (1997) "Overexpression of Apolipoprotein AII in Transgenic Mice Converts High Density Lipoproteins to Proinflammatory Particles", *J. Clin Invest.* 100(2):464-474.
Castelli et al., (1986) "Incidence of coronary heart disease and lipoprotein cholesterol levels", *The Framingham study JAMA* 256(20):2835-2838.
Cavallero et al., (1995) "Abnormal reverse cholesterol transport in controlled type II diabetic patients", *Arteriosclerosis Thrombosis and Vascular Biology* 15:2130-2135, http://atvb.ahajournals.org/cgi/content/full/15/12/1230.
Delanghe et al., (2002) "Discriminative value of serum amyloid A and other acute-phase proteins for coronary heart disease", *Atherosclerosis* 160:471-476.
Delanghe et al., (2002) "Haptoglobin Polymorphism and Body Iron Stores", *Clin Chem Lab Med* 40(3):212-216.
Downs et al., (1998) "Primary Prevention of Acute Coronary Events With Lovastatin in Men and Women With Average Cholesterol Levels: Results of AFCAPS/TexCAPS", *Air Force/Texas Coronary Atherosclerosis Prevention Study JAMA* 279(20):1615-1622.
Duan et al., (2005) "Immunodepletion of albumin for two-dimensional gel detection of new mouse acute-phase protein and other plasma proteins", *Proteomics* 5:3991-4000.
Fasano et al., (2004) "Nitrosylation of rabbit ferrous hemehemopexin", *J Biol Inorg Chem* 9:800-806.
Forte et al., (2002) "Altered activities of anti-atherogenic enzymes, LCAT, paraoxonase, and platelet-activating factor acetylhydrolase in atherosclerosis-susceptible mice", *Journal of Lipid Research* 43:477-485.
Gordon et al., (1977) "High density lipoprotein as a protective factor against coronary heart disease", *Am J Med* 62(5):707-714.
Gowri et al., (1999) "Decreased Protection by HDL From Poorly Controlled Type 2 Diabetic Subjects Against LDL Oxidation May Be Due to the Abnormal Composition of HDL", *Arteriosclerosis Thrombosis and Vascular Biology* 19:2226-2233.

(Continued)

*Primary Examiner*—Lisa V Cook
(74) *Attorney, Agent, or Firm*—Weaver Austin Villeneuve & Sampson LLP; Tom Hunter

(57) ABSTRACT

This invention provides novel assays for the detection of dysfunctional HDL. The assays are good diagnostics and/or prognostics for atherosclerosis or other pathologies characterized by an inflammatory response. In certain embodiments the methods involve measurements of heme-related HDL-associated proteins (e.g., haptoglobin, hemopexin, etc.), and/or measurements of the relative distribution of HDL-associated proteins between HDL and the non-lipoprotein fractions of plasma/serum, and/or measurements of the ability of proinflammatory HDL to consume nitric oxide, and/or measurement of the ability of HDL to inhibit LDL aggregation.

8 Claims, 31 Drawing Sheets

OTHER PUBLICATIONS

Hvidberg et al., (2005) "Identification of the receptor scavenging hemopexin-heme complexes", *Blood* 106(7):2572-2579.

Kap-Soon et al., (2004) "Protein biomarkers in the plasma of workers occupationally exposed to polycyclic aromatic hydrocarbons", *Proteomics* 4:3505-3513.

Kunitake et al., (1994) "Identification of Proteins Associated with Apolipoprotein A-I-Containing Lipoproteins Purified by Selected-Affinity Immunosorption", *Biochemistry* 33:1988-1993.

Kuzelova et al., (1997) "Kinetics of heme interaction with heme-binding proteins: the effect of heme aggregation state", *Biochim et Biophys Acta* 1336:497-501.

Mauk et al., (2005) "Metal Ion Binding to Human Hemopexin" *Biochemistry* 44:1864-1871.

McMahon et al., (2005) "Pro-inflammatory HDL as a biomarker for atherosclerosis in SLE and RA", *Arthritis and Rheumatism* 52(9)Suppl S:S697-S698.

Miller et al., (1999) "Kinetics of hemin distribution in plasma reveals its role in lipoprotein oxidation", *Biochim et Biophys Acta* 1454:153-164.

Navab et al., (1997) "Mildly Oxidized LDL Induces an Increased Apolipoprotein J/Paraoxonase Ratio"*J. Clin. Invest.* 99(8):2005-2019.

Navab et al., (2005) "The double jeopardy of HDL", *Annals of Medicine* 37(3):173-178.

Navab et al., (2004) "The oxidation hypothesis of atherogenesis: the role of oxidized phospholipids and HDL", *J Lipid Res* 45:993-1007.

Peng D-Q et al., (2005) "Tyrosine Modification is Not Required for Myeloperoxidase-Induced Loss of Apolipoprotein A-I Functional Activities", *The Journal of Biological Chemistry* 280(40):33775-33784.

Pennathur et al., (2004) "Human Atherosclerotic Intima and Blood of Patients with Established Coronary Artery Disease Contain High Density Lipoprotein Damaged by Reactive Nitrogen Species", *Journal of Biological Chemistry* 279(41):42977-42983.

Ridker, (2002) "On Evolutionary Biology, Inflammation, Infection, and the Causes of Atherosclerosis", *Circulation* 105:2-4.

Shipulina et al., (2000) "Heme Binding by Hemopexin: Evidence for Multiple Modes of Binding and Functional Implications", *J Protein Chem* 19(3):239-248.

Solar et al., (1989) "Serum proteins as mediators of hemin efflux from red cell membranes: specificity of hemopexin", *FEBS Lett* 256(1,2):225-229.

Spagnuolo et al., (2003) "The Binding of Haptoglobin to Apolipoprotein AI: Influence of Hemoglobin and Concanavalin A", *Biol Chem* 384:1593-1596.

Van Lenten et al., (1995) "Anti-Inflammatory HDL Becomes Pro-inflammatory during the Acute Phase Response. Loss of Protective Effect of HDL against LDL Oxidation in Aortic Wall Cell Cocultures", *Journal of Clinical Investigation* 96:2758-2767.

Van Lenten et al., (2001) "High-density Lipoprotein Loses Its Anti-Inflammatory Properties During Acute Influenza A Infection", *Circulation* 103:2283-2288.

Vlierberghe et al., (2004) "Haptoglobin polymorphisms and iron homeostasis in health and in disease", *Clinica Chimica Acta* 345:35-42.

Wait et al., (2005) "Reference maps of mouse serum acute-phase proteins: Changes with LPS-induced inflammation and apolipoprotein A-I and A-II transgenes", *Proteomics* 5:4245-4253.

Watson et al., (2004) "Metabolic syndrome patients have higher plasma lipid hydroperoxidase and control more pro-inflammatory HDL than dyslipidemic control subjects, even with comparable levels of HDL, hs-CRP and paraoxonase activity", *Circulation* 110(17)Suppl S:52.

Zheng et al., (2004) "Apolipoprotein A-I is a selective target for myeloperoxidase-catalyzed oxidation and functional impairment in subjects with cardiovascular disease", *Journal of Clinical Investigation* 114(4):529-541.

Zheng et al., (2005) "Localization of Nitration and Chlorination Sites on Apolipoprotein A-I Catalyzed by Myeloperoxidase in Human Atheroma and Associated Oxidative Impairment in ABCA1-dependent Cholesterol Efflux from Macrophages", *Journal of Biological Chemistry* 280(1):38-47.

International Search Report dated Oct. 15, 2008 issued in PCT/US07/03588.

International Preliminary Report on Patentability and Written Opinion dated Oct. 15, 2008 issued in PCT/US07/03588.

EP Extended European Search Report dated Aug. 19, 2009 issued in EP 07 75 0425.6-2404.

Fogelman AM, (2004) "When good cholesterol goes bad", *Nat Med*, 10(9):902-903.

Navab et al., (2001) "A cell-free assay for detecting HDL that is dysfunctional in preventing the formation of or inactivating oxidized phospholipids", *Journal Lipid Res*, 42(8):1308-1317.

Nicholls et al., (2005) "Formation of Dysfunctional High-Density Lipoprotein by Myeloperoxidase", *Trends in Cardiovascular Medicine Elsevier Science*, 15(6):212-219.

\* cited by examiner

ASSAYS TO PREDICT ATHEROSCLEROSIS AND DYSFUNCTIONAL HIGH-DENSITY LIPOPROTEIN

CROSS-REFERENCE TO RELATED APPLICATIONS

This application claims benefit of and priority to U.S. Ser. No. 60/843,213, filed on Sep. 7, 2006, and U.S. Ser. No. 60/772,429, filed on Feb. 10, 2006, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support of Grant Nos. HL71776 and HL30568 awarded by the National Institutes of Health. The Government has certain rights in this invention.

FIELD OF THE INVENTION

This invention relates to the diagnosis of atherosclerosis. In particular this invention provides improved assays for the detection of dysfunctional HDL.

BACKGROUND OF THE INVENTION

Atherosclerosis, a chronic inflammatory disease of large and medium sized arteries, is the leading cause of morbidity and mortality in Western countries. Introduction of statins has resulted in a one-third reduction in mortality. Two-thirds of the mortality due to this disease, however, continues despite statin treatment.

Oxidation of low-density lipoproteins (LDL) is a major factor in human atherosclerosis (Witztum and Steinberg (2001) *Trends Cardiovasc. Med.*, 11: 93-102; Witztum and Steinberg (1991) *J. Clin. Invest.*, 88: 1785-1792). Entrapment and oxidation of LDL in the sub-endothelial space, and the subsequent interactions between endothelial cells and monocytes, is a key process in the initiation of atherosclerotic lesion development (Navab et al. (1996) *Arterioscler. Thromb. Vasc. Biol.*, 16: 831-842; Berliner et al. (1995) *Circulation* 91: 2488-2496). Minimally modified/oxidized-LDL (MM-LDL) contains biologically active molecules that are capable of inducing endothelial cells to produce inflammatory agents, such as chemokines, adhesion molecules, and growth factors. These inflammatory molecules promote the recruitment and adhesion of monocytes to the endothelial cells Berliner et al. (1995) *Circulation* 91: 2488-2496). Several biologically active oxidized phospholipids have been identified in MM-LDL and in atherosclerotic lesions of animal models (Watson et al. (1995) *J. Clin. Invest.*, 95: 774-782; Watson et al. (1995) *J. Clin. Invest.*, 96: 2882-2891; Watson et al. (1997) *J. Biol. Chem.*, 272: 13597-13607; Watson et al. (1999) *J. Biol. Chem.*, 274: 24787-24798; Leitinger et al. (1999) *Arterioscler. Thromb. Vasc. Biol.*, 19: 1291-1298; Subbanagounder et al. (2000) *Free Radic. Biol. Med.*, 28: 1751-1761). Oxidized-L-α-1-palmitoyl-2-arachidonyl-sn-glycero-3-phosphocholine (ox-PAPC) and three of its components, 1-palmitoyl-2-(5-oxovaleroyl)-sn-glycero-3-phosphocholine (POVPC), 1-palmitoyl-2-glutaroyl-sn-glycero-3-phosphocholine (PGPC) and 1-palmitoyl-2-(5,6-epoxyisoprostane $E_2$)-sn-glycero-3-phosphocholine (PEIPC) (Watson et al. (1999) *J. Biol. Chem.*, 274: 24787-24798; Leitinger et al. (1999) *Proc. Natl. Acad. Sci. U.S.A.* (1999) 96:12010-12015; Subbanagounder et al. (2000) *Arterioscler. Thromb. Vasc. Biol.*, 20: 2248-2254), induce monocyte binding to endothelial cells and play a major role in the activation of endothelial cells by MM-LDL. Subsequent to the discovery of these molecules, a series of other oxidized phospholipids formed by the oxidation of an unsaturated fatty acid at the sn-2 position of the phospholipid have been identified with similar biologic activities (Berliner and Watson (2005) *N. Engl. J. Med.*, 353: 9-11).

The inverse relationship between HDL and the risk of atherosclerosis is well established. Although there does not appear to be a single explanation for the anti-atherogenic role of HDL, it has become clear that the functional status of HDL, which is largely dependent on its protein components, is an important determinant of coronary heart disease (CHD) (Navab et al. (2001) *Arterioscler. Thromb. Vasc. Biol.*, 21: 481-488). Paraoxonase 1 (PON1), lecithin-cholesterol acyltransferase (LCAT), platelet-activating factor acetyl hydrolase (PAF-AH), proteinase (elastase-like), phospholipase D, albumin, apoJ and apoA-I are proteins in HDL with anti-atherogenic properties capable of preventing MM-LDL formation. HDL has been shown to have a role in preventing LDL oxidation. HDL was shown to inhibit the mild oxidation of LDL and consequently inhibit the production of the potent monocyte chemoattractant MCP-1 by human artery wall cells.

HDL can exist as an anti-inflammatory molecule or a pro-inflammatory molecule depending on the context and environment. The acute phase reaction (APR) in rabbits and humans can convert HDL from an anti-inflammatory to a pro-inflammatory form, i.e. HDL looses its ability to protect against LDL-induced inflammation and in its pro-inflammatory state HDL actually promotes LDL-induced inflammation. Without being bound to a particular theory, it is believed that, under basal conditions, HDL serves an anti-inflammatory role but during APR there is loss of anti-oxidant enzyme activities, damage to apoA-I, and displacement and/or exchange of proteins associated with HDL resulting in a pro-inflammatory HDL. It has been shown, for example, that an atherogenic diet in mice that are genetically susceptible to atherosclerosis (but not in mice genetically resistant to atherosclerosis) converts HDL from anti-inflammatory to pro-inflammatory (Navab et al. (1997) *J. Clin. Invest.*, 99: 2005-2019). Several studies have since shown the presence and nature of pro-inflammatory HDL in animal models (Castellani et al. (1997) *J. Clin. Invest.*, 100: 464-474, reviewed in Navab et al. (2005) *Ann. Med.*, 37: 173-178).

HDL from C57BL/6J mice (a strain that is genetically susceptible to dietary-induced atherosclerosis) was anti-inflammatory in mice on a chow diet but was pro-inflammatory when the mice were on an atherogenic diet (Shih et al. (1996) *J. Clin. Invest.*, 97: 1630-1639). In contrast, the HDL from atherosclerosis-resistant C3H/HeJ (C3H) mice was anti-inflammatory whether the mice were on a chow or atherogenic diet (Id.). All of the mouse models studied to date that develop atherosclerosis with macrophage-rich lesions have pro-inflammatory HDL. These include C57BL/6J mice on an atherogenic diet (Id.), transgenic mice that overexpress apoA-II on a chow diet (Castellani et al. (1997) *J. Clin. Invest.*, 100: 464-474), PON1 null mice fed an atherogenic diet (Id.), apoE null mice (Navab et al. (1997) *J. Clin. Invest.*, 99: 2005-2019), combined apoE null and PON1 null mice on a chow diet (Castellani et al. (1997) *J. Clin. Invest.*, 100: 464-474), LDL receptor (LDLR) null mice fed a high-fat diet (Navab et al. (1997) *J. Clin. Invest.*, 99: 2005-2019), and transgenic mice that overexpress $sPLA_2$ (Leitinger et al. (1999) *Arterioscler. Thromb. Vasc. Biol.*, 19: 1291-1298). In genetically distinct mouse models, all of which were hyperlipidemic, but none of which developed atherosclerosis HDL was found to be anti-inflammatory (Navab et al. (2005) *Ann. Med.,* 37: 173-178). On the other hand, seven other mouse models all of which developed atherosclerosis characterized by macrophage-rich lesions had pro-inflammatory HDL (Id.), suggesting that the anti- or pro-inflammatory nature of HDL function is a more sensitive indicator of the presence or absence of atherosclerosis than HDL cholesterol levels. The quality and function of HDL has become an attractive target for emerging new therapies (Castellani et al. (1997) *J. Clin. Invest.,* 100: 464-474; Navab et al. (2005) *Ann. Med.,* 37: 173-178; Ridker (2002) *Circulation,* 105: 2-4; Ansell et al. (2003) *Circulation,* 108: 2751-2756).

Although a number of proteins and enzyme activities have been associated with HDL, little is known of what particular protein profiles are associated with pro-inflammatory HDL.

SUMMARY OF THE INVENTION

Determining the quality and function of HDL is critical to improving the detection of persons at risk for atherosclerotic events and for targeting new and novel therapies. The current tests for dysfunctional HDL measure various parameters and components of HDL and are relatively cumbersome and expensive.

This invention provides simple new assays for predicting dysfunctional HDL.

In certain embodiments this invention pertains to the identification of protein profiles that distinguish pro-inflammatory HDL from normal/anti-inflammatory HDL. This provides biomarkers for the early detection of the presence and/or predisposition to atherosclerosis, other pathologies characterized by an inflammatory response, and thus provide new strategies for therapeutic intervention.

In various embodiments the assays include measurements of heme-related HDL-associated proteins (e.g., haptoglobin, hemopexin, etc.), and/or measurements of the relative distribution of HDL-associated proteins between HDL and the non-lipoprotein fractions of plasma/serum, and/or measurements of the ability of pro-inflammatory HDL to consume nitric oxide, and/or measurement of the ability of HDL to inhibit LDL aggregation.

In certain embodiments this invention provides a method of detecting or quantifying pro-inflammatory HDL in a mammal. The method typically involves providing a biological sample from the mammal, where the sample comprising HDL; and detecting two or more proteins, three or more, or four or more, or five or more, six or more, seven or more or eight different proteins associated with HDL, where the proteins are selected from the group consisting of a protein having an m/z ratio of about 9.3, a protein having an m/z ratio of about 14.9, a protein having an m/z ratio of about 15.6, a protein having an m/z ratio of about 15.8, a protein having an m/z ratio of about 16.2, a protein having an m/z ratio of about 16.5, a protein having an m/z ratio of about 18.6, and a protein having an m/z ratio of about 19.5, where the detection of the two or more proteins in association with HDL indicates that the HDL is a pro-inflammatory HDL. In certain embodiments the mammal is a non-human mammal or a human (e.g., a human diagnosed as having atherosclerosis, or at risk for atherosclerosis, or as having another pathology characterized by an inflammatory response, or at risk for such a pathology).

In certain embodiments methods are provided for detecting or quantifying pro-inflammatory HDL in a mammal. The method typically involves measuring the level of heme-containing and/or heme-binding protein(s) associated with HDL from the mammal where an elevated level of heme-containing and/or heme-binding protein(s) as compared to the level of heme-containing and/or heme-binding protein found in normal anti-inflammatory HDL indicates that the HDL is pro-inflammatory HDL. In certain embodiments the heme-containing and/or heme-binding proteins comprise one or more proteins selected from the group consisting of hemoglobin, haptoglobin, hemopexin, transferrin, soluble CD163, and myeloperoxidase. In certain embodiments the method involves measuring the amount of hemoglobin associated with HDL and measuring the amount of haptoglobin associated with HDL. In certain embodiments the method comprises calculating the product of hemoglobin and haptoglobin associated with HDL. In certain embodiments the method involves measuring the level of the same heme-containing and/or heme-binding proteins in the non-lipoprotein fraction of plasma where an increased ratio of heme-containing and/or heme-binding protein in HDL to heme-containing and/or heme-binding protein in the non-lipoprotein fraction of plasma as compared to the ratio found in subjects having normal anti-inflammatory HDL indicates that the HDL from the mammal is pro-inflammatory HDL.

Also provided are methods of detecting or quantifying pro-inflammatory HDL in a mammal. In various embodiments, the methods involve measuring the level of one or more heme-containing and/or heme-binding protein(s) associated with HDL from the mammal; measuring the level of one or more of the same heme-containing and/or heme-binding protein(s) in the plasma (or serum) from the mammal, where a ratio of HDL heme-containing and/or heme-binding protein to plasma heme-containing and/or heme-binding protein greater than 1 indicates that the HDL from the mammal is pro-inflammatory HDL. In certain embodiments the heme-containing and/or heme-binding protein comprises one or more proteins selected from the group consisting of hemoglobin, haptoglobin, hemopexin, transferrin, soluble CD163, and myeloperoxidase. In certain embodiments heme-containing and/or heme-binding protein comprises haptoglobin and hemopexin. In certain embodiments a ratio of HDL heme-containing and/or heme-binding protein to plasma heme-containing and/or heme-binding protein greater than 1 for two or more, three or more, four or more, five or more or six of the proteins indicates that the HDL from the mammal is pro-inflammatory HDL. In certain embodiments a ratio of HDL heme-containing and/or heme-binding protein to plasma heme-containing and/or heme-binding protein for one, two, three, four, five, or six of the proteins greater than a value selected from the group consisting of 1, 0.9, 0.8, 0.7, 0.6, 0.5, 0.4, 0.3, and 0.2, indicates that the HDL from the mammal is pro-inflammatory HDL.

Also provided are methods of method of detecting or quantifying pro-inflammatory HDL in a mammal. The methods typically involve determining the level of heme associated with HDL from the mammal, where an elevated level of heme associated with HDL as compared to the level of heme associated with protective HDL indicates that the HDL is pro-inflammatory HDL. In certain embodiments the elevated level is statistically significant at a confidence level equal to or greater than the 90%, 95%, 98% or 99%.

In certain embodiments methods are provided for detecting or quantifying pro-inflammatory HDL in a mammal, where the methods typically involve: determining the iron content of HDL from the mammal, where an elevated level of iron content of the HDL as compared to the iron content of normal anti-inflammatory HDL indicates that the HDL from the mammal is pro-inflammatory HDL. In certain embodiments the elevated level is statistically significant at a confidence level equal to or greater than the 90%, 95%, 98% or 99%.

In various embodiments, methods are provided for detecting or quantifying pro-inflammatory HDL in a mammal. The methods typically involve determining the level of iron-containing proteins associated with HDL from the mammal, where an elevated level of iron-containing proteins associated with the HDL as compared to the level of iron-containing proteins associated with normal anti-inflammatory HDL indicates that the HDL from the mammal is pro-inflammatory HDL. In certain embodiments the elevated level is statistically significant at a confidence level equal to or greater than the 90%, 95%, 98% or 99%.

Methods are also provided for using a nitric oxide assay to detect or quantify pro-inflammatory HDL. The methods typically involve the ability of the HDL to consume nitric oxide where in increased ability of the HDL to consume nitric oxide as compared to the ability of normal anti-inflammatory HLD to consume nitric oxide indicates the presence, quantity, or activity of pro-inflammatory HDL. In certain embodiments the nitric oxide is generated chemically. In certain embodiments the nitric oxide is measured by an electronic signal.

Aggregation assays are also provided for detecting or quantifying pro-inflammatory HDL in a mammal. These assays typically involve contacting HDL from the mammal with LDL and measuring the aggregation of the LDL, where elevated level of LDL aggregation as compared to the aggregation of LDL contacted with normal anti-inflammatory HDL indicates that the HDL from the mammal is pro-inflammatory HDL. In certain embodiments the aggregation is determined by spectrophotometrically measuring the LDL aggregation rate. In certain embodiments the aggregation is determined using an albumin depletion column.

In certain embodiments methods are provided for assaying for the presence or predisposition to a pathology characterized by an inflammatory response in a mammal. The method typically involves performing any one or more of the assays described herein, where a positive test result is an indicator for the presence or predisposition to the pathology. In various embodiments, the pathology is selected from the group consisting of atherosclerosis, stroke, leprosy, tuberculosis, systemic lupus erythematosus, polymyalgia rheumatica, polyarteritis nodosa, scleroderma, idiopathic pulmonary fibrosis, chronic obstructive pulmonary disease, asthma, Alzheimer's Disease, chronic renal failure, diabetes, diabetic retinopathy, diabetic renal disease, transplant rejection, transplant atherosclerosis, reperfusion ischemia, adult respiratory syndrome, congestive heart failure, glomerulitis, metabolic syndrome, multiple sclerosis, sepsis syndrome, sickle cell disease, vascular dementia, Chron's Disease, endothelial dysfunction, arteriole dysfunction, AIDS, polymyalgia rheumatica, polyarteritis nodosa, scleroderma, idiopathic pulmonary fibrosis, coronary calcification, calcific aortic stenosis, osteoporosis, a bacterial infection, a viral infection, a fungal infection, an autoimmune disorder, and rheumatoid arthritis.

In certain embodiments the assays described herein are performed on a sample from a non-human mammal or a human (e.g., a human diagnosed as having atherosclerosis, or at risk for atherosclerosis, or as having another pathology characterized by an inflammatory responses, or at risk for such a pathology).

In certain embodiments, the proteins detected and/or quantified in the assays described herein are detected and/or quantified using an immunoassay (e.g., an ELISA).

Methods are also provided for treating a human or non-human mammal having a pathology characterized by an inflammatory response. The methods typically involve performing any one or more of the assays described herein, and prescribing a more aggressive therapy (e.g., administration of a statin, and/or therapeutic agent as described in U.S. Pat. Nos. 7,166,578, 7,148,197, 7,144,862, 6,933,279, 6,930,085, and 6,664,230, which are incorporated herein by reference for all purposes) for those subjects that test positive in the assays.

DEFINITIONS

The following abbreviations may be used herein: APR, acute phase reaction; CAD, coronary artery disease; HDL-C, HDL cholesterol; MM-LDL, minimally modified/oxidized-LDL; PON, paraoxonase; ApoA1, apolipoprotein A1; apoE, apolipoprotein E; CM10, weak cation chip; CVD, cardiovascular diseases; CHD, coronary heart diseases; FPLC, fast protein liquid chromatography; Hb, hemoglobin; Hb-alpha, hemoglobin alpha chain; Hb-beta, hemoglobin beta chain; Hp, haptoglobin; Hx, hemopexin; HDL, High-density lipoprotein; HPLC, high performance liquid chromatography; LDL, low-density lipoprotein; LDLR, LDL receptor; metHb, methemoglobin; NP20 chip, normal phase chip; oxy Hb, oxyhemoglobin; PON, paraoxonase; pHDL, post HDL fraction; Q10 chip, strong anion-exchange chip; RBC, red blood cells; SELDI, surface-enhanced laser desorption/ionization; SELDI-TOF-MS, surface-enhanced laser desorption/ionization time-of-flight mass spectrometry; µLC-MSMS, micro-liquid chromatography with tandem mass spectrometry; VLDL, very low-density lipoprotein.

An "immunoassay" is an assay that utilizes an antibody to specifically bind an analyte (e.g., haptoglobin and/or hemopexin). The immunoassay is characterized by the use of specific binding properties of a particular antibody to isolate, target, and/or quantify the analyte.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" or "protective HDL" or "normal anti-inflammatory HDL" refers to a high density lipoprotein or components thereof (e.g. apo A-I, paraoxonase, platelet activating factor acetylhydrolase, etc.) that reduce oxidized lipids (e.g. in low density lipoproteins) or that protect lipids from oxidation by oxidizing agents.

The term "dysfunctional HDL" refers to an HDL that offers reduced activity or no activity in protecting lipids from oxidation or in repairing (e.g., reducing) oxidized lipids and is not able or is substantially unable to prevent the inflammatory consequences of these oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g., apo A-I, paraoxonase, platelet activating factor acetylhydrolase, etc.) that display such activity.

"Hemopexin" or "haptoglobin" refer to full length native hemopexin or haptoglobin, respectively, or to surrogate markers for hemopexin or haptoglobin such as hemopexin or haptoglobin fragments, isozymes, and the like, where detection/quantitation of the marker provides a measure of the amount/concentration of the full length molecule.

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, Fundamental Immunology, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies, those synthesized de novo using recombinant DNA methodologies (e.g., single chain Fv), and those found in display libraries (e.g. phage display libraries).

The phrase "normal healthy control" refers to an individual or population of individuals of approximately the same age and the same sex that do not exhibit symptoms or that test negative for the condition/pathology in question.

The phrase "detecting the levels of haptoglobin and/or hemopexin and/or other protein in blood or a blood fraction" refers to the detection and/or quantitation of haptoglobin and/or hemopexin and/or other protein in blood, a blood fraction or a sample derived from blood or a blood fraction. The detection can involve direct detection of intact haptoglobin and/or hemopexin, and/or other protein and/or detection of haptoglobin and/or hemopexin and/or other protein fragments, detection of isoforms and/or detection of various other surrogate markers for the protein(s) of interest.

The phrase "providing a biological sample from a mammal" means directly taking the sample (e.g., a blood sample) or obtaining or providing a biological sample that has been taken from the mammal by another party.

BRIEF DESCRIPTION OF THE DRAWINGS

As shown in FIG. 2 the HDL was pro-inflammatory prior to treatment. As shown in FIG. 17, prior to treatment this apoE null HDL failed to inhibit PLC-induced LDL aggregation. However, after 21 days of treatment the HDL became anti-inflammatory (FIG. 2) and as shown in FIG. 17 it significantly inhibited PLC-induced LDL aggregation. The values for the positive control (LDL+PLC No HDL) are shown as are the values for the negative controls i) LDL+PLC together with HDL from normal C57BL/6J mice on a chow diet (Normal Mouse HDL) and ii) LDL without PLC (LDL alone).

FIG. 22A: Serum samples (n=8) from C57BL/6J mice on either a normal chow (C) or atherogenic diet (A) for 7 days (D7) or 15 weeks (W15); FIG. 22B: VLDL, LDL, HDL and post HDL (pHDL) FPLC fractions from pooled serum samples of D7 and W15 groups. FIG. 22C: Individual FPLC fractions covering the region of HDL and pHDL (fractions 25-40) from D7-C and D7-A serum samples were analyzed for cholesterol (OD 490) and Heme (OD 410). FIG. 22A demonstrates that there was no significant difference in the amount of total non-RBC hemoglobin in mice fed the chow or the atherogenic diets for 7 or 15 days. The figure also shows that on an SDS PAGE gel the molecular weights of the non-RBC hemoglobin and hemoglobin from lysed RBC were similar. FIG. 22B shows that feeding the atherogenic diet for 7 days or for 15 weeks caused a shift in the non-RBC hemoglobin from the non-lipoprotein fractions (pHDL) to the HDL fractions. FIG. 22C confirms the data in FIG. 24B showing that after 7 days on chow there was almost no hemoglobin associated with HDL while after 7 days on the atherogenic diet there was substantial hemoglobin in the HDL fractions.

FIG. 23A: Pooled serum samples from C57BL/6J mice (n=8) fed either a normal chow (C) or atherogenic diet (A) was fractionated by FPLC and subjected to SELDI analysis with normal phase (NP20) or anion exchange (Q10; pI<7) ProteinChip arrays. Relative intensity at 14.9 k (Hb-alpha) and at 15.6 k (Hb-beta) is shown. FIG. 23B: Anion exchange column fractions representing pH7.0 and pH4.0 described under FIG. 2 were loaded on 15% SDS-PAGE and immunoblotted for hemoglobin. The altered properties of the non-RBC hemoglobin on the atherogenic diet as determined in these systems are consistent with the association of the hemoglobin with HDL and with other HDL proteins.

FIG. 28A shows the non-RBC hemoglobin in micrograms HRP/mL. FIG. 28B shows haptoglobin in micrograms HRP/mL. FIG. 28C shows the product of the non-RBC hemoglobin values multiplied by the haptoglobin values. The results indicate that the obtained values for the latter method separated the healthy volunteers from the diabetics and the CHD patients without any overlap.

DETAILED DESCRIPTION

Figure 1:
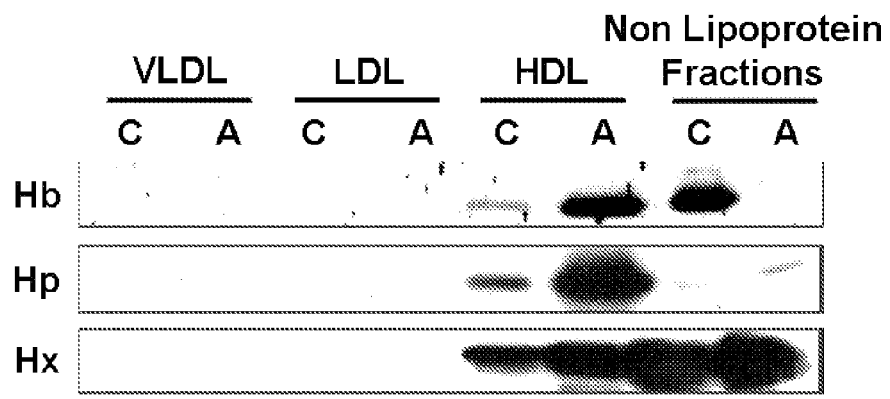
FIG. 1 shows a western analysis of HDL associated proteins. The Western analysis demonstrated a greater than 10-fold increase in the association of HDL with hemoglobin (Hb), haptoglobin (Hp), and hemopexin (Hx) in C57BL/6J mice fed an atherogenic diet (A) compared to a chow diet (C). As shown in the Figure these proteins did not associate with VLDL or LDL.

This invention pertains to novel assays for dysfunctional high-density lipoprotein (HDL). Dysfunctional HDL (e.g., pro-inflammatory HDL) has been implicated in the etiology of heart disease and in other pathological conditions characterized by an inflammatory response. Assays for dysfunctional HDL thus have diagnostic and prognostic value for the detection and/or prognosis of atherosclerosis and/or other conditions characterized by an inflammatory response (e.g., rheumatoid arthritis, lupus erythematous, polyarteritis nodosa, osteoporosis, atherosclerosis, stroke, leprosy, tuberculosis, systemic lupus erythematosus, polymyalgia rheumatica, polyarteritis nodosa, scleroderma, idiopathic pulmonary fibrosis, chronic obstructive pulmonary disease, asthma, Alzheimer's Disease, chronic renal failure, diabetes, diabetic retinopathy, diabetic renal disease, transplant rejection, transplant atherosclerosis, reperfusion ischemia, adult respiratory syndrome, congestive heart failure, glomerulitis, metabolic syndrome, multiple sclerosis, sepsis syndrome, sickle cell disease, vascular dementia, Chron's Disease, endothelial dysfunction, arteriole dysfunction, AIDS, polymyalgia rheumatica, polyarteritis nodosa, scleroderma, idiopathic pulmonary fibrosis, coronary calcification, calcific aortic stenosis, osteoporosis, a bacterial infection, fungal infection, an autoimmune disorder, and rheumatoid arthritis, congestive heart failure, endothelial dysfunction, arteriole dysfunction, viral illnesses, multiple sclerosis, and the like).

Increasing evidence suggests that HDL-inflammatory/anti-inflammatory properties are important determinants of the role of HDL in diseases such as atherosclerosis and are independent of HDL-cholesterol levels. This invention pertains to novel assays to measure the inflammatory properties of HDL. The assays described herein, can typically be grouped into two main categories:

I. Measurements of HDL-associated proteins, which reflect the inflammatory nature of HDL; and II. Measurements of the ability of HDL to inhibit the aggregation of LDL.

I. Measurements of HDL-Associated Proteins, which Reflect the Inflammatory Nature of HDL A) Eight Proteins Associated with HDL in Mouse Models of Atherosclerosis/Hyperlipidemia.

We have previously reported that the inflammatory properties of HDL are a more sensitive indicator of coronary heart disease (CHD) than HDL-cholesterol levels, in both mice and humans. In certain embodiments, this invention pertains, in part, to the identification of specific protein fingerprints that distinguish Group I/protective HDL from "dysfunctional" HDL. While illustrated in Examples 2 and 3 with respect to mouse HDL, it is believed that the same proteins/protein fingerprints and physiological mechanisms operate in human as well as other mammals. In particular, specific protein fingerprints that distinguish normal mouse HDL from mouse HDL on atherogenic diets, were identified ProteinChip technology coupled with surface-enhanced laser desorption/ionization time-of-flight mass spectrometry (SELDI-TOF-MS). Feeding C57BL/6J mice an atherogenic diet for one week resulted in lower HDL-cholesterol levels, reduced paraoxonase activity, increased reactive oxygen species content and reduced ability of the HDL to promote cholesterol efflux from macrophages. When the mice were switched back to a chow diet for an additional 2 weeks, the pro-atherogenic characteristics of HDL reverted to the normal phenotype (see, e.g., FIG. 19). We identified a total of 88 SELDI peaks with p<0.05 to be differentially present in pro-inflammatory HDL from mice fed an atherogenic diet compared to normal HDL from mice fed a chow diet. 74 of the 88 serum peaks reverted to normal levels upon diet reversal. Following further analyses to eliminate artifacts/changes arising from short-term dietary changes and non-atherogenic factors, we identified 24 SELDI m/z peaks representing proteins that are differentially associated with pro-inflammatory HDL. Fourteen of the 24 protein peaks were found common to pro-inflammatory HDL from three other widely used animal models of atherosclerosis/hyperlipidemia; C57BL/6J on western diet, LDLR null and apoE null mice. Furthermore, protein profiling of serum samples from all four animal models identified an eight-protein core signature (a subset of the 14 SELDI m/z peaks described above) that can be used as a serum biomarker panel for identifying pro-inflammatory HDL in mice and similar signatures can be used in humans and other mammals. These eight core signature proteins are described in detail in Example 2.

This protein signature can readily be detected (e.g., using mass spectrophotometric methods and/or protein chip methods as described herein) and thereby used to identify pro-inflammatory HDL, e.g. in a patient. The existence or magnitude of the protein signature can thus be used as a diagnostic and/or prognostic for atherosclerosis and/or other conditions characterized by an inflammatory response.

In certain instances one or more of the proteins can be detected using other standard methods including, but not limited to electrophoresis, chromatography, and/or immunoassays, to provide a rapid detection/quantification method for identifying or quantifying the strength of the protein signature in a patient.

B) The Surprising Finding that Non-RBC Hemoglobin is Associated with HDL in Mouse Models of Atherosclerosis/Hyperlipidemia.

As noted above we identified eight specific proteins using strong anion exchange SELDI ProteinChip technology that can be used individually, or in combination to distinguish normal/anti-inflammatory HDL from pro-inflammatory HDL. Two of the biomarker peaks (m/z 14,900 and m/z 15,600) most dramatically associated with pro-inflammatory HDL in the mouse models were further characterized. Using micro-liquid chromatography-tandem mass spectrometry, we identified the SELDI peaks representing m/z 14,900 and m/z 15,600, as mouse hemoglobin alpha chain (Hb-Alpha, 14.9 kDa) anld mouse hemoglobin beta chain (Hb-beta, 15.9 kDa), respectively. Western blot analysis confirmed the differential association of Hb with pro-inflammatory HDL when compared to normal HDL. Biochemical characterization of Hb associated with HDL further showed that the Hb associated with pro-inflammatory HDL possess distinct physical and chemical properties including reduced pI (pI 4.0 & pI 7.0 vs. pI 7.5 or higher for free Hb), and association with high molecular weight complexes found in fractions containing HDL.

Extensive analysis of this non-RBC hemoglobin revealed that the amino acid sequence was not different from RBC hemoglobin. Indeed, the altered physical properties of the non-RBC hemoglobin associated with pro-inflammatory HDL appears to be due to the tight association of this hemoglobin with other proteins that are associated with HDL such as haptoglobin.

It was a surprising finding of this invention that in mice and humans there are always small amounts of non-RBC hemoglobin present in plasma and serum. The concentration of this non-RBC hemoglobin is on the order of 10 micromolar. In contrast the concentration of hemoglobin in whole blood is greater than 1 molar. Therefore only about 0.001% of the hemoglobin in whole blood is outside of the RBC.

It was also a surprising discovery of this invention that in normal mice and in normal humans this small amount of non-RBC hemoglobin is located in the non-lipoprotein fractions of plasma or serum. It was also a surprising discovery of this invention that in mice on an atherogenic diet, or in mice that have been genetically manipulated to develop atherosclerosis, or in humans with diabetes or CHD, or in humans with other causes of pro-inflammatory HDL this non-RBC hemoglobin is found in HDL.

The main form of hemoglobin found associated with HDL was oxyhemoglobin (oxyHb). Based on the pro-oxidant nature of oxyHb, our data suggest that Hb may contribute to the pro-inflammatory nature of HDL under atherogenic conditions. Moreover, without being bound to a particular theory, we believe that HDL-associated Hb can serve as a novel biomarker for atherosclerosis or other pathologies characterized by an inflammatory response. Certain details of these studies are described in Example 3.

C) Acute Phase Proteins Associated with HDL in Mouse Models of Atherosclerosis/Hyperlipidemia.

As noted above we discovered that hemoglobin (Hb) with physical and chemical properties distinctly different from red blood cell Hb associates with HDL in animal models of atherosclerosis and contributes to the pro-inflammatory nature of HDL under atherogenic conditions. Thus, for example, feeding C57BL/6J mice (n=12 per group) an atherogenic diet for one week resulted in i) lower HDL-cholesterol levels, ii) reduced paraoxonase activity, and iii) increased reactive oxygen species and iv) reduced ability of the HDL to promote cholesterol efflux from macrophages, compared to C57BL/6J mice fed a chow diet (see, e.g., FIG. 19, Example 2).

Hemopexin and haptoglobin are two well-known scavengers of Hb. Haptoglobin (Hp) has been known to be associated with HDL and in addition to its concentration in plasma increasing with hemolysis, it also increases during an acute phase response. It was a surprising discovery of this invention that hemopexin (Hx) is also associated with pro-inflammatory HDL and similarly increases with an acute phase response.

As shown in FIG. 1, Western analysis showed increased (>10-fold) association of Hb, Hx, and Hp protein complexes with HDL fractions obtained from C57BL/6J mice fed an atherogenic diet (A) compared to a chow diet (C).

Hb, Hx, and Hp protein complexes were also found associated with HDL from apoE null mice on a chow diet. To determine if these elevated levels of HDL-associated proteins related to heme pathways were valid novel markers of the inflammation that constitutes atherosclerosis, these apoE null mice were treated with the apolipoprotein A-I mimetic peptide D-4F (50 μg/ml in drinking water) for up to 21 days and their HDL was analyzed for inflammatory properties and HDL-associated proteins related to heme pathways.

Figure 5:
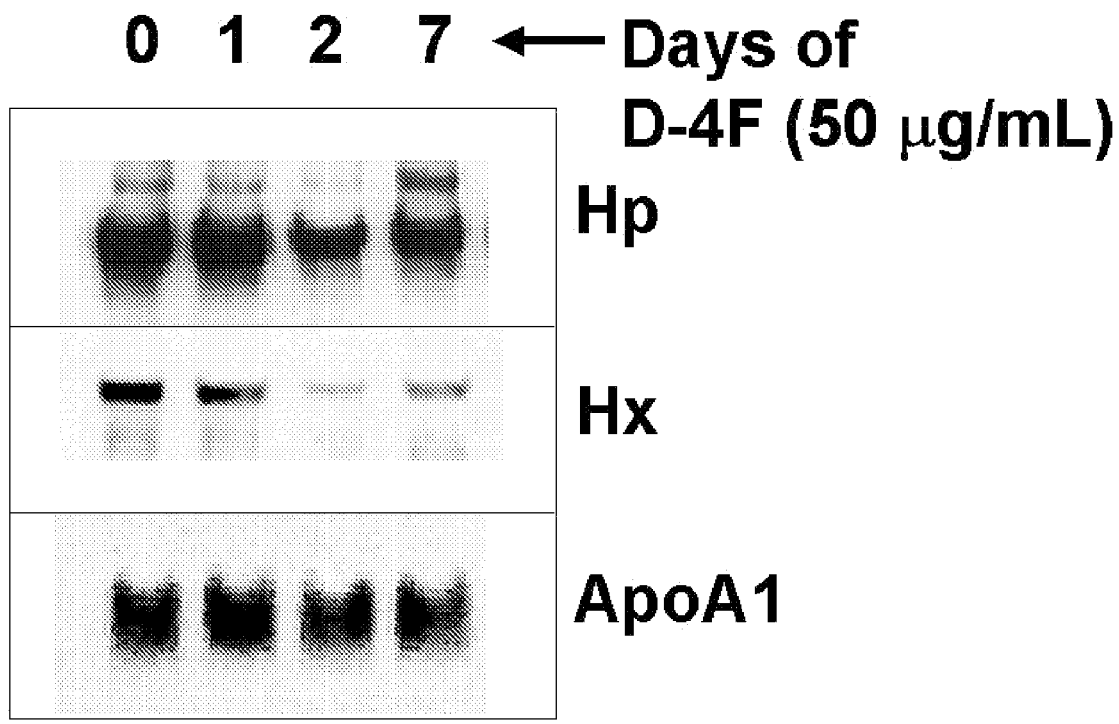
FIG. 5 shows that D-4F treatment reduces haptoglobin (Hp) and Hemopexin (Hx) in HDL of apoE null mice. HDL was isolated from mice described in FIG. 2 and the content of Hp, Hx, and apolipoprotein A-I (ApoA-I) were determined.
Figure 6:
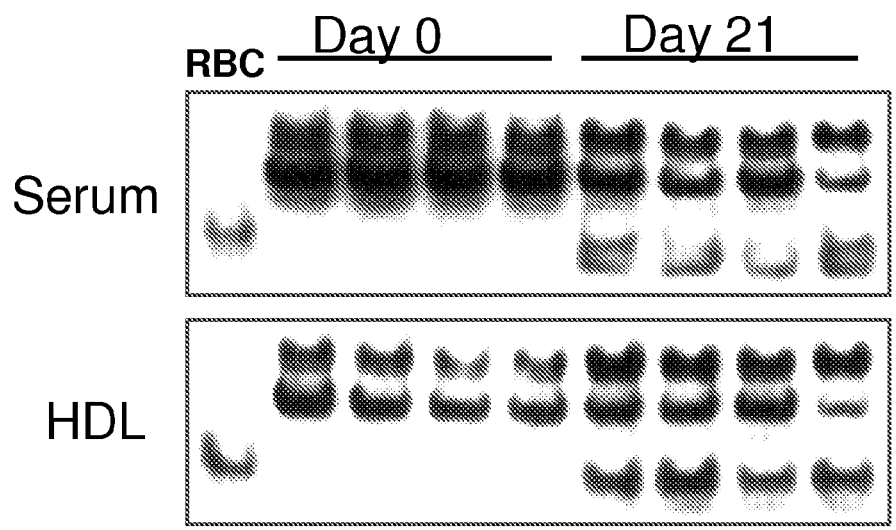
FIG. 6 shows that D-4F treatment resulted in an increase in non-RBC hemoglobin on native PAGE gels with molecular weights similar to that of the hemoglobin contained in RBC. Serum, HDL and red blood cells (RBC) from each of the 4 mice described in FIG. 2 prior to (Day 0) and after 21 days of treatment (Day 21) were run on native PAGE (4-15%) gels and were analyzed by Western analysis for hemoglobin. The data indicate that prior to treatment all of the hemoglobin in the sera and in the HDL-supernatants (which contain HDL and the non-lipoprotein fractions) ran on the native PAGE gels with an apparent molecular weight significantly higher than the hemoglobin from lysed RBC. However, after 21 days of treatment with D-4F a significant amount of the hemoglobin in sera and in the HDL-supernatants ran on the gels with an apparent molecular weight similar to that of the hemoglobin from lysed RBC.

D-4F treatment i) converted HDL from pro-inflammatory to anti-inflammatory (see, e.g., FIG. 2), ii) significantly reduced Hx (see, e.g., FIG. 3) and Hp (see, e.g., FIG. 4) levels in serum as measured by ELISA, iii) decreased Hx and Hp protein complexes in HDL fractions (see, e.g., FIG. 5) and iv) partially restored to normal (i.e. to that seen in red blood cells) the physical and chemical properties of Hb in apoE null serum and in apoE null HDL supernatants (see, e.g., FIG. 6). Thus, in certain embodiments this invention provides a method to detect heme-related proteins associated with HDL that are components of pro-inflammatory HDL.

Figure 7:
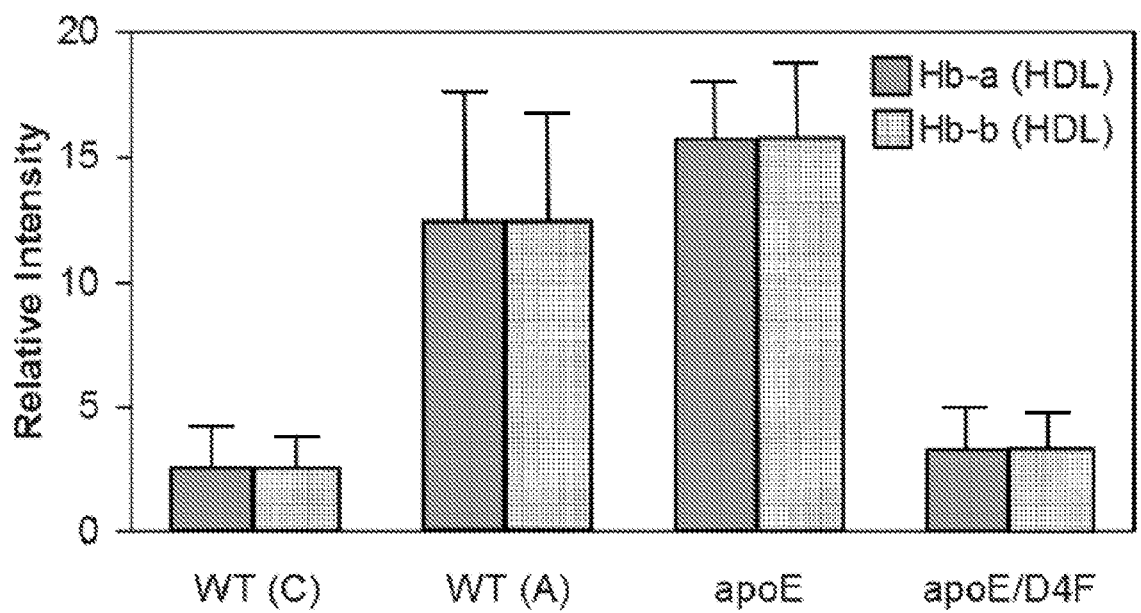
FIG. 7 shows that both alpha and beta chains of hemoglobin were increased in wild-type C57BL/6J mice fed an atherogenic diet. The figure also shows that the content of both α and β chains of hemoglobin were increased in apoE null mice on a chow diet and both chains decreased with D-4F treatment as described in FIG. 2.

As shown in FIG. 7 both alpha-(α-) and beta-(β-) chains of hemoglobin were increased in wild-type C57BL/6J mice fed an atherogenic diet. The content of both α and β chains of hemoglobin were increased in apoE null mice on a chow diet and both chains decreased with D-4F treatment.

Figure 8:
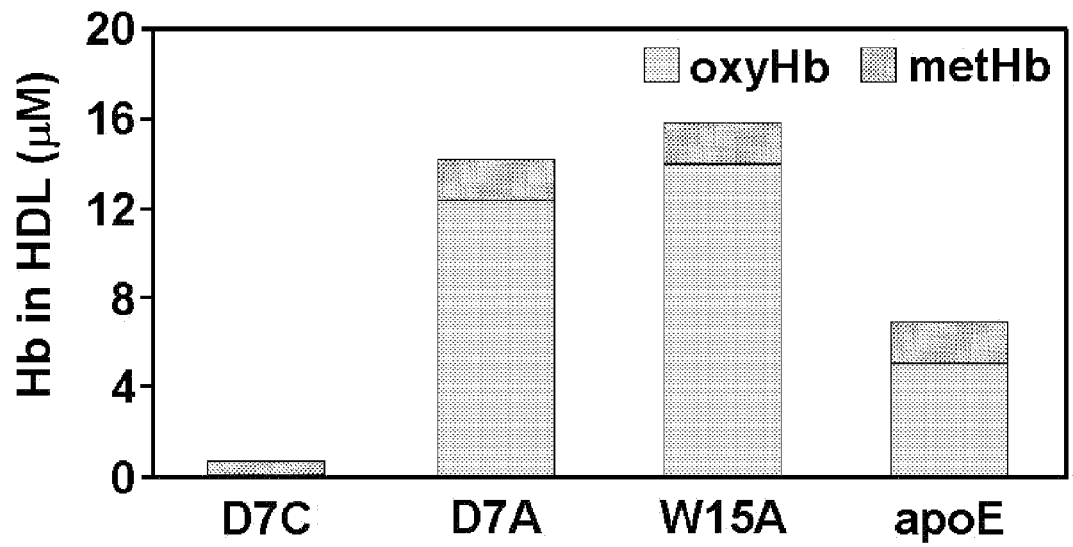
FIG. 8 shows that the content of oxy-hemoglobin and met-hemoglobin in HDL were determined in wild-type C57BL/6J mice fed chow for 7 days (D7C) or fed an atherogenic diet (D7A) for 7 days or for 15 weeks (W15A). The content of oxy-hemoglobin and met-hemoglobin were also determined in apoE null mice fed chow (apoE). As shown in the figure most of the HDL-associated hemoglobin in the C57BL/6J mice on the atherogenic diet and in the apoE null mice on the chow diet was oxy-hemoglobin.

As shown in FIG. 8, the content of oxy-hemoglobin and met-hemoglobin in HDL were determined in wild-type C57BL/6J mice fed chow for 7 days (D7C) or fed an atherogenic diet (D7A) for 7 days or for 15 weeks (W15A). The content of oxy-hemoglobin and met-hemoglobin were also determined in apoE null mice fed chow (apoE).

Figure 9:
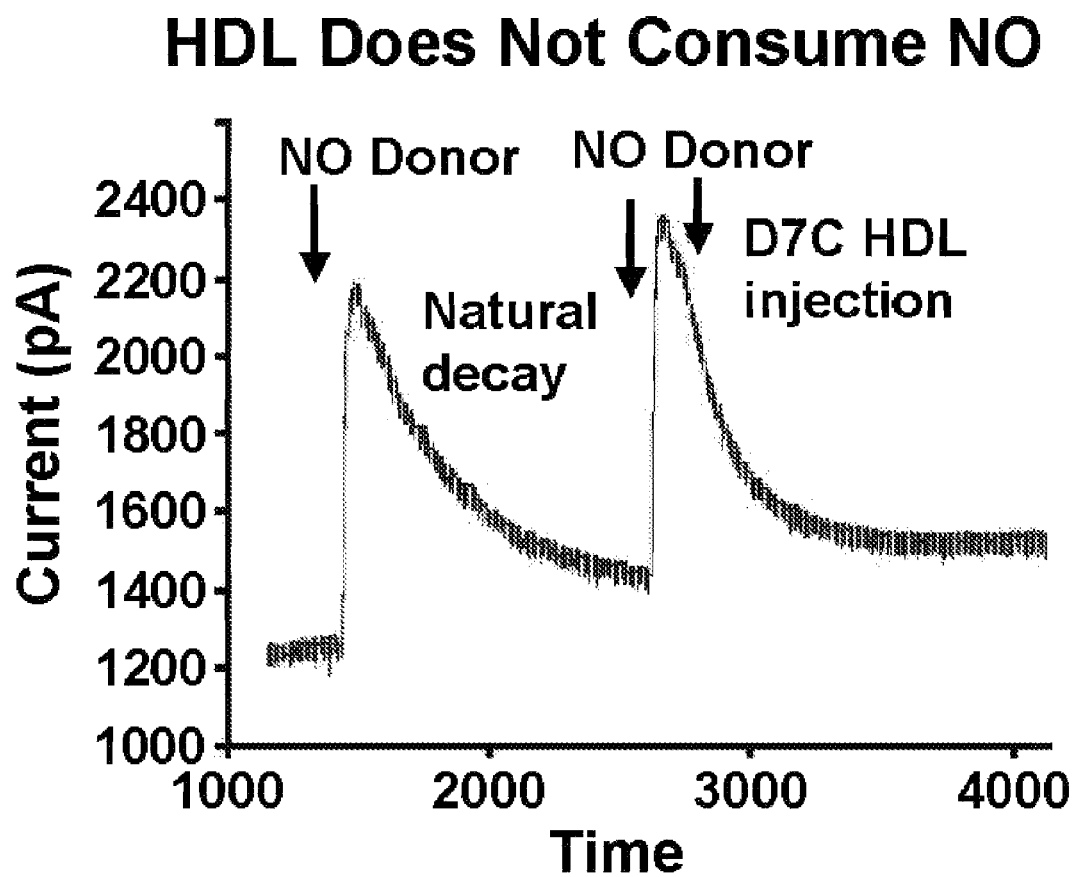
FIG. 9 shows that addition of HDL from wild-type C57BL/6J mice fed a chow diet for 7 days (D7C) did not consume nitric oxide generated chemically (NO donor) and measured as an electric current (pA).
Figure 10:
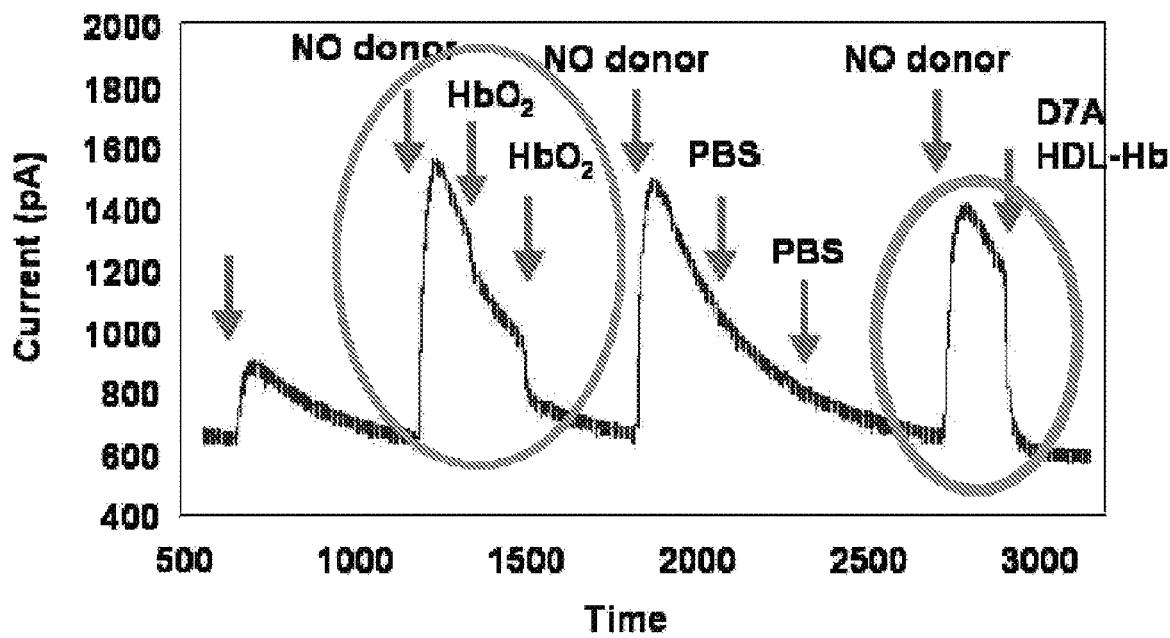
FIG. 10 shows that addition of oxy-hemoglobin ($HbO_2$) caused a rapid transient decrease in the decay curve of nitric oxide generated chemically (NO donor) and measured as an electric current (pA). Addition of phosphate buffered saline (PBS) did not alter the natural decay curve. In contrast, addition of HDL from wild-type C57BL/6J mice fed an atherogenic diet for 7 days (D7A HDL-Hb) caused a rapid and dramatic decrease in the decay curve indicating that this pro-inflammatory HDL rapidly consumed the nitric oxide.

Oxy-hemoglobin consumes nitric oxide while met-hemoglobin does not consume nitric oxide. As shown in FIG. 9 addition of normal mouse HDL did not alter the natural decay of chemically generated nitric oxide. In contrast, as shown in FIG. 10, when oxy-hemoglobin ($HbO_2$) was added to nitric oxide that was generated chemically (NO donor) and measured as current (pA) there was a sudden and dramatic change in the decay of the chemically generated nitric oxide indicating that it was consumed by the oxy-hemoglobin. As also shown in FIG. 10 addition of phosphate buffered saline (PBS) did not alter the decay curve indicating no consumption of nitric oxide occurred as a result of the addition of the vehicle (PBS). In contrast addition of HDL from wild-type C57BL/6J mice fed an atherogenic diet for 7 days (D7A HDL-Hb) resulted in a dramatic drop in the decay curve indicating that this pro-inflammatory HDL rapidly consumed the nitric oxide.

Figure 11:
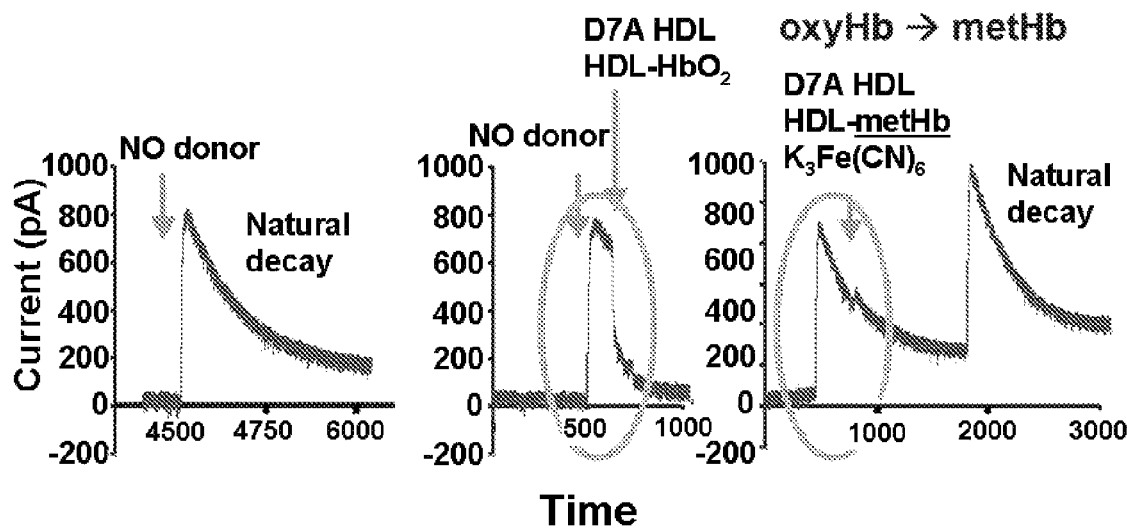
FIG. 11 shows that pro-inflammatory HDL (HDL from wild-type C57BL/6J mice fed an atherogenic diet for 7 days; D7A HDL) caused a rapid and dramatic decrease in the nitric oxide decay curve indicating that the pro-inflammatory HDL rapidly consumed the nitric oxide. However after treatment of this HDL with $K_3Fe(CN)_6$ which converted the oxy-hemoglobin in HDL (HDL-$HbO_2$) to met-hemoglobin (HDL-metHb) addition of the HDL failed to significantly alter the decay curve indicating that nitric oxide was not consumed.

As shown in FIG. 11 treating the pro-atherogenic HDL from mice fed the atherogenic diet with an agent [$K_3Fe(CN)_6$] that converts oxy-hemoglobin to met-hemoglobin reversed the ability of the pro-inflammatory HDL to rapidly consume nitric oxide.

Figure 12:
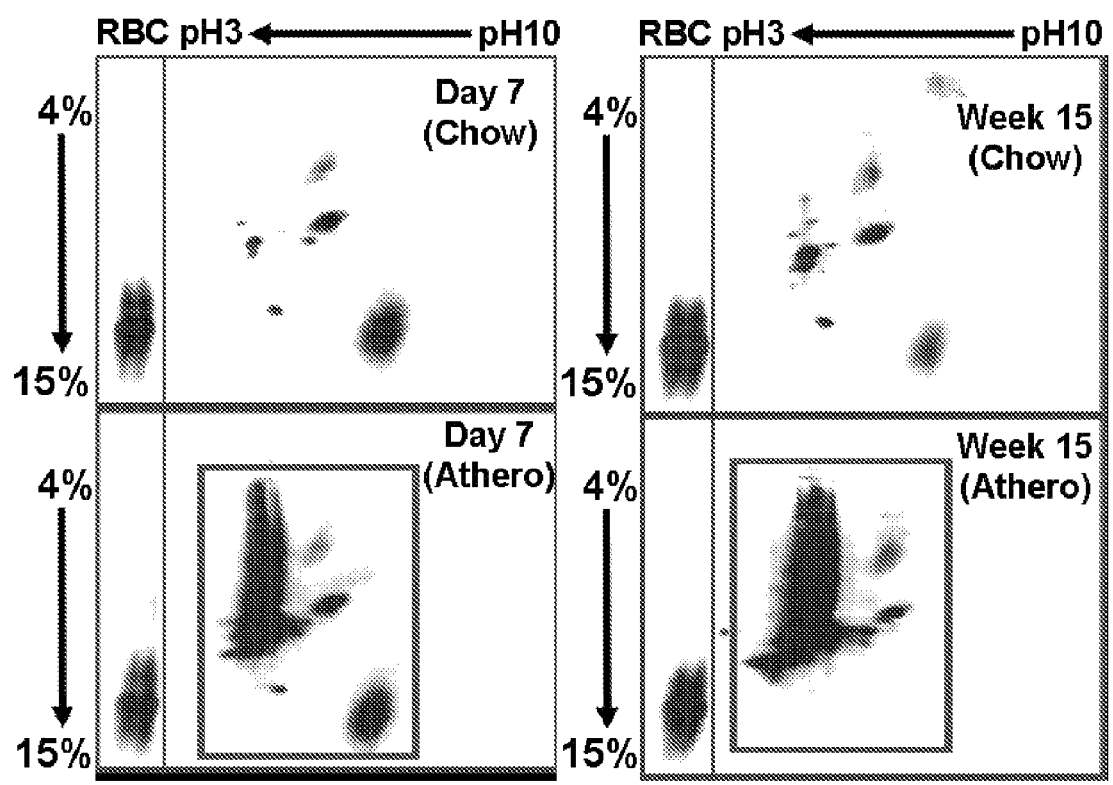
FIG. 12 shows two dimensional gels that were stained for hemoglobin using Western analysis of the serum of wild-type C57BL/6J mice fed a chow diet for 7 days (upper left panel), or for 15 weeks (upper right panel), or fed an atherogenic diet for 7 days (lower left panel) or for 15 weeks (lower right panel). The column to the far left of each panel represents the position of hemoglobin from lysed red blood cells (RBC) from each condition.
Figure 13:
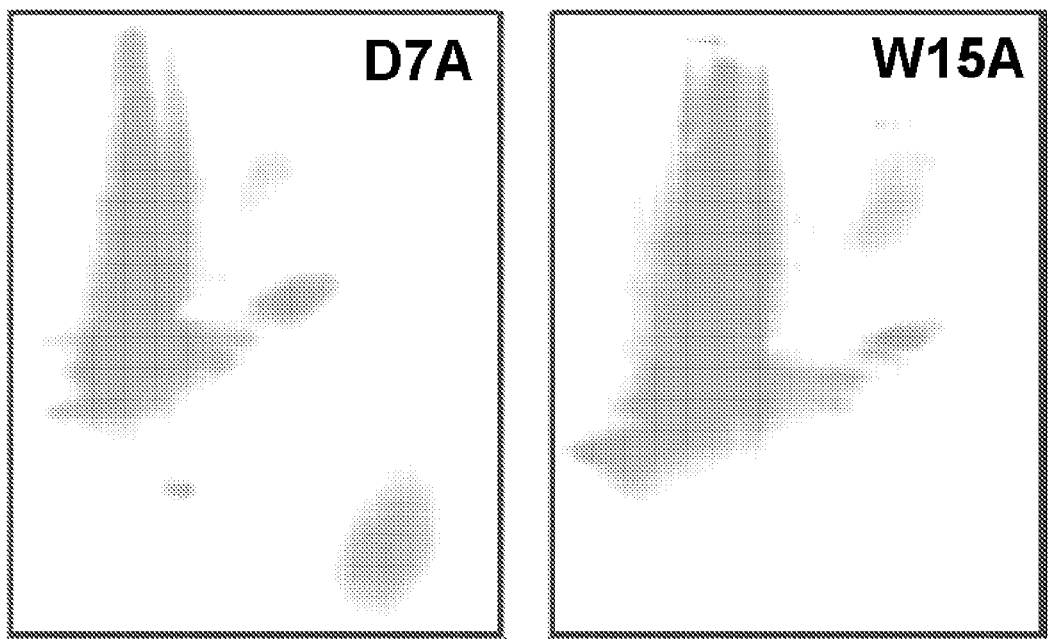
FIG. 13 shows the lower panels from FIG. 12 in which the wild-type C57BL/6J mice were fed an atherogenic diet for 7 days (D7A) or for 15 weeks (W15A) with the hemoglobin staining shown in light blue (reproduced as grey).
Figure 14:
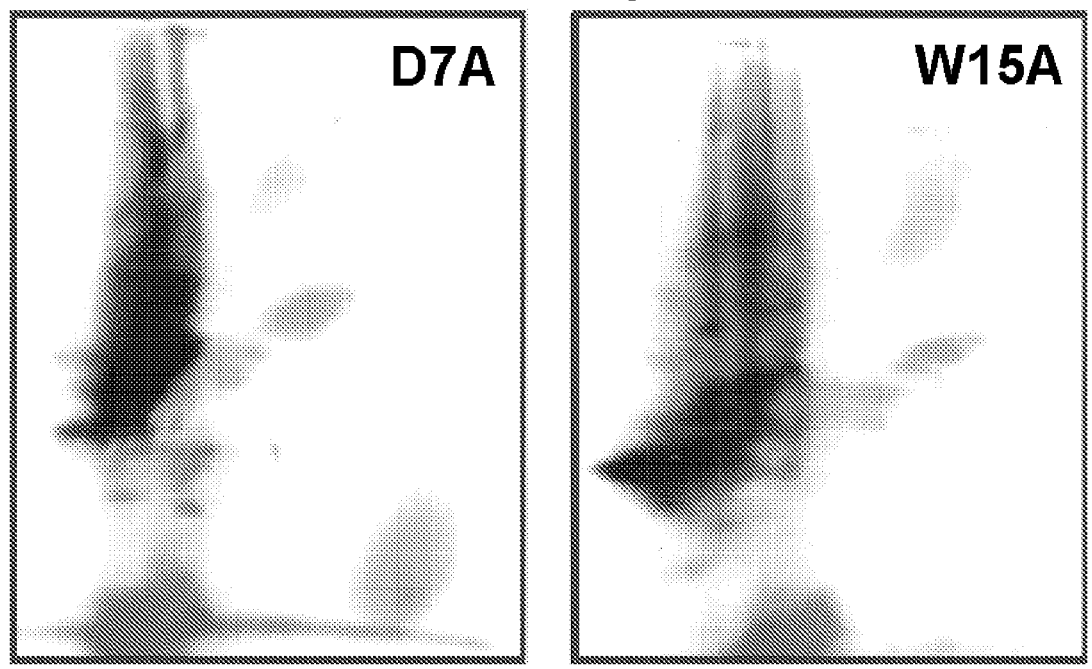
FIG. 14. The Western blots shown in FIG. 13 were stripped and re-probed with antibody to haptoglobin. The resultant images (magenta in color) were overlaid on the images in FIG. 13. The dark blue areas represent areas where both hemoglobin and haptoglobin co-localized.
Figure 15:
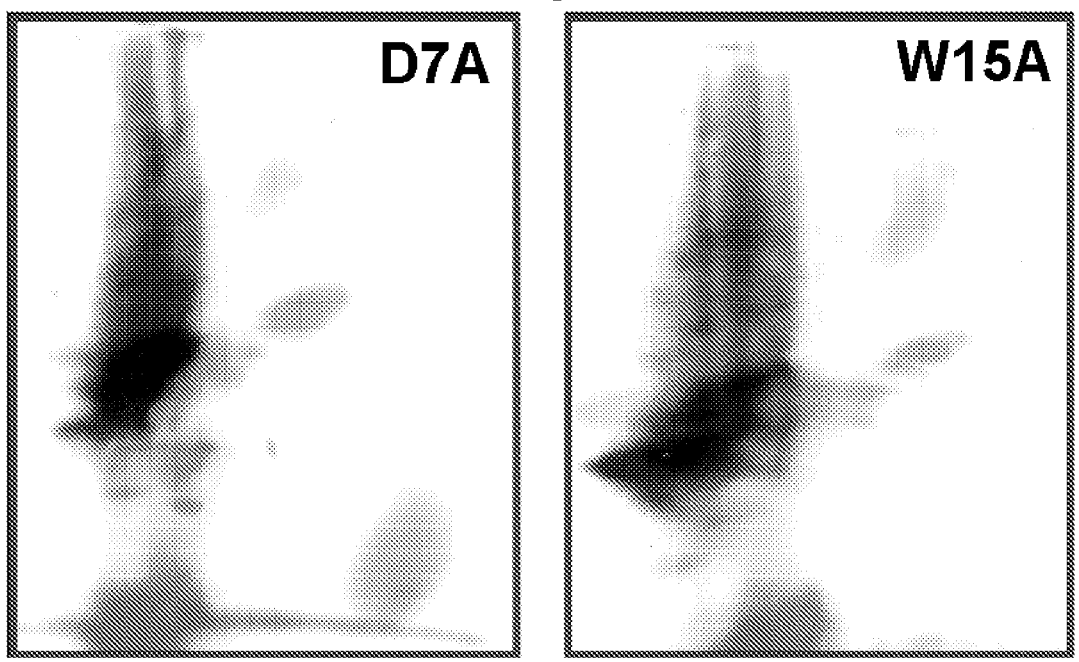
FIG. 15. The Western blots shown in FIG. 14 were stripped and re-probed with antibody to hemopexin. The resultant images (yellow) were overlaid on the images from FIG. 14. The very dark images indicate areas where hemoglobin, haptoglobin, and hemopexin co-localized.

FIG. 12 demonstrates two-dimensional gels for red blood cell (RBC) hemoglobin and hemoglobin in serum from wild-type C57BL/6J mice fed a chow diet for 7 days (upper left hand panel) or for 15 weeks (upper right hand panel) or fed an atherogenic diet for 7 days (lower left hand panel) or for 15 weeks (lower right hand panel). FIG. 13 reproduces the lower panels from FIG. 12 in which the wild-type C57BL/6J mice were fed an atherogenic diet for 7 days (D7A) or for 15 weeks W15A except that the hemoglobin staining is shown in light blue. The Western blots shown in FIG. 13 were stripped and re-probed with antibody to haptoglobin (FIG. 14). The Western blots shown in FIG. 14 were stripped and re-probed with antibody to hemopexin (FIG. 15).

The experiments demonstrated in FIGS. 12-15 indicate that hemoglobin, haptoglobin and hemopexin may be localized on the same particles in atherogenic serum.

As shown in FIG. 1, on the atherogenic diet these particles are largely associated with HDL. Feeding the atherogenic diet for 7 days to C57BL/6J mice that were null for haptoglobin and/or hemopexin demonstrated the important role of haptoglobin in the formation of pro-inflammatory HDL. Briefly, C57BL/6J mice that were wild-type (WT) or null for hemopexin (Hx) or null for haptoglobin (Hp) or null for both hemopexin and haptoglobin (Hp/Hx) were fed chow (C) or an atherogenic diet (A) for 7 days. The mice were bled and the cholesterol content and the heme content were determined in FPLC fractions of their plasma. Wild-type HDL had virtually no associated heme. When these mice were fed an atherogenic diet for 7 days there was heme associated with the HDL fractions (yellow line lower panels). In the absence of hemopexin there was heme associated with the HDL fractions even on the chow diet and the heme content increased in HDL in these mice when they were fed the atherogenic diet for 7 days. In contrast mice that lacked haptoglobin had no HDL-associated heme on the atherogenic diet (green line right lower panel; red line right lower panel). Thus haptoglobin was required for heme to associate with HDL.

In another experiment, C57BL/6J mice that were wild-type (WT) or null for hemopexin (Hx) or null for haptoglobin (Hp) or null for both hemopexin and haptoglobin (Hp/Hx) were fed chow or an atherogenic diet for 7 days. The mice were bled and the cholesterol content and the reactive oxygen species (ROS) content were determined in FPLC fractions of their plasma. HDL had virtually no associated ROS. When these mice were fed an atherogenic diet for 7 days there were ROS associated with the HDL fractions. In the absence of hemopexin there were ROS associated with the HDL fractions even on the chow diet and the ROS content increased in HDL in these mice when they were fed the atherogenic diet for 7 days. In contrast mice that lacked haptoglobin had no HDL-associated ROS on the atherogenic diet. Thus haptoglobin was required for ROS to associate with HDL.

The data presented here demonstrate the surprising finding that pro-inflammatory HDL can be detected by signature proteins associated with HDL or by the level of heme containing proteins associated with HDL. This invention also makes the unexpected finding that the ratio of the level of heme-containing and/or heme-binding proteins associated with HDL compared to the level of these proteins in the non-lipoprotein fractions of plasma/serum is predictive of pro-inflammatory HDL. This invention also makes the unexpected finding that in the absence of HDL-associated heme-containing and/or and heme-binding proteins HDL cannot exhibit pro-inflammatory characteristics (e.g. increased ROS content).

Based on these unexpected findings a number of assays are provided to identify pro-inflammatory (dysfunctional) HDL. Such assays include, but are not limited to the detection of one, two, three, four, five, six, seven, or eight proteins associated with HDL where the proteins have m/z ratios of about: 9.3; 14.9; 15.6; 15.8; 16.2; 16.5; 18.6; 19.5 where the association of these proteins with HDL indicate that said HDL is a pro-inflammatory HDL.

As noted above, it was a surprising discovery of this invention that the proteins with m/z ratios of 14.9 k and 15.6 k are hemoglobin alpha and beta chains, respectively. It was also a surprising discovery of this invention that the protein with the m/z ratio of 19.5 k is Group XII $PLA_2$.

In another embodiment, the assays involve measuring the level of heme containing and/or heme binding proteins (e.g. hemoglobin, haptoglobin, hemopexin, myeloperoxidase, etc.), or proteins that bind to heme-binding proteins such as soluble CD163 which are associated with HDL and where elevated levels of one or more, two or more, three or more or four of said proteins associated with HDL (e.g. as compared to the levels found in protective HDL) indicates that the HDL is pro-inflammatory HDL.

In certain embodiments the assays involve measuring the level of heme containing and/or heme binding proteins associated with HDL (e.g. hemoglobin, haptoglobin, hemopexin, myeloperoxidase) compared to the level of these heme-containing and/or heme-binding proteins in the non-lipoprotein fractions of HDL, where elevated levels (e.g. as compared to the levels found in protective HDL) indicates that the HDL is pro-inflammatory HDL. In various embodiments the assays involve determining the ratio of the level of heme containing proteins associated with HDL (e.g. hemoglobin, haptoglobin, hemopexin, myeloperoxidase) to the level of these heme-containing and/or heme-binding proteins in the non-lipoprotein fractions of plasma and/or serum where a ratio for at least one, at least two, at least three, or four of the proteins greater or equal to a value of about 0.2, 0.3, 0.4, 0.5, 0.6, 0.7, 0.8, 0.9, or 1 indicates that the HDL is pro-inflammatory HDL.

In various embodiments the predictive values of the assays is improved by measurements of two or more heme-containing and/or heme-binding proteins. In various embodiments the measurements of the two or more heme-containing and/or heme-binding proteins can be combined and/or weighted by other factors. Thus, for example, a descriminant function analysis or cluster analysis can be used to determine weighting factors for each of the measured proteins. In one illustrative example, one can calculate the product of the content of two or more of the heme-containing or heme-binding proteins (e.g., determining the value obtained by multiplying the values for each) such as shown in the example given in FIG. 28C). Using the example shown in FIG. 28C such an analysis can improve the predictive value of the assay in cases where hemolysis occurs either during the drawing of blood from the subject or in vitro after the blood has been drawn as indicated in the example shown in FIG. 27. Thus, for example, one can calculate the product of hemoglobin associated with HDL times the value of haptoglobin associated with HDL with both in micrograms HRP/mL to provide an assay metric.

In various embodiments the assays involve determining the level of heme associated with HDL and/or determining the iron content of HDL, and/or determining the level of iron containing proteins associated with HDL where elevated levels of these measures (e.g. as compared to the levels found in protective HDL) indicates that the HDL is pro-inflammatory HDL Also provided are assays that identify/quantify the ability of the HDL to consume nitric oxide.

II. Measurements of the Ability of HDL to Inhibit the Aggregation of LDL.

In various embodiments this invention also pertains to the surprising finding that pro-inflammatory HDL does not prevent LDL aggregation while anti-inflammatory HDL prevents LDL aggregation. Thus, LDL aggregation assays provide a convenient means of assaying and detecting pro-inflammatory HDL. Various LDL aggregation assays are known to those of skill in the art and it is not intended for this invention to be limited to any particular aggregation assay or format. One illustrative aggregation assay protocol is provided in Example 4.

Figure 16:
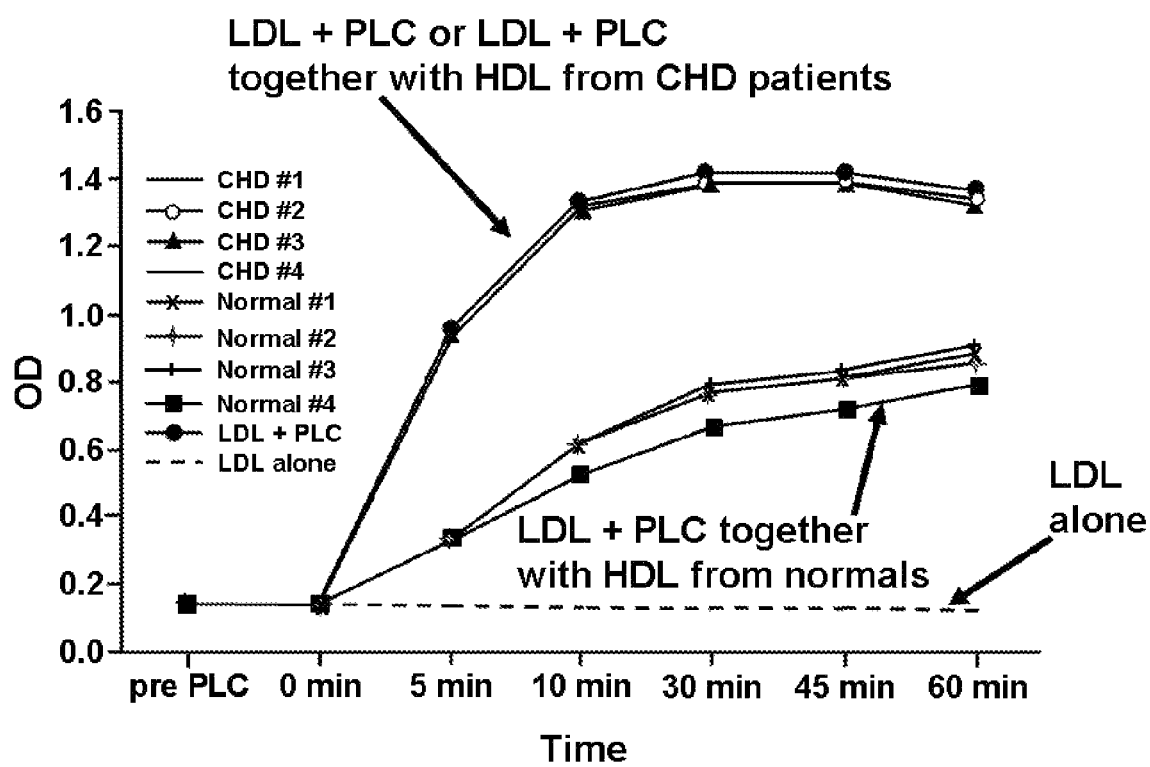
FIG. 16 shows that pro-inflammatory HDL does not inhibit LDL aggregation while Anti-inflammatory HDL does. HDL from four subjects with pro-inflammatory HDL and coronary artery disease or equivalents by NCEP ATP III criteria (CHD Patients) and from four healthy volunteers (Normals) were tested for their ability to inhibit LDL aggregation induced by phospholipase C (PLC). The values for the positive control (LDL+PLC) without added HDL is shown by the red line. The values for the negative control (LDL alone) is shown by the lowest blue line. The data indicate that HDL from the four CHD patients was unable to inhibit PLC induced LDL aggregation while HDL from the four healthy volunteers (Normals) significantly inhibited PLC induced LDL aggregation.
Figure 17:
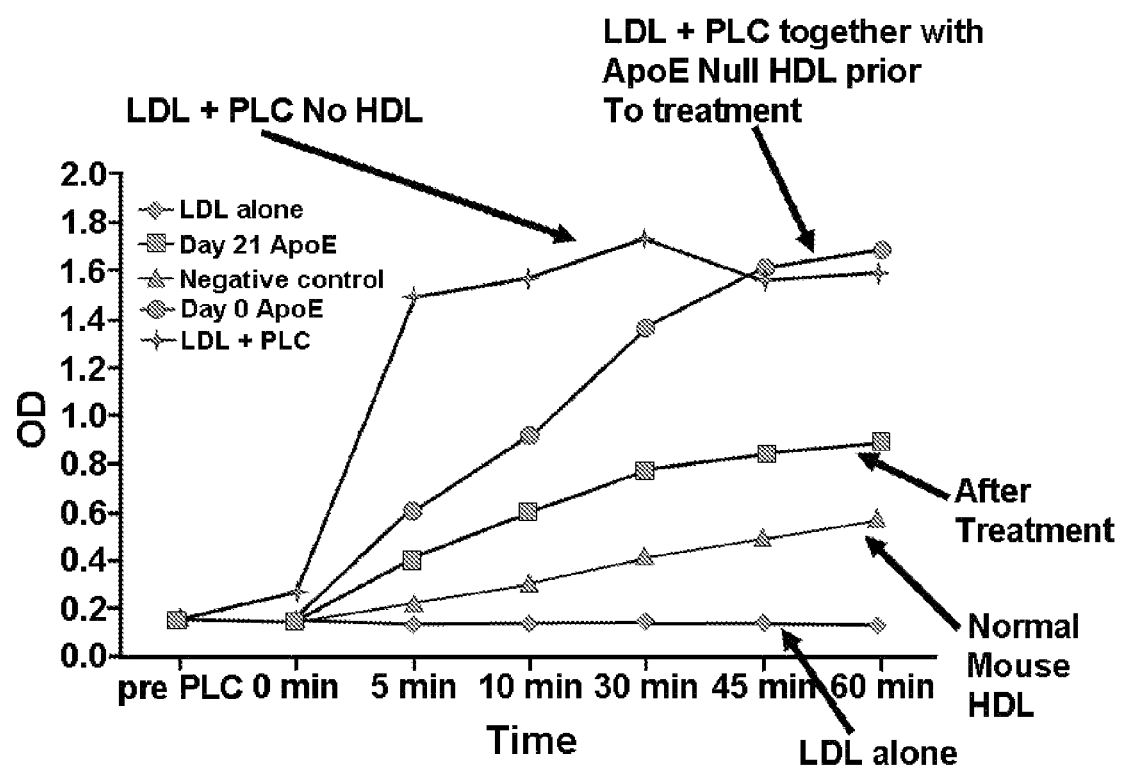
FIG. 17 shows that prior to treatment pro-inflammatory apoE null HDL does not inhibit phospholipase C (PLC) induced LDL aggregation but after 21 days of treatment with oral D-4F the HDL becomes anti-inflammatory and inhibits PLC-induced LDL aggregation. The ability of apoE null HDL prior to and after treatment with oral D-4F as described in FIG. 2 was tested for its ability to inhibit PLC-induced LDL aggregation.

As shown in FIG. 16, this assay allowed easy detection of pro-inflammatory HDL from subjects with CHD or CHD equivalents and the values were quite distinct from those obtained with HDL taken from healthy normal volunteers. As shown in FIG. 17 this assay allowed easy detection of pro-inflammatory HDL from apoE null mice (a mouse model of atherosclerosis) and the values were quite distinct from those obtained with normal mouse HDL. Moreover, this assay provided a simple means of demonstrating the effectiveness of treatment of the apoE null mice with the apoA-I mimetic peptide D-4F.

III. Uses of the Assays.

This invention thus provides a number of assays for the detection and/or quantitation of protective and/or dysfunctional (pro-inflammatory) HDL and such assays provide diagnostic and/or prognostic methods for the detection of atherosclerosis or other conditions characterized by an inflammatory response (e.g., atherosclerosis, stroke, leprosy, tuberculosis, systemic lupus erythematosus, polymyalgia rheumatica, polyarteritis nodosa, scleroderma, idiopathic pulmonary fibrosis, chronic obstructive pulmonary disease, Alzheimer's Disease, AIDS, polymyalgia rheumatica, polyarteritis nodosa, scleroderma, idiopathic pulmonary fibrosis, coronary calcification, calcific aortic stenosis, osteoporosis, a bacterial infection, a viral infection, a fungal infection, an autoimmune disorder, and rheumatoid arthritis, Chron's disease, and the like). The assays are also of great use in detecting persons at risk for atherosclerosis and other inflammatory conditions (e.g., as described above) and for monitoring the effectiveness of various treatments and treatment protocols.

In various embodiments the assays include measurements of heme-related HDL-associated proteins (e.g., hemoglobin, and/or haptoglobin, and/or hemopexin, and/or myloperoxidase, etc.), measurements of the relative distribution of HDL-associated proteins between HDL and the non-lipoprotein fractions of plasma/serum, measurements of the ability of pro-inflammatory HDL to consume nitric oxide, and measurement of the ability of HDL to inhibit LDL aggregation.

In this regard, it is noted that, while hemopexin is known to be a weak acute phase reactant, it has never previously been thought to be a predictor of atherosclerosis or dysfunctional HDL. Indeed to our knowledge its association with HDL has not previously been established. This protein has been thought to largely function together with haptoglobin to remove excess heme from the circulation. Thus, it was a surprising discovery that hemopexin is associated with HDL and that its concentration in plasma and particularly the content of hemopexin associated with HDL is highly predictive of atherosclerosis and dysfunctional HDL.

As indicated above, in certain embodiments, this invention contemplates diagnostic and/or prognostic methods for the detection of atherosclerosis or other conditions characterized by an inflammatory response. The diagnostic methods described herein are also useful in the treatment of various subjects. When a subject (e.g. a patient) is diagnosed with dysfunctional HDL they are a good candidate for a drug or drugs that restore or elevate protective HDL levels and/or various statins (e.g., atorvastatin (Lipitor®, Pfizer), simvastatin (Zocor®, Merck, pravastatin (Pravachol®, Bristol-Myers Squibb0, fluvastatin (Lescol®, Novartis), lovastatin (Mevacor®, Merck), rosuvastatin (Crestor®, Astra Zeneca), and Pitavastatin (Sankyo), and the like.). Such drugs (active agents) that restore or elevate protective HDL levels include, but are not limited to D4F (see, e.g., Li et al. (2004) *Circulation*, 110: 1701-1705), active agents listed in PCT/US2001/26497, and/or PCT/US2001/26497, and/or PCT/US2004/026288, and/or PCT/US2005/028294, and/or PCT/US2003/09988, and/or U.S. Ser. No. 10/273,386, all of which are incorporated herein by reference, and the like.

It will be appreciated that, in certain embodiments, the assays of this invention are typically performed in the context of a differential diagnosis that permits the skilled practitioner to identify the particular condition or conditions characterized by an inflammatory response in that subject.

IV. Detection/Quantitation of HDL-Associated Proteins.

In various embodiments the assays of this invention involve detecting and/or quantifying one or more proteins (e.g., HDL-associated proteins including, but not limited to, hemoglobin, haptoglobin, hemopexin, myeloperoxidase, transferrin, soluble CD163, and the like). These are well known and well characterized proteins. For example, haptoglobin (see, e.g., GenBank NP_005134) is a positive acute phase protein with relatively common polymorphisms (Vlierberghe et al. (2004) *Clinica Chimica Acta.*, 345: 35-42.) that typically binds to and facilitates regulation of free hemoglobin in blood. CD163 is a monocyte-macrophage specific scavenger receptor that mediates the uptake and clearance of haptoglobin-hemoglobin complexes (Aristoeli et al. (2006) *Atherosclerosis* 184; 342-347). Hemopexin is a 60K-Da plasma glycoprotein (Delanghe (2001) *Clinica Chimica Acta*, 312: 13-23) (see, e.g., GenBank NP_000604, PFAM Pfam database of protein families and HMMs accession number PF00045). When free heme is formed in the plasma during the breakdown of hemoglobin, myoglobin, or heme containing enzymes such as catalase, it binds to hemopexin in a 1:1 ratio (Delanghe and Langlois (2001) *Clinica Chimica Acta*, 312: 13-23; Shipulina et al. (2000) *J. Protein Chem.*, 19: 239-248; Solar et al. (1989) *FEBS Lett.*, 256: 225-229; Kuzelova et al. (1997) *Biochim. Biophys. Acta*, 1336: 497-501). Hemopexin is an important link between heme and iron metabolism acting with the other iron transporters haptoglobin and transferrin to maintain iron homeostasis by the liver (Delanghe and Langlois (2001) *Clinica Chimica Acta*, 312: 13-23).

Methods of detecting/quantifying hemoglobin, haptoglobin, hemopexin, myeloperoxidase, and the like are well known to those of skill in the art. For example, medical haptoglobin assays are performed in a differential diagnosis for acute rheumatic disease, biliary obstruction, peptic ulcer, ulcerative colitis, and the like (elevated haptoglobin) or chronic liver disease, erythroblastosis fetalis, hematoma, hemolytic anemias, hemolytic anemia due to G6PD deficiency, idiopathic autoimmune hemolytic anemia, immune hemolytic anemia, drug-induced immune hemolytic anemia, primary liver disease, and transfusion reaction (low haptoglobin levels).

Essentially any method used to detect/quantify a specific protein can be utilized in the methods of this invention. Such methods include, but are not limited to capillary electrophoresis, Western blots, mass spectroscopy, chromatography (e.g., HPLC), immunoassays, and the like.

A) Sample Collection and Processing.

The hemoglobin, haptoglobin, hemopexin, myeloperoxidase, or the like is preferably quantified in a biological sample derived from a mammal (e.g., whole blood, plasma, etc.), more preferably from a human patient. As used herein, a biological sample is a sample of biological tissue or fluid that contains one or more assay proteins as described herein (e.g., haptoblobin and/or hemopexin) at a concentration that can be correlated with the presence and/or level of dysfunctional HDL. Certain preferred biological samples include, but are not limited to whole blood, or various blood fractions (e.g., plasma, serum, etc.). In certain embodiments the biological sample comprises HDL. In certain embodiments the biological sample includes, or an additional sample is provided that comprises serum or plasma.

The biological sample can be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

As indicated above, in certain embodiments, assays are performed using whole blood, serum, or plasma. Obtaining and storing blood and/or blood products are well known to those of skill in the art. Typically blood is obtained by venipuncture. The blood may be diluted by the addition of buffers or other reagents well known to those of skill in the art and may be stored for up to 24 hours at 2-8° C., or at −20° C. or lower for longer periods, prior to measurement. In a particularly preferred embodiment, the blood or blood product (e.g. serum) is stored at −70° C. without preservative indefinitely.

In various embodiments, as described above, the sample comprises HDL and/or HDL is isolated from the sample. Methods of isolating HDL are well known to those of skill in the art and are illustrated herein in the examples.

B) Immunological Binding Assays.

In a preferred embodiment, the protein(s) are detected and/or quantified in the biological sample using any of a number of well recognized immunological binding assays (see, e.g., U.S. Pat. Nos. 4,366,241; 4,376,110; 4,517,288; 4,837,168, 6,974,704, 6,964,872, 6,887,362, 6,878,558, 6,855,562, 6,849,457, 6,835,543, 6,830,731, 6,818,456, 6,818,455, 6,770,489, 6,737,277, 6,723,524, 6,689,317, 6,682,648, 6,673,562, 6,632,603, and the like). For a review of the general immunoassays, see also *Methods in Cell Biology Volume 37: Antibodies in Cell Biology*, Asai, ed. Academic Press, Inc.

New York (1993); *Basic and Clinical Immunology* 7th Edition, Stites & Terr, eds. (1991).

Immunological binding assays (or immunoassays) typically utilize a "capture agent" to specifically bind to and often immobilize the analyte (in this case hemoglobin, haptoglobin, hemopexin, myeloperoxidase, and the like, and/or fragment(s) thereof). The capture agent is a moiety that specifically binds to the analyte. In a preferred embodiment, the capture agent is an antibody that specifically binds in this case to hemoglobin, haptoglobin, hemopexin, myeloperoxidase, or the like and/or to fragment(s) or isoforms thereof.

In this regard it is noted that monoclonal and polyclonal antibodies for detecting and quantifying hemoglobin, haptoglobin, hemopexin, and myeloperoxidase, and the like, are commercially available (see, e.g. anti-haptoblobin antibodies ab8968 (sheep polyclonal), ab4248 (chicken polyclonal), and ab13429 (mouse monoclonal), anti-hemopexin antibodies ab27710 (mouse monoclonal) and ab27711 (mouse monoclonal from Abcam, Inc.), etc.

Immunoassays also often utilize a labeling agent to specifically bind to and label the binding complex formed by the capture agent and the analyte. Alternatively, the labeling agent may be a third moiety, such as another antibody, that specifically binds to the antibody/haptoglobin and/or antibody/hemopexin.

In certain embodiments, the labeling agent comprises an anti-haptoglobin and/or anti-hemopexin and/or anti hemoglobin, and/or anti-myeloperoxidase antibody bearing a label. Alternatively, the antibody may lack a label, but it may, in turn, be bound by a labeled third antibody specific to antibodies of the species from which the antibody is derived. Thus, for example, an anti-haptoglobin antibody modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, e.g., Kronval, et al. (1973) *J. Immunol.*, 111:1401-1406; Akerstrom, et al. (1985) *J. Immunol.*, 135:2589-2542, etc.).

Throughout the assays, incubation and/or washing steps may be performed after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 4° C. to 40° C.

1) Non-Competitive Assay Formats.

In various embodiments immunoassays for detecting or quantifying hemoglobin, haptoglobin, hemopexin, myeloperoxidase, and the like can be either competitive or noncompetitive. Noncompetitive immunoassays are assays in which the amount of captured analyte (in this case hemoglobin, and/or haptoglobin, and/or hemopexin, and/or myeloperoxidase, and the like) is directly measured. In one preferred "sandwich" assay, for example, the capture agent (e.g., anti-haptoblobin antibodies and/or anti-hemoglobin antibodies, and/or anti-hemopexin antibodies, and/or anti-myeloperoxidase antibodies) can be bound directly to a solid substrate where they are immobilized. These immobilized antibodies then capture hemoglobin, haptoglobin, hemopexin, and/or myeloperoxidase present in the test sample. The captured protein thus immobilized is then bound by a labeling agent, such as a second haptoblobin and/or hemopexin antibody bearing a label.

Alternatively, the second antibody can lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2) Competitive Assay Formats.

In competitive assays, the amount of analyte (hemoglobin, haptoglobin, hemopexin, myeloperoxidase, and the like) present in the sample is measured indirectly by measuring the amount of an added (exogenous) analyte (e.g., haptoblobin, hemopexin, hemoglobin, myeloperoxidase, etc.) displaced (or competed away) from a capture agent (e.g. anti-hemoglobin, haptoglobin, hemopexin, myeloperoxidase antibody) by the analyte present in the sample. In one competitive assay, a known amount of, in this case, hemoglobin, haptoglobin, hemopexin, myeloperoxidase, and the like is added to the sample and the sample is then contacted with a capture agent, in this case an antibody that specifically binds hemoglobin, haptoglobin, hemopexin, myeloperoxidase, and the like. The amount of hemoglobin, haptoglobin, hemopexin, myeloperoxidase, and the like bound to the antibody is inversely proportional to the concentration of analyte present in the sample.

In certain embodiments, the antibody is immobilized on a solid substrate. The amount of hemoglobin, haptoglobin, hemopexin, myeloperoxidase, and the like bound to the antibody can be determined either by measuring the amount of hemoglobin, haptoglobin, hemopexin, myeloperoxidase, and the like present in the antibody/analyte complex, or alternatively, by measuring the amount of remaining uncomplexed hemoglobin, haptoglobin, hemopexin, myeloperoxidase, and the like. The amount of hemoglobin, haptoglobin, hemopexin, myeloperoxidase, and the like can be detected by providing a labeled hemoglobin, haptoglobin, hemopexin, myeloperoxidase, and the like.

A hapten inhibition assay is another suitable competitive assay. In this assay a known analyte, in this case hemoglobin, haptoglobin, hemopexin, myeloperoxidase, and the like is immobilized on a solid substrate. A known amount of anti-hemoglobin, haptoglobin, hemopexin, myeloperoxidase, and the like antibody is added to the sample, and the sample is then contacted with the immobilized hemoglobin, haptoglobin, hemopexin, myeloperoxidase, and the like. In this case, the amount of anti-hemoglobin, haptoglobin, hemopexin, myeloperoxidase, and the like antibody bound to the immobilized hemoglobin, haptoglobin, hemopexin, myeloperoxidase, and the like is inversely proportional to the amount of analyte present in the sample. Again the amount of immobilized antibody can be detected by detecting either the immobilized fraction of antibody or the fraction of the antibody that remains in solution.

Detection can be direct where the antibody is labeled or indirect by the subsequent addition of a labeled moiety that specifically binds to the antibody as described above.

3) Protein Detection by RIA.

In certain embodiments, the hemoglobin, and/or haptoglobin, and/or hemopexin, and/or myeloperoxidase content of a sample is quantified using radioimmunoassay (RIA). Detailed protocols for radioimmunoassays can be found, for example in Sambrook et al. (1989) *Molecular Cloning—A Laboratory Manual* (2nd ed.) Vol. 1-3, Cold Spring Harbor Laboratory, Cold Spring Harbor Press, NY, and the like.

4) Other Assay Formats.

In another embodiment, Western blot (immunoblot) analysis is used to detect and quantify the presence of analyte protein(s) in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target analyte (e.g., hemoglobin, haptoglobin, hemopexin, myeloperoxidase, and the like). Antibodies specific for the analyte(s) of interest specifically bind to analyte present on the solid support. These antibodies can be directly labeled or alternatively may be subsequently detected using labeled antibodies (e.g., labeled sheep anti-mouse antibodies) that specifically bind to the anti-haptoglobin and/or hemopexin.

Other assay formats include, but are not limited to, liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5: 34-41).

The foregoing assays are intended to be illustrative and not limiting. Using the teaching provided herein, other assay formats will be apparent to one of skill in the art. It is noted that particular protocols are also provided herein in the Examples.

C. Scoring the Assay.

The assays of this invention are scored according to standard methods well known to those of skill in the art. The assays of this invention are typically scored as positive where there is where the difference in the levels of the assayed proteins is detectable. In certain embodiments, the change is a statistically significant change, e.g. as determined using any statistical test suited for the data set provided (e.g., t-test, analysis of variance (ANOVA), semiparametric techniques, non-parametric techniques (e.g., Wilcoxon Mann-Whitney Test, Wilcoxon Signed Ranks Test, Sign Test, Kruskal-Wallis Test, etc.). Preferably the statistically significant change is significant at least at the 85%, more preferably at least at the 90%, still more preferably at least at the 95%, and most preferably at least at the 98% or 99% confidence level). In certain embodiments, the change is at least a 10% change, preferably at least a 20% change, more preferably at least a 50% change and most preferably at least a 90% change.

V. Nitric Oxide Assays.

It was also a discovery of the present invention that pro-inflammatory HDL consumes nitric oxide (to produce nitrate), while protective HDL does not substantially consume nitric oxide. Thus measures of nitric oxide consumption/depletion provide a rapid and convenient assay for protective HDL.

Methods of detecting nitric oxide consumption are well known to those of skill in the art. The methods typically involve providing nitric oxide or a chemical donor of nitric oxide and using absorbance spectroscopy or electrochemical methods to detect the consumption of the nitric oxide.

VI. LDL Aggregation Assays.

In certain embodiments assays for non-protective HDL are provided based on the ability of protective HDL to prevent LDL aggregation, while the pro-inflammatory HDL does not prevent LDL aggregation. The assays generally involve contacting LDL (e.g. isolated LDL) with the HDL in question and measuring the aggregation amount or rate of the LDL. Methods of measuring LDL aggregation are well known to those of skill in the art.

In one simple embodiment, the LDL is simply vortexed into solution and the aggregation rate is measured spectrophotometrically, e.g. by reading absorbance at 680 nm over time (e.g., every 10 s) against an appropriate control (e.g., a blank solution, and/or the same experiment run with protective HDL) (see, e.g., Khoo et al. (1988) *Arteriosclerosis* 8: 348-358 for an illustrative aggregation assay). In certain embodiments aggregation is measured using an albumin depletion column, e.g. as described in Example 4.

VII. Assay Optimization.

The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred isolation conditions), antibody conditions that maximize signal to noise, protocols that improve throughput, etc. In addition, assay formats can be selected and/or optimized according to the availability of equipment and/or reagents.

Routine selection and optimization of assay formats is well known to those of ordinary skill in the art.

VIII. Kits.

In certain embodiments, this invention contemplates kits for performing one or more of the assays described herein. Typically such kits will include one or more reagents for the detection of hemoglobin, and/or myeloperoxidase, and/or haptoglobin and/or hemopexin. Such reagents can include, but are not limited to antibodies specific for the various proteins. In certain embodiments the kits comprise one or more reagents for performing LDL agglutination assays or nitric oxide consumption assays.

The kits can optionally contain additional materials for the collection of blood, and/or the isolation of HDL and/or LDL, and the like.

In addition, the kits can, optionally, include instructional materials containing directions (i.e., protocols) for the practice of the methods of this invention. Preferred instructional materials provide protocols utilizing the kit contents for measuring haptoglobin and/or hemopexin levels. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Measurements of Hemoglobin, Haptoglobin and Hemopexin

The ELISA protocols for haptoglobin and for hemopexin are shown below as are the protocols for preparing HDL-supernatants and for apoA-I associated immunoabsorbed proteins.

Human Hemoglobin ELISA

TABLE 1

Materials for hemoglobin ELISA.

| | Materials | Vendor | Catalog Number |
|---|---|---|---|
| 1 | HRP Conjugated Goat anti-Human Hemoglobin | Novus Biologicals | ab19362 |
| 2 | Plate reader (e.g. VersaMax Tunable Devices) | Molecular | |
| 3 | Round bottom 96 well plate, polypropylene, non-sterile | Fisher | |
| 4 | Immulon plates | Nunc | 12-565-502 |
| 5 | TMB | Fisher | F25-034-03 |
| 6 | $H_2SO_4$ | Fisher | |

Note:
Bring all reagents to room temperature before use.

HDL Isolation with Magnetic Bead Reagent

1. Separate plasma or serum from blood sample using green top tube or serum separator tube and centrifuging @ 5° C. @ 2300 rpm for 20 minutes.

2. Remove supernatant (serum or plasma). Note: If sample is already frozen, thaw the sample and spin in centrifuge @ room temp. @ 12,000 rpm for 5 minutes. This should bring down any particles present in the serum or plasma that might affect the assay.

3. Add supernatant (250 μL/well maximum) to clear round bottom 96 well plate.

4. Add ⅕ the total volume of the supernatant of magnetic bead reagent (50 μL/well maximum) to each sample and mix. Allow to sit for 5 minutes.

5. Place plate on top of magnetic particle concentrator for 5 minutes.

6. Remove supernatant and add to microcentrifuge tubes. Note: The supernatant contains HDL. ApoB containing particles have been removed.

7. Centrifuge @ 5° C. @ 12,000 rpm for 5 minutes to remove any beads.

8. Remove supernatant.

Preparation of Buffers

1. Make coating buffer: 25 mL dd$H_2O$+8 mL Buffer A+17 mL Buffer B (Buffer A: 0.2M $Na_2CO_3$; Buffer B: 0.2M $NaHCO_3$ 2. Make wash buffer: 0.75 mL TWEEN® 20+150 mL 10×PBS+1350 mL dd$H_2O$.

3. Make blocking/dilution buffer: 20 mL 10×PBS+10 mL TWEEN® 20+0.5 g BSA+170 mL dd$H_2O$.

4. Make stop solution: 1.38 mL $H_2SO_4$+48.62 mL $H_2O$.

Preparation of Samples and Standard Curve

1. Dilute samples (serum or HDL supernatant) 1:200 into coating buffer (2.5 μL HDL into 497.5 μL coating buffer).

2. Make hemoglobin in coating buffer at a concentration of 1000 ng/mL (2 μL hemoglobin into 2 mL coating buffer).

3. Prepare triplicate standard points by serially diluting the 1000 ng/mL solution 1:2 with coating buffer to produce 500, 250, 125, 62.5, 31.25, 15.63 ng/mL solutions.

4. Include a well with only coating buffer for a blank.

Addition of Samples and Standards to Plate

1. Add 110 μL of each standard and each sample in triplicate to the round bottom 96 well, polypropylene plate.

2. Using a multi-channel pipet, remove 100 μL from each of the wells to add to the Immulon plate.

3. Incubate overnight at 4° C.

4. Flick antigen into biohazard waste container.

5. Wash three times with 300 μL of wash buffer. Invert the plate and decant the contents, and hit it 4-5 times on absorbent paper towel to completely remove liquid at each step.

Blocking and Primary Antibody

1. Add 200 μL of blocking buffer to all wells and incubate at room temperature for 1 hr.

2. Wash three times with 300 μL of wash buffer. Invert the plate and decant the contents, and hit it 4-5 times on absorbent paper towel to completely remove liquid at each step.

3. Dilute HRP Conjugated Goat anti-Human Hemoglobin 1:10000 (1 μL antibody in 10 mL dilution buffer).

4. Add 50 μL of 1:20000 dilutions to each well.

5. Wash three times with 300 μL of wash buffer. Invert the plate and decant the contents, and hit it 4-5 times on absorbent paper towel to completely remove liquid at each step.

Addition of TMB and Stop Solution

1. Mix one part TMB A with one part TMB B.

2. Add 100 μL of TMB mixture to each well and incubate for 20 minutes.

3. Add 100 μL of stop solution to each well.

Read in Plate Reader

1. Read in the plate reader at a wavelength of 450 nm.

Haptoglobin ELISA

TABLE 2

Materials for haptoglobin ELISA.

| Materials | Vendor | Catalog Number |
|---|---|---|
| AssayMax Human Haptoglobin ELISA Kit | AssayPro | EH1003-1 |
| Plate reader (e.g. VersaMax Tunable) | Molecular Devices | |
| Round bottom 96 well plate, polypropylene, non-sterile | Fisher | 12-565-502 |

Note:
Bring all reagents to room temperature before use.

HDL Isolation with Magnetic Bead Reagent

1. Separate plasma or serum from blood sample using green top tube or serum separator tube and centrifuging at 5° C. at 2300 rpm for 20 minutes.

2. Remove supernatant (serum or plasma). Note: If sample is already frozen, thaw the sample and spin in centrifuge at room temperature at 12,000 rpm for 5 minutes. This should bring down any particles present in the serum or plasma that might affect the assay.

3. Add supernatant (250 μL/well maximum) to clear round bottom 96 well plate.

4. Add ⅕ the total volume of the supernatant of magnetic bead reagent (50 μL/well maximum) to each sample and mix. Allow to sit for 5 minutes.

5. Place plate on top of magnetic particle concentrator for 5 minutes.

6. Remove supernatant and add to microcentrifuge tubes. Note: The supernatant contains HDL. ApoB containing particles have been removed.

7. Centrifuge at 5° C. at 12,000 rpm for 5 minutes to remove any beads.

8. Remove supernatant.

Preparation of Buffers

1. Dilute the Wash Buffer Concentrate (provided in the kit) 1:10 with reagent grade water.

2. Dilute the EIA Diluent Concentrate (provided in the kit) 1:10 with reagent grade water.

Preparation of Plasma/Sera or HDL Supernatants

1. Dilute plasma/sera or HDL supernatant 1:4000 into EIA diluent (provided in the kit).
2. Start by diluting 1:100 (5 µL HDL into 495 µL diluent).
3. Make 40-fold dilution of 1:100 (12.5 µL of 1:100 into 487.5 µL diluent)

Preparation of Standard Curve

1. Reconstitute 100 µg of Haptoglobin Standard (provided in the kit) with 2 mL of EIA diluent to make a concentration of 50 µg/mL.
2. Allow the standard to sit for 10 minutes with gentle agitation prior to making dilutions.
3. Prepare triplicate standard points by serially diluting the standard solution (50 µg/mL) 1:4 with EIA diluent to produce 12.5, 3.13, 0.78, 0.195, and 0.049 µg/mL solutions.

Addition of Samples to Plate

1. Dilute Biotinylated Haptoglobin (provided in the kit) with 4 mL EIA diluent.
2. Add 35 µL of each standard and each sample in triplicate to the round bottom 96 well, polypropylene plate.
3. Using a multi-channel pipet, remove 25 µL from each of the wells to add to the Human Haptoglobin Microplate (provided in the kit).
4. Using a multi-channel pipet, add 25 µL of biotinylated haptoglobin to each of the wells.
5. Cover wells with sealing tape (provided in the kit) and incubate at room temperature for 1 hr with gentle agitation.
6. Wash five times with 200 µL of Wash Buffer. Invert the plate and decant the contents, and hit it 4-5 times on absorbent paper towel to completely remove liquid at each step.

Addition of Streptavidin-Peroxidase Conjugate

1. Spin down the Streptavidin-Peroxidase conjugate briefly
2. Dilute the conjugate 1:100 with EIA diluent.
3. Add 50 µL of the SP conjugate to each well and incubate for 30 minutes.
4. Wash five times with 200 µL of Wash Buffer. Invert the plate and decant the contents, and hit it 4-5 times on absorbent paper towel to completely remove liquid at each step.

Addition of Substrate and Stop Solution

1. Add 50 µL of Chromogen Substrate (provided in the kit) per well and incubate for 8 minutes.
2. Add 50 µL of Stop Solution (provided in the kit) to each well.

Read in Plate Reader

1. Read in the plate reader at a wavelength of 450 nm.

Hemopexin ELISA

TABLE 3

Materials for Hemopexin assay.

| Materials | Vendor | Catalog Number |
|---|---|---|
| HRP Conjugated Chicken anti-Human Hemopexin | Immunology Consultants Laboratory | CHX-80P |
| Hemopexin from Human Plasma | Athens Research & Technology, Inc. | |
| Plate reader (e.g. VersaMax Tunable) | Molecular Devices | |
| Round bottom 96 well plate, polypropylene, non-sterile | Fisher | 12-565-502 |
| Immulon plates | Nunc | F25-034-03 |
| TMB | Fisher | |
| $H_2SO_4$ | Fisher | |

Note:
Bring all reagents to room temperature before use.

HDL Isolation with Magnetic Bead Reagent

1. Separate plasma or serum from blood sample using green top tube or serum separator tube and centrifuging @ 5° C. @ 2300 rpm for 20 minutes.
2. Remove supernatant (serum or plasma). Note: If sample is already frozen, thaw the sample and spin in centrifuge @ room temp. @ 12,000 rpm for 5 minutes. This should bring down any particles present in the serum or plasma that might affect the assay.
3. Add supernatant (250 µL/well maximum) to clear round bottom 96 well plate.
4. Add ⅕ the total volume of the supernatant of magnetic bead reagent (50 µL/well maximum) to each sample and mix. Allow to sit for 5 minutes.
5. Place plate on top of magnetic particle concentrator for 5 minutes.
6. Remove supernatant and add to microcentrifuge tubes. Note: The supernatant contains isolated HDL. ApoB containing particles have been removed.
7. Centrifuge @ 5° C. @ 12,000 rpm for 5 minutes to remove any beads.
8. Remove supernatant.

Preparation of Buffers

1. Make coating buffer: 25 mL ddH$_2$O+8 mL Buffer A+17 mL Buffer B (Buffer A: 0.2M Na$_2$CO$_3$; Buffer B: 0.2M NaHCO$_3$.
2. Make wash buffer: 0.75 mL TWEEN®20+150 mL 10×PBS+1350 mL ddH$_2$O.
3. Make blocking/dilution buffer: 20 mL 10×PBS+10 mL TWEEN® 20+0.5 g BSA+170 mL ddH$_2$O.
4. Make stop solution: 1.38 mL H$_2$SO$_4$+48.62 mL H$_2$O.

Preparation of Samples and Standard Curve

1. Dilute samples (plasma or HDL supernatant) 1:200 into coating buffer (2.5 µL HDL into 497.5 µL coating buffer).
2. Make hemopexin in coating buffer at a concentration of 1000 ng/mL (2 µL hemopexin into 2 mL coating buffer).
3. Prepare triplicate standard points by serially diluting the 1000 ng/mL solution 1:2 with coating buffer to produce 500, 250, 125, 62.5, 31.25, 15.63 ng/mL solutions.
4. Include a well with only coating buffer for a blank.

Addition of Samples and Standards to Plate

1. Add 110 µL of each standard and each sample in triplicate to the round bottom 96 well, polypropylene plate.
2. Using a multi-channel pipet, remove 100 µL from each of the wells to add to the Immulon plate.
3. Incubate overnight at 4° C.
4. Flick antigen into biohazard waste container.
5. Wash three times with 300 µL of wash buffer. Invert the plate and decant the contents, and hit it 4-5 times on absorbent paper towel to completely remove liquid at each step.

Blocking and Primary Antibody

1. Add 200 µL of blocking buffer to all wells and incubate at room temperature for 1 hr.
2. Wash three times with 300 µL of wash buffer. Invert the plate and decant the contents, and hit it 4-5 times on absorbent paper towel to completely remove liquid at each step.
3. Dilute HRP Conjugated Chicken anti-Human Hemopexin 1:20000 (1 µL antibody in 20 mL dilution buffer).
4. Add 50 µL of 1:20000 dilution to each well
5. Wash three times with 300 µL of wash buffer. Invert the plate and decant the contents, and hit it 4-5 times on absorbent paper towel to completely remove liquid at each step.

Addition of TMB and Stop Solution
1. Mix one part TMB A with one part TMB B.
2. Add 100 μL of TMB mixture to each well and incubate for 20 minutes.
3. Add 100 μL of stop solution to each well.
Read in Plate Reader
1. Read in the plate reader at a wavelength of 450 nm.

ApoA-I Associated Immunoabsorbed Protein Hemoglobin ELISA

TABLE 4

Materials for ApoA-I Associated Immunoabsorbed Protein Hemoglobin ELISA.

| | Materials | Vendor | Catalog Number |
|---|---|---|---|
| 1 | HRP Conjugated Goat anti-Human Hemoglobin | Novus Biologicals | Ab19362 |
| 2 | Total Human Apolipoprotein A1 ELISA Kit | Alerchek | |
| 3 | Human Hemoglobin | Athens Research & Technology, Inc. | |
| 4 | Plate reader (e.g. VersaMax Tunable) | Molecular Devices | |
| 5 | Round bottom 96 well plate, polypropylene, non-sterile | Fisher | 12-565-502 |
| 6 | Immulon plates | Nunc | F25-034-03 |
| 7 | TMB | Fisher | |
| 8 | $H_2SO_4$ | Fisher | |

Note:
Bring all reagents to room temperature before use.

HDL Isolation with Magnetic Bead Reagent
1. Separate plasma or serum from blood sample using green top tube or serum separator tube and centrifuging @ 5° C. @ 2300 rpm for 20 minutes.
2. Remove supernatant (serum or plasma). Note: If sample is already frozen, thaw the sample and spin in centrifuge @ room temp. @ 12,000 rpm for 5 minutes. This should bring down any particles present in the serum or plasma that might affect the assay.
3. Add supernatant (250 μL/well maximum) to clear round bottom 96 well plate.
4. Add ⅕ the total volume of the supernatant of magnetic bead reagent (50 μL/well maximum) to each sample and mix. Allow to sit for 5 minutes.
5. Place plate on top of magnetic particle concentrator for 5 minutes.
6. Remove supernatant and add to microcentrifuge tubes. Note: The supernatant contains HDL. ApoB containing particles have been removed.
7. Centrifuge @ 5° C. @ 12,000 rpm for 5 minutes to remove any beads.
8. Remove supernatant.

Preparation of Buffers
1. Make coating buffer: 25 mL $ddH_2O$+8 mL Buffer A+17 mL Buffer B (Buffer A: 0.2M $Na_2CO_3$; Buffer B: 0.2M $NaHCO_3$.
2. Make wash buffer: 0.75 mL TWEEN® 20+150 mL 10×PBS+1350 mL $ddH_2O$.
3. Make blocking/dilution buffer: 20 mL 10×PBS+10 mL TWEEN® 20+0.5 g BSA+170 mL $ddH_2O$.
4. Make stop solution: 1.38 mL $H_2SO_4$+48.62 mL $H_2O$ Preparation of Samples and Standard Curve
1. Dilute samples (Serum or HDL supernatant) 1:200 into coating buffer (2.5 μL HDL into 497.5 μL coating buffer).
2. Make hemoglobin in coating buffer at a concentration of 1000 ng/mL (2 μL hemoglobin into 2 mL coating buffer).
3. Prepare triplicate standard points by serially diluting the 1000 ng/mL solution 1:2 with coating buffer to produce 500, 250, 125, 62.5, 31.25, 15.63 ng/mL solutions.
4. Include a well with only coating buffer for a blank.

Addition of Samples and Standards to Plate
1. Add 110 μL of each standard and each sample in triplicate to the round bottom 96 well, polypropylene plate.
2. Using a multi-channel pipet, remove 100 μL from each of the wells to add to the Anti-Human ApoA1 coated microwell plate (provided in A1 kit).
3. Incubate overnight at 4° C.
4. Flick antigen into biohazard waste container.
5. Wash three times with 300 μL of wash buffer. Invert the plate and decant the contents, and hit it 4-5 times on absorbent paper towel to completely remove liquid at each step.

Blocking and Primary Antibody
1. Add 200 μL of blocking buffer to all wells and incubate at room temperature for 1 hr.
2. Wash three times with 300 μL of wash buffer. Invert the plate and decant the contents, and hit it 4-5 times on absorbent paper towel to completely remove liquid at each step.
3. Dilute HRP Conjugated Goat anti-Human Hemoglobin 1:10000 (1 μL antibody in 10 mL dilution buffer).
4. Add 50 μL of 1:20000 dilutions to each well.
5. Wash three times with 300 μL of wash buffer. Invert the plate and decant the contents, and hit it 4-5 times on absorbent paper towel to completely remove liquid at each step.

Addition of TMB and Stop Solution
1. Mix one part TMB A with one part TMB B.
2. Add 100 μL of TMB mixture to each well and incubate for 20 minutes.
3. Add 100 μL of stop solution to each well.
Read in Plate Reader
1. Read in the plate reader at a wavelength of 450 nm.

ApoA-I Associated Immunoabsorbed Protein Haptoglobin ELISA

TABLE 5

Materials for ApoA-I Associated Immunoabsorbed Protein Haptoglobin ELISA.

| Materials | Vendor | Catalog Number |
|---|---|---|
| HRP Conjugated anti-Human Haptoglobin | Biogenesis | |
| Total Human Apolipoprotein A1 ELISA Kit | Alerchek | |
| Plate reader (e.g. VersaMax Tunable) | Molecular Devices | |
| Round bottom 96 well plate, polypropylene, non-sterile | Fisher | 12-565-502 |

Note:
Bring all reagents to room temperature before use.

HDL Isolation with Magnetic Bead Reagent
1. Separate plasma or serum from blood sample using green top tube or serum separator tube and centrifuging @ 5° C. @ 2300 rpm for 20 minutes.
2. Remove supernatant (serum or plasma). Note: If sample is already frozen, thaw the sample and spin in centrifuge @ room temp. @ 12,000 rpm for 5 minutes. This should bring down any particles present in the serum or plasma that might affect the assay.
3. Add supernatant (250 μL/well maximum) to clear round bottom 96 well plate.
4. Add ⅕ the total volume of the supernatant of magnetic bead reagent (50 μL/well maximum) to each sample and mix. Allow to sit for 5 minutes.

5. Place plate on top of magnetic particle concentrator for 5 minutes.

6. Remove supernatant and add to microcentrifuge tubes. Note: The supernatant contains isolated HDL. ApoB containing particles have been removed.

7. Centrifuge @ 5° C. @ 12,000 rpm for 5 minutes to remove any beads.

8. Remove supernatant.

Preparation of Buffers

1. Make coating buffer: 25 mL ddH$_2$O+8 mL Buffer A+17 mL Buffer B (Buffer A: 0.2M Na$_2$CO$_3$; Buffer B: 0.2M NaHCO$_3$.

2. Make wash buffer: 0.75 mL TWEEN® 20+150 mL 10×PBS+1350 mL ddH$_2$O.

3. Make blocking/dilution buffer: 20 mL 10×PBS+10 mL TWEEN® 20+0.5 g BSA+170 mL ddH$_2$O.

4. Make stop solution: 1.38 mL H$_2$SO$_4$+48.62 mL H$_2$O.

Preparation of HDL Supernatants

1. Dilute HDL supernatant 1:4000 into coating buffer.

2. Start by diluting 1:100 (5 μL HDL into 495 μL buffer).

3. Make 40-fold dilution of 1:100 (12.5 μL of 1:100 into 487.5 μL buffer).

Preparation of Standard Curve.

1. Reconstitute 100 μg of Haptoglobin Standard (provided in the kit) with 2 mL of buffer to make a concentration of 50 μg/mL.

2. Allow the standard to sit for 10 minutes with gentle agitation prior to making dilutions.

3. Prepare triplicate standard points by serially diluting the standard solution (50 μg/mL) 1:4 with buffer to produce 12.5, 3.13, 0.78, 0.195, and 0.049 μg/mL solutions.

Addition of Samples and Standards to Plate

1. Add 110 μL of each standard and each sample in triplicate to the round bottom 96 well, polypropylene plate.

2. Using a multi-channel pipet, remove 100 μL from each of the wells to add to the Anti-Human ApoA1 coated microwell plate (provided in A1 kit).

3. Incubate overnight at 4° C.

4. Flick antigen into biohazard waste container.

5. Wash three times with 300 μL of wash buffer. Invert the plate and decant the contents, and hit it 4-5 times on absorbent paper towel to completely remove liquid at each step.

Blocking and Primary Antibody

1. Add 200 μL of blocking buffer to all wells and incubate at room temperature for 1 hr.

2. Wash three times with 300 μL of wash buffer. Invert the plate and decant the contents, and hit it 4-5 times on absorbent paper towel to completely remove liquid at each step.

3. Dilute HRP Conjugated anti-Human Haptoglobin 1:20000 (1 μL antibody in 20 mL dilution buffer).

4. Add 50 μL of 1:20000 dilution to each well.

5. Wash three times with 300 μL of wash buffer. Invert the plate and decant the contents, and hit it 4-5 times on absorbent paper towel to completely remove liquid at each step.

Addition of TMB and Stop Solution

1. Mix one part TMB A with one part TMB B.

2. Add 100 μL of TMB mixture to each well and incubate for 20 minutes.

3. Add 100 μL of stop solution to each well.

Read in Plate Reader

1. Read in the plate reader at a wavelength of 450 nm.

ApoA-I Associated Immunoabsorbed Protein Hemopexin ELISA

TABLE 6

Materials for ApoA-I Associated Immunoabsorbed Protein Hemopexin ELISA.

| Materials | Vendor | Catalog Number |
| --- | --- | --- |
| HRP Conjugated Chicken anti-Human Hemopexin | Immunology Consultants Laboratory | CHX-80P |
| Total Human Apolipoprotein A1 ELISA Kit | Alerchek | |
| Hemopexin from Human Plasma | Athens Research & Technology, Inc. | |
| Plate reader (e.g. VersaMax Tunable) | Molecular Devices | |
| Round bottom 96 well plate, polypropylene, non-sterile | Fisher | 12-565-502 |
| Immulon plates | Nunc | F25-034-03 |
| TMB | Fisher | |
| H$_2$SO$_4$ | Fisher | |

Note:
Bring all reagents to room temperature before use.

HDL Isolation with Magnetic Bead Reagent

1. Separate plasma or serum from blood sample using green top tube or serum separator tube and centrifuging @ 5° C. @ 2300 rpm for 20 minutes.

2. Remove supernatant (serum or plasma). Note: If sample is already frozen, thaw the sample and spin in centrifuge @ room temp. @ 12,000 rpm for 5 minutes. This should bring down any particles present in the serum or plasma that might affect the assay.

3. Add supernatant (250 μL/well maximum) to clear round bottom 96 well plate.

4. Add ⅕ the total volume of the supernatant of magnetic bead reagent (50 μL/well maximum) to each sample and mix. Allow to sit for 5 minutes.

5. Place plate on top of magnetic particle concentrator for 5 minutes.

6. Remove supernatant and add to microcentrifuge tubes. Note: The supernatant contains isolated HDL. ApoB containing particles have been removed.

7. Centrifuge @ 5° C. @ 12,000 rpm for 5 minutes to remove any beads.

8. Remove supernatant.

Preparation of Buffers

1. Make coating buffer: 25 mL ddH$_2$O+8 mL Buffer A+17 mL Buffer B (Buffer A: 0.2M Na$_2$CO$_3$; Buffer B: 0.2M NaHCO$_3$.

2. Make wash buffer: 0.75 mL TWEEN® 20+150 mL 10×PBS+1350 mL ddH$_2$O.

3. Make blocking/dilution buffer: 20 mL 10×PBS+10 mL TWEEN® 20+0.5 g BSA+170 mL ddH$_2$O.

4. Make stop solution: 1.38 mL H$_2$SO$_4$+48.62 mL H$_2$O.

Preparation of Samples and Standard Curve

1. Dilute samples (HDL supernatant) 1:200 into coating buffer (2.5 μL HDL into 497.5 μL coating buffer).

2. Make hemopexin in coating buffer at a concentration of 1000 ng/mL (2 μL hemopexin into 2 mL coating buffer).

3. Prepare triplicate standard points by serially diluting the 1000 ng/mL solution 1:2 with coating buffer to produce 500, 250, 125, 62.5, 31.25, 15.63 ng/mL solutions.

4. Include a well with only coating buffer for a blank.

Addition of Samples and Standards to Plate

1. Add 110 μL of each standard and each sample in triplicate to the round bottom 96 well, polypropylene plate.

2. Using a multi-channel pipet, remove 100 µL from each of the wells to add to the Anti-Human ApoA1 coated microwell plate (provided in A1 kit).

3. Incubate overnight at 4° C.

4. Flick antigen into biohazard waste container.

5. Wash three times with 300 µL of wash buffer. Invert the plate and decant the contents, and hit it 4-5 times on absorbent paper towel to completely remove liquid at each step.

Blocking and Primary Antibody

1. Add 200 µL of blocking buffer to all wells and incubate at room temperature for 1 hr.

2. Wash three times with 300 µL of wash buffer. Invert the plate and decant the contents, and hit it 4-5 times on absorbent paper towel to completely remove liquid at each step.

3. Dilute HRP Conjugated Chicken anti-Human Hemopexin 1:20000 (1 µL antibody in 20 mL dilution buffer).

4. Add 50 µL of 1:20000 dilution to each well.

5. Wash three times with 300 µL of wash buffer. Invert the plate and decant the contents, and hit it 4-5 times on absorbent paper towel to completely remove liquid at each step.

Addition of TMB and Stop Solution

1. Mix one part TMB A with one part TMB B.

2. Add 100 µL of TMB mixture to each well and incubate for 20 minutes.

3. Add 100 µL of stop solution to each well.

Read in Plate Reader

1. Read in the plate reader at a wavelength of 450 nm.

It is noted that the protocols described herein are intended to be illustrative and not limiting. Using the teaching provided herein, other assays and assay formats will be readily available to one of skill in the art.

Results.

Figure 27:
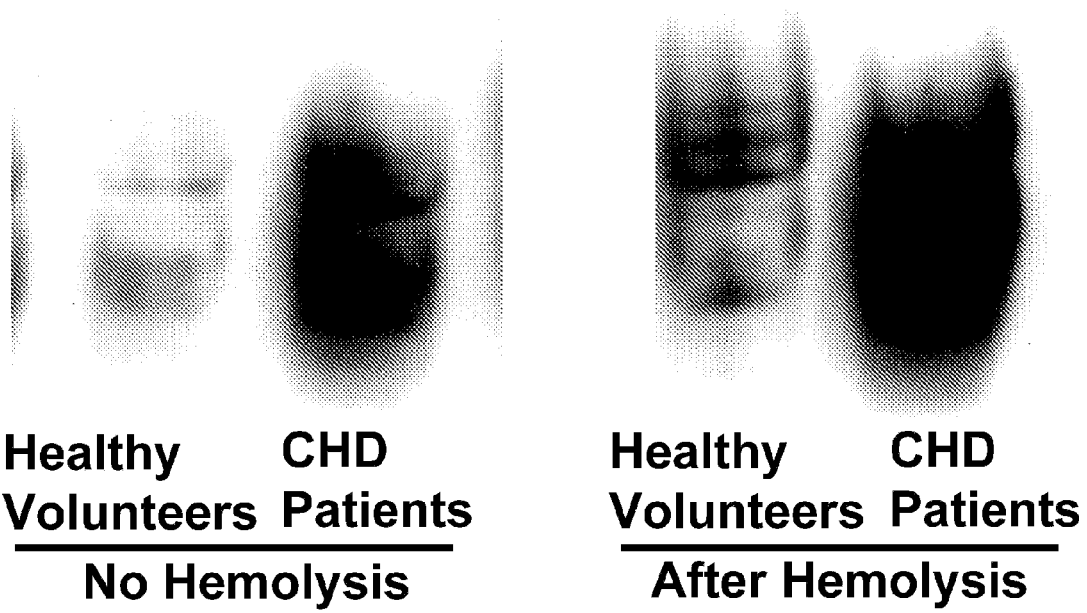
FIG. 27 compares hemoglobin in HDL from 10 healthy volunteers with 10 patients with coronary heart disease (CHD) or equivalent as defined by NCEP ATPIII guidelines. The left panel shows a native PAGE gel of the HDL fractions from plasma pooled from 10 healthy volunteers (left lane) or 10 CHD patients (right lane) that was immunoblotted for hemoglobin. The right panel shows the same analysis after RBC were lysed and the lysate added to the plasma prior to isolation of the HDL fractions. The results show that there was much more hemoglobin associated with HDL in the patients than in the healthy volunteers (left panel). The figure also demonstrates that addition of excess RBC hemoglobin to the plasma resulted in additional hemoglobin in the HDL fractions of both the healthy volunteers and the CHD patients but significantly more hemoglobin was still found in the HDL of the patients.

Plasma was pooled from 10 healthy volunteers and 10 patients with documented CHD. The HDL was isolated and run on Native PAGE gels and immunoblotted for hemoglobin using Western analysis. As shown in FIG. 27 in the left panel there was dramatically more hemoglobin found in the HDL from the 10 healthy volunteers compared to the 10 patients with CHD. As shown in the right panel of FIG. 27 addition of RBC lysate to the plasma prior to HDL isolation increased the amount of hemoglobin associated with HDL in both groups but a significant difference between the healthy volunteers and the CHD patients clearly remained even under these conditions of extreme hemolysis.

Figure 28A:
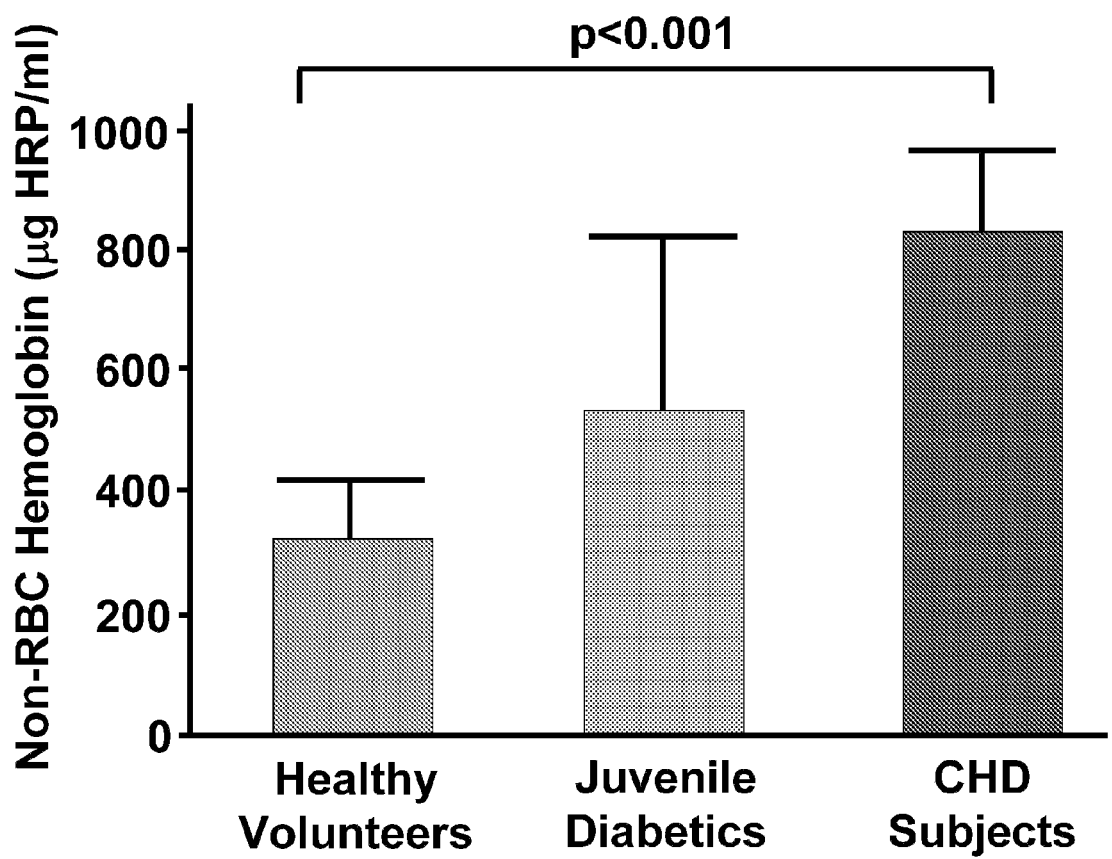
FIGS. 28A, 28B and 28C demonstrate that both non-RBC hemoglobin and haptoglobin are increased in HDL from juvenile diabetics and patients with CHD. Sera was collected from 12 healthy volunteers, 14 juvenile diabetics (8 adults; 6 children), or 8 subjects with CHD or CHD equivalents that were taking a statin. Antibody to human apoA-I was coated onto 96 well plates. The sera from the subjects was added and incubated overnight at 4 degrees centigrade. The plates were washed thoroughly and incubated overnight with primary goat antibody against human hemoglobin or human haptoglobin at 4 degrees centigrade. The plates were thoroughly washed and incubated with a secondary antibody to goat IgG conjugated to horseradish peroxidase (HRP) for 2 hours at room temperature. The plates were thoroughly washed and HRP substrate was added and optical density (OD) was measured.
Figure 28B:
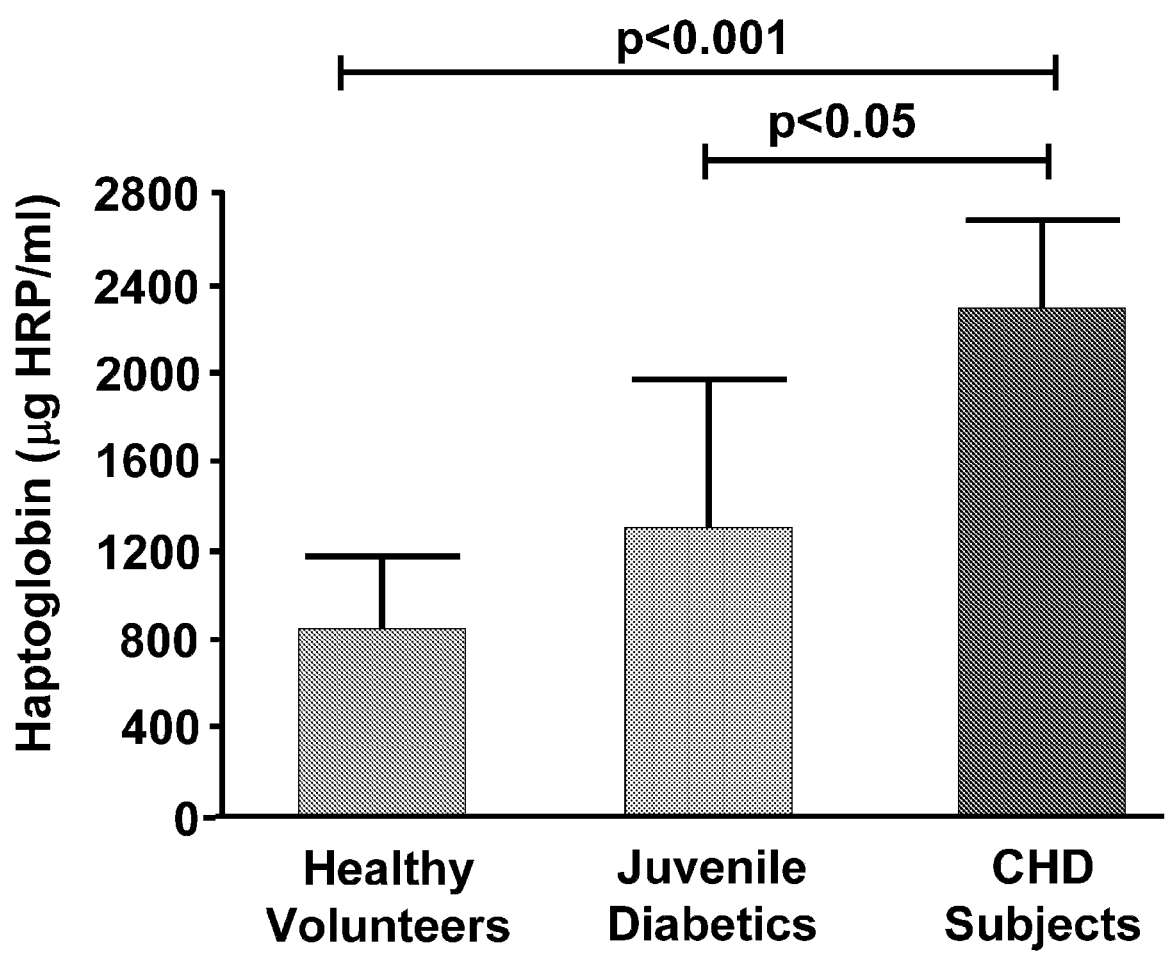
Figure 28C:
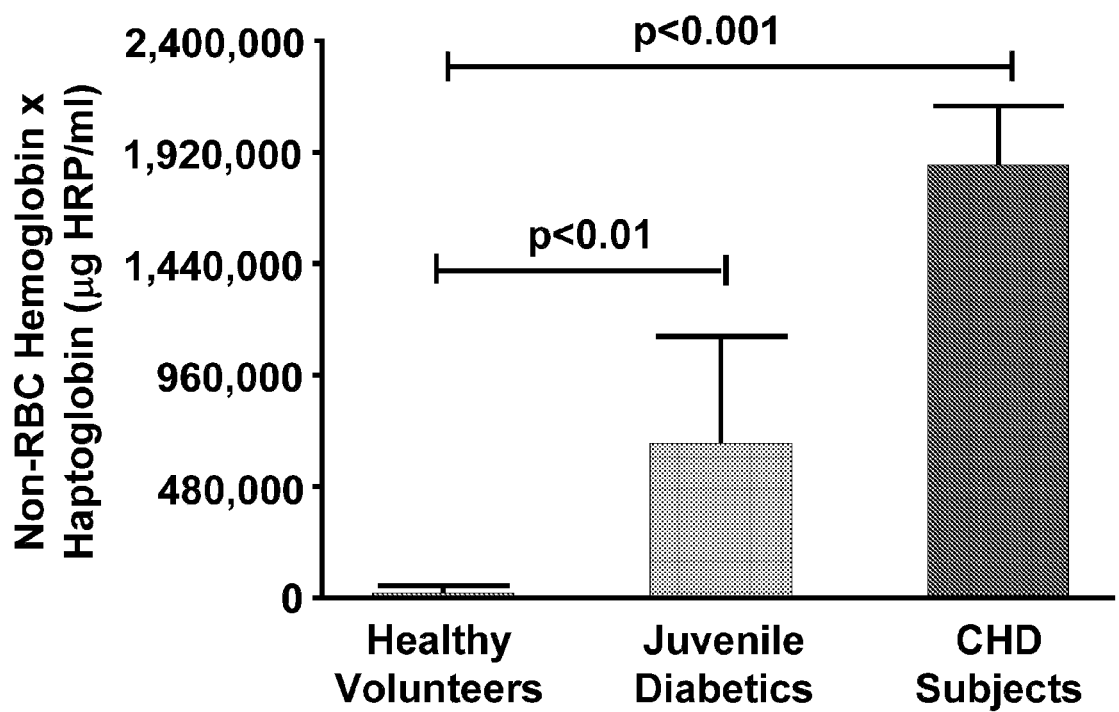

In other experiments sera was collected from another group of 12 healthy volunteers and from 14 juvenile diabetics (8 adults and 6 children, and from 8 subjects with CHD or equivalents by NCEP ATP III criteria. All of the latter patients were taking a statin. Antibody to human apoA-I was coated onto 96 well plates. The sera from the subjects was added and incubated overnight at 4° C. The plates were washed thoroughly and incubated overnight with primary goat antibody against human hemoglobin or human haptoglobin at 4° C. The plates were thoroughly washed and incubated with a secondary antibody to goat IgG conjugated to horse radish peroxidase (HRP) for 2 hours at room temperature. The plates were thoroughly washed and HRP substrate was added and optical density (OD) was measured. FIG. 28A shows the non-RBC hemoglobin in micrograms HRP/mL. FIG. 28B shows haptoglobin in micrograms HRP/mL. FIG. 28C shows the product of the non-RBC hemoglobin values multiplied by the haptoglobin values. The results indicate that the obtained values for the latter method separated the healthy volunteers from the diabetics and the CHD patients without any overlap.

These results indicate that the novel assays reported here are useful in detecting subjects with diseases such as diabetes and CHD and provide a means for differentiating them from normal persons.

Example 2

Protein Profiles in Pro-Inflammatory HDL

We have reported that the inflammatory properties of HDL are a more sensitive indicator of atherosclerosis than HDL-cholesterol levels, in both mice and humans. In this example, we describe the identification of specific protein fingerprints that distinguish normal mouse HDL from mouse HDL on atherogenic diets, using ProteinChip technology coupled with surface-enhanced laser desorption/ionization time-of-flight mass spectrometry (SELDI-TOF-MS). Feeding C57BL/6J mice an atherogenic diet for one week resulted in lower HDL-cholesterol levels, reduced paraoxonase activity, increased reactive oxygen species content and reduced ability of the HDL to promote cholesterol efflux from macrophages. When the mice were switched back to a chow diet for an additional 2 weeks, the pro-atherogenic characteristics of HDL reverted to the normal phenotype. We identified a total of 88 SELDI peaks with $p<0.05$ to be differentially present in pro-inflammatory HDL from mice fed an atherogenic diet compared to normal HDL from mice fed a chow diet. 74 of the 88 serum peaks reverted to normal levels upon diet reversal. Following further analyses to eliminate artifacts/changes arising from short-term dietary changes and non-atherogenic factors, we identified 24 SELDI m/z peaks representing proteins that are differentially associated with pro-inflammatory HDL. Fourteen of the 24 protein peaks were found common to pro-inflammatory HDL from three other widely used animal models of atherosclerosis/hyperlipidemia; C57BL/6J on western diet, LDLR null and apoE null mice. Furthermore, protein profiling of serum samples from all four animal models identified an eight-protein core signature (a subset of the 14 SELDI m/z peaks described above) that can be used as a serum biomarker panel for identifying pro-inflammatory HDL.

Experimental Procedures

Animal Experiments.

C57BL/6J, LDLR null/C57BL/6J and apoE null/C57BL/6J female mice age of 8-12 weeks were used in these experiments. Mice were fed one of three diets for the periods described: chow diet (Ralston Purina Mouse Chow), or atherogenic diet containing 15.8% fat, 1.25% cholesterol, and 0.5% cholic acid) w/w/w, (Teklad/Harlan Catalog), or a western diet (Teklad/Harlan, Madison Wis., diet No. 88137; 42% fat, 0.15% cholesterol, w/w). Serum samples were isolated from overnight fasted mice, cryopreserved in 10% sucrose as described previously (Navab et al. (2000) *J. Lipid Res.*, 41: 1481-1494) and were stored at −80° C. until use.

Lipoprotein Isolation.

Serum samples were fractionated by a gel permeation fast performance liquid chromatography (FPLC) system consisting of dual Pharmacia Superose 6 columns in series. Serum (0.5 ml) was eluted with sterile PBS at a flow rate of 0.5 ml/min pumped by a non-metallic Beckman HPLC pump and fractionated for every 1 ml. Each fraction was assayed for cholesterol content using cholesterol reagent (Thermo, Louisville, Colo.) and for protein content using BCA assay (Promega, Madison, Wis.) according to the manufacturer's protocol.

HDL Isolation for SELDI Analysis and Ex Vivo Assays.

HDL was freshly isolated with LipiDirect HDL reagent (Polymedco, Cortland Manor, N.Y.) according to the manufacturer's protocol. The supernatant containing HDL was assayed for cholesterol content and BCA protein assays and used within 48 hours after isolation.

Reactive Oxygen Species (ROS) in HDL.

ROS content in HDL was determined with 2,7,7'dicholrofluorescein diacetate ($H_2$DCFDA: Invitrogen, Carlsbad, Calif.) as described previously (Navab et al. (2001) *J. Lipid Res.*, 42: 1308-1317). Briefly, HDL was incubated with $H_2$DCFDA (10 μg/ml) in methanol for 30 min at 37° C. The DCF formation as an indicator of ROS was detected by measuring fluorescence intensity at 485 nm/525 nm.

Paraoxonase (PON) Assay.

PON activity in HDL was determined as described previously (Van Lenten et al. (1995) *J. Clin. Invest.*, 96: 2758-2767). HDL was incubated with paraoxon and PON activity was analyzed by measuring the increase in absorbance at 405 nm over a period of 12 minutes. A unit of PON activity was defined as the formation of 1 nmol of 4-ntriophenol per minute per ml of HDL applied.

Cholesterol Efflux.

Cellular cholesterol efflux was performed as described previously (Navab et al. (2004) *Circulation*, 109: 3215-3220). Briefly, mouse RAW264.7 cells were cultured on 24-well tissue culture plates and grown in DMEM media with 10% FBS for overnight. Cells were washed with serum free media and loaded with $^3$H-cholesterol (0.5 μCi/ml) and acetylated LDL (50 μg/ml) in media with 0.5% fatty acid free BSA (Sigma, St. Louis, Mo.) overnight. Labeled cells were washed, resuspended in media with 0.5% BSA and incubated with HDL for 6 hours at 37° C. Cholesterol efflux was expressed as the percentage of total radioactive counts released to the medium.

Sample Preparation for SELDI Analysis.

Serum and HDL samples were processed on strong anion-exchange (Q10) chips according to the manufacturer's protocols (Ciphergen Biosystems, Fremont, Calif.). Briefly, the Q10 array spots were equilibrated with binding buffer (1×PBS/0.1% TRITON® X-100, pH 7) at room temperature for 15 mm in a humidifying chamber. Each sample was first diluted at 1:5 with 9 M urea/2% Chaps/50 mM Tris.HCl, pH 9.0, and further diluted to 1:25 with binding buffer. Five microliters of each diluted sample was spotted onto equilibrated Q10 protein away chips and incubated in a humidity chamber for 30 mm at room temperature. The chips were washed twice with binding buffer and once with HPLC $H_2O$, and then air-dried. The chips were sequentially treated with sinapinic acid solution, first with 0.5 μl of a 100% saturated solution followed by 1 μl of a 50% saturated solution. The sinapinic acid solution is freshly prepared by saturating EAM solution (50% acetonitrile and 0.5% trifluoroacetic acid) with sinapinic acid (3,5-dimethoxy-4-hydroxycinnamic acid).

Ciphergen ProteinChip SELDI-TOF-MS Analysis.

The arrays were analyzed with the Ciphergen ProteinChip Reader (model PB SII). The mass spectra of proteins were generated by using an average of 65 laser shots at a laser intensity of 230-280 arbitrary units. For data acquisition of low molecular weight proteins, the detection size range was set between 2 and 18 kDa, with a maximum size of 25 kDa. For the high molecular weight proteins, the detection size range was set between 20 and 150 kDa, with a maximum size of 250 kDa. The mass-to-charge ratio (m/z) of each of the proteins captured on the array surface was determined according to externally calibrated standards (Ciphergen Biosystems): bovine insulin (5,733.6 Da), human ubiquitin (8,564.8 Da), bovine cytochrome c (12,230.9 Da), bovine superoxide dismutase (15,591.4 Da), bovine-lactoglobulin A (18,363.3 Da), horseradish peroxidase (43,240 Da), BSA (66, 410 Da), and chicken conalbumin (77,490 Da).

Statistical Analysis.

The data were analyzed with ProteinChip data analysis software version 3.2 (Ciphergen Biosystems). For each comparison, the raw intensity data was normalized by using the total ion current of all profiles in the groups. The peak intensities were normalized to the total ion current of m/z between 3,000 and 25,000 Da for the low molecular weight range and between 4,000 and 250,000 Da for the high molecular weight range. The Biomarker Wizard application (nonparametric calculations; Ciphergen Biosystems) was used to compile all spectra and autodetect quantified mass peaks. Sample statistics were performed on groups of profiles (anti-inflammatory HDL vs. pro-inflammatory HDL; normal serum vs. atherogenic serum). Protein differences (fold changes) were calculated among the various groups. A protein was considered differentially associated between two groups if, when compared with the one group, statistically significant differences in its intensity were observed ($p<0.05$).

Results

Model System.

Figure 18:
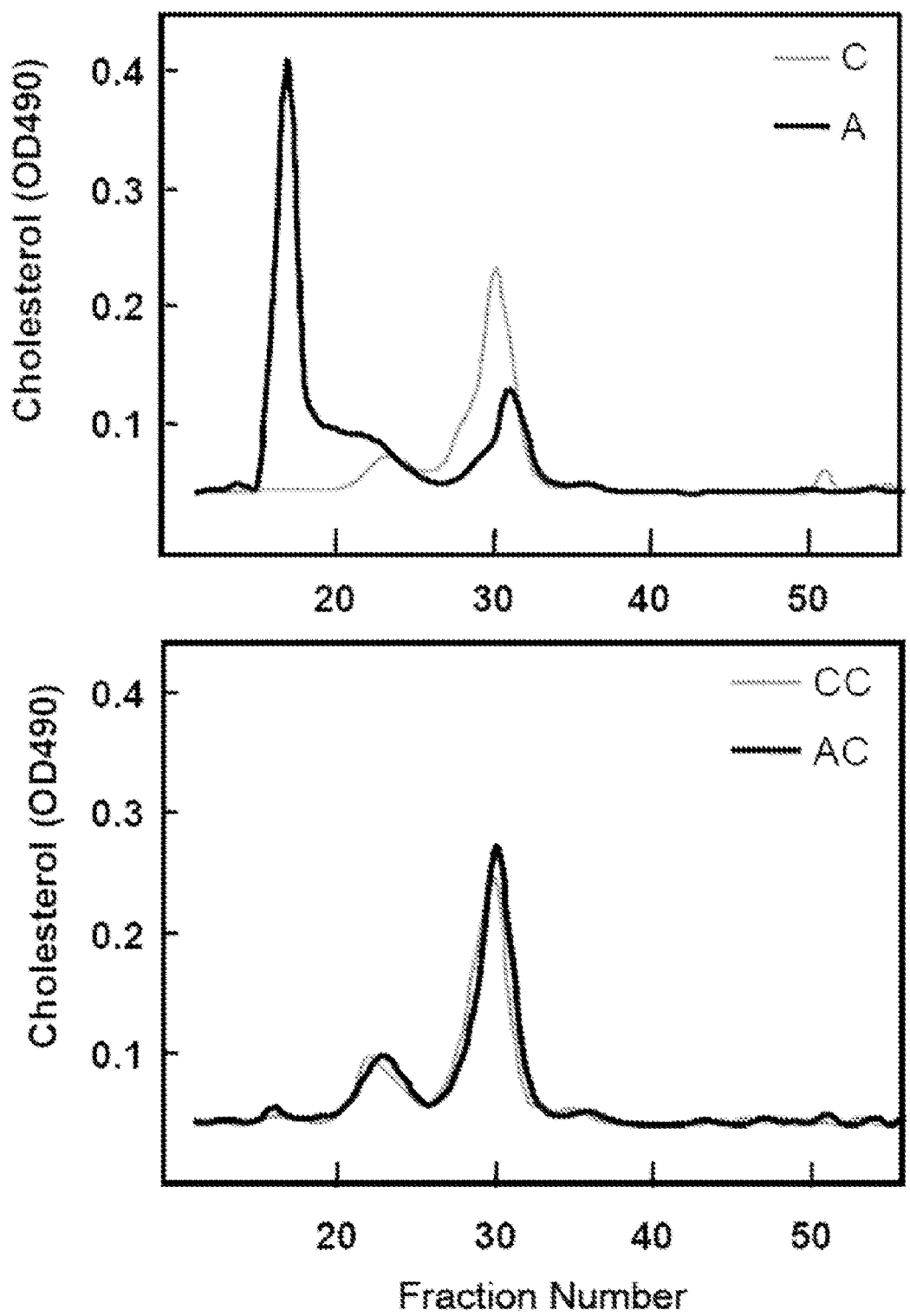
FIG. 18 shows the cholesterol profile of C57BL/6J mouse serum samples following FPLC fractionation. 500 µl of pooled serum from mice (n=8) were fractionated by FPLC. The first ten 1 mL fractions were discarded and each subsequent 1 mL was analyzed for cholesterol content. C—chow fed for 7 days, A—atherogenic diet for 7 days, CC—chow fed for 21 days, AC—atherogenic diet for 7 days followed by chow for 14 days.
Figure 19:
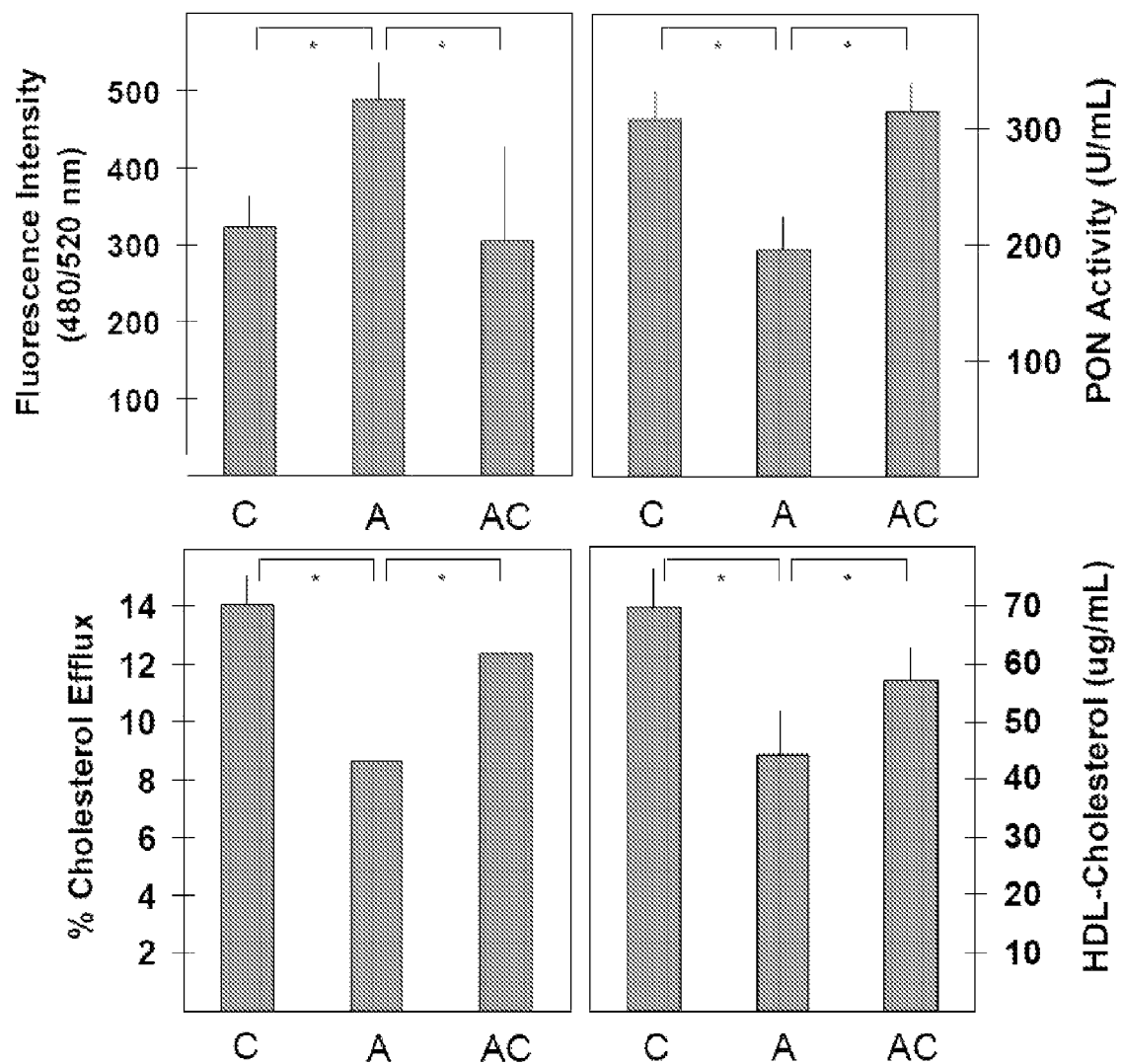
FIG. 19 shows the inflammatory properties of HDL from C57BL/6J mouse serum. HDL were isolated with HDL reagent and analyzed for reactive oxygen species content (fluorescence intensity), paroxynase (PON) activity assay, cholesterol efflux assay (% cholesterol efflux), and cholesterol content (HDL-cholesterol). C—chow fed for 7 days, A—atherogenic diet for 7 days, AC—atherogenic diet for 7 days followed by chow for 14 days. * represents p<0.01.

Hedrick et al showed that short-term feeding (up to 7 days) of an atherogenic diet to C57BL/6J low density lipoprotein receptor-deficient (LDLR null) mice causes a dramatic decrease in plasma PON activity and mass and an increase in plasma and HDL lipid hydroperoxides (Hedrick et al. (2000) *Arterioscler. Thromb. Vasc. Biol.*, 20: 1946-1952). Interestingly, after mice consumed an atherogenic diet for 7 days, switching to the chow diet for 3 days, resulted in the return to normal levels of PON mass and activity. However, Hedrick et al noted that the switch to chow diet for 3 days did not result in a complete recovery of all HDL properties (Id.). In our pursuit to identify the differentially associated proteins in pro-inflammatory HDL, we utilized a similar mouse model system. C57BL/6J mice fed normal chow have anti-inflammatory HDL, whereas C57BL/6J mice fed an atherogenic diet have pro-inflammatory HDL (Shih et al. (1996) *J. Clin. Invest.*, 97: 1630-1639). As shown in FIGS. 18 and 19 when the diet is changed at 7 days from atherogenic to normal chow for an additional 14 days HDL cholesterol (FIG. 18 and FIG. 19, lower right), reactive oxygen species content (FIG. 19, top left), PON activity (FIG. 19, top right), and HDL-mediated cholesterol efflux (FIG. 19, lower left), were restored to normal levels. We reasoned that the use of HDL from these three experimental conditions (normal chow for the entire experimental period which in some experiments was up to 21 days, atherogenic diet for the entire experimental period which in some experiments was up to 21 days, or atherogenic diet for seven days followed by normal chow for an additional 14 days) would provide a system to identify the proteins that are associated or dissociated from HDL when HDL converts to a pro-inflammatory state.

Specific SELDI Peaks are Differentially Associated with Pro-Inflammatory HDL.

We first utilized SELDI analysis to identify proteins that are differentially associated with HDL on the atherogenic diet. Eight-week old female C57BL/6J mice (n=8 per group) were fed either normal chow for 7 days (C), atherogenic diet for 7 days (A), normal chow for 21 days (CC), or atherogenic diet for 7 days followed by normal chow (AC) for another 14 days. Serum samples (obtained following overnight fasting)

from each diet group were collected at the end of each period. HDL from each serum was isolated with LipiDirect HDL reagent and subjected to SELDI analysis to identify protein profiles in atherogenic serum and HDL from mice on the atherogenic diet compared with serum and HDL from mice that received normal chow. Protein profiles were obtained from individual serum samples (n=8) from each group. Protein profiles in 'C' group were compared to protein profiles in the 'A' group and protein profiles in the 'CC' group were compared to protein profiles in the 'AC' group. In the first set of analyses the m/z peaks differentially detected in HDL from atherogenic serum ('A' group) compared to HDL from normal serum ('C' groups), were further statistically analyzed by Ciphergen ProteinChip software as described previously (Kozak et al. (2003) *Proc. Natl. Acad. Sci., USA*, 100: 12343-12348). A total of 88 peaks were detected in HDL from mice on the atherogenic diet for 21 days that was significantly different from HDL from mice on the chow diet for 21 days ($p<0.05$).

Protein Peaks in HDL Reflect the Change in Diet.

When these protein profiles were analyzed against the 'AC' group, 74 of the 88 peaks reverted back to the normal levels seen in HDL on the chow diet suggesting that these peaks represent protein profiles associated with the conversion of HDL from anti-inflammatory to pro-inflammatory and vice versa (Table 12).

Common Protein Profiles are Present in both Short-Term and Long-Term Diet-Induced Pro-Inflammatory HDL.

SELDI profiles were also generated by comparing HDL in atherogenic serum from C57BL/6J mice (n=8) fed an atherogenic diet for 15 weeks (W15A) to HDL in serum from mice fed normal chow for 15 weeks (W15C). We further determined the peaks that were common in the short-term diet-induced HDL (74 peaks described above) and the long-term diet-induced (15-week) HDL. We reasoned that this comparison would eliminate artifacts/changes arising from short-term dietary changes. We identified a total of 24 SELDI peaks that were specific and significantly different in HDL from mice that received the atherogenic diet for any period (7-day atherogenic diet as well as 15-week atherogenic diet) when compared to HDL from mice fed the chow diet (Table 7).

TABLE 7

Common SELDI peaks associated with HDL after feeding the atherogenic diet either short-term or long-term.

| Protein Peaks | Fold change in protein peaks obtained by comparing: | | |
|---|---|---|---|
| m/z (×10³) | A to C | AC to CC | W15A to W15C |
| 5.1 | (1.4) | 3.1 | (1.9) |
| 6.2 | 1.6 | NC | 2.4 |
| 6.9 | (1.8) | NC | (3.0) |
| 7.4 | 2.5 | NC | 5.5 |
| 7.8 | 1.9 | NC | 3.4 |
| 9.3 | (2.4) | NC | (2.1) |
| 12.7 | 2.9 | NC | 1.5 |
| 14.9 | 5.9 | NC | 8.8 |
| 15.1 | 6.8 | NC | 7.9 |
| 15.6 | 4.7 | 3.5 | 8.1 |
| 15.8 | 5.0 | NC | 6.1 |
| 15.9 | 4.8 | NC | 7.5 |
| 16.2 | 4.0 | NC | 5.3 |
| 16.5 | 3.2 | 1.8 | 3.8 |
| 18.6 | (3.1) | (1.5) | (3.5) |
| 19.5 | (3.3) | (2.4) | (1.8) |
| 22.0 | (1.3) | 1.6 | (1.6) |
| 35.3 | 1.5 | NC | 1.1 |
| 73.3 | (1.5) | NC | (1.7) |
| 76.9 | 1.9 | NC | 6.3 |
| 81.0 | 2.6 | NC | 2.5 |
| 131.5 | (1.5) | NC | (1.4) |
| 163.7 | (2.1) | (1.3) | (1.6) |
| 196.8 | (1.8) | NC | (1.8) |

Numbers in parentheses represent protein peaks with a decrease in fold-change.
NC = No Change,
C = 7 days on a chow diet,
A = 7 days on an atherogenic Diet,
AC = 7 days on atherogenic diet followed by an additional 14 days on a chow diet,
CC = 21 days on a chow diet.
15wA = 15 weeks on an atherogenic diet,
15wC = 15 weeks on a chow diet.

Since the atherogenic diet contains 0.5% cholic acid we repeated all of the experiments described above on HDL from serum samples obtained from mice (n=8) fed a western diet (WD), which does not contain cholic acid, and identified a protein signature consisting of 21 m/z peaks representing proteins that are differentially associated with HDL on both high-fat high-cholesterol diets (both the atherogenic diet with cholic acid and the western diet which does not contain cholic acid) (Table 8). There were 13 protein peaks that strongly associated/increased with HDL from mice fed the atherogenic or western diets (numbers in black), and 8 proteins (in parenthesis) that dissociated/decreased in HDL from mice fed the atherogenic or western diets when compared to HDL from mice fed a chow diet (Table 8).

TABLE 8

Common SELDI peaks differentially associated with C57BL/6J HDL from western diet-fed and atherogenic diet-fed mice.

| Protein Peaks | Fold change in protein peaks obtained by comparing | | | |
|---|---|---|---|---|
| m/z (×10³) | A | AC to CC | W15A to W15C | WD to C |
| 6.2 | 1.6 | NC | 2.4 | 2.3 |
| 6.9 | (1.8) | NC | (3.0) | (1.6) |
| 7.4 | 2.5 | NC | 5.5 | 3.9 |
| 7.8 | 1.9 | NC | 3.4 | 2.7 |
| 9.3 | (2.4) | NC | (2.1) | (1.5) |
| 12.7 | 2.9 | NC | 1.5 | 1.9 |
| 14.9 | 5.9 | NC | 8.8 | 1.8 |
| 15.1 | 6.8 | NC | 7.9 | 4.3 |
| 15.6 | 4.7 | NC | 8.1 | 5.0 |
| 15.8 | 5.0 | NC | 6.1 | 4.6 |
| 15.9 | 4.8 | NC | 7.5 | 7.1 |
| 16.2 | 4.0 | NC | 5.3 | 5.1 |
| 16.5 | 3.2 | 1.8 | 3.8 | 3.1 |
| 18.6 | (3.1) | (1.5) | (3.5) | (1.8) |
| 19.5 | (3.3) | (2.4) | (1.8) | (3.0) |
| 22.0 | (1.3) | 1.6 | (1.6) | (1.8) |
| 73.3 | (1.5) | NC | (1.7) | (1.8) |
| 76.9 | 1.9 | NC | 6.3 | 12.7 |
| 81.0 | 2.6 | NC | 2.5 | 4.7 |

TABLE 8-continued

Common SELDI peaks differentially associated with C57BL/6J
HDL from western diet-fed and atherogenic diet-fed mice.

| Protein Peaks | Fold change in protein peaks obtained by comparing | | | |
|---|---|---|---|---|
| m/z (×10³) | A | AC to CC | W15A to W15C | WD to C |
| 131.5 | (1.5) | NC | (1.4) | (1.7) |
| 163.7 | (2.1) | (1.3) | (1.6) | (1.3) |

Numbers in parentheses represent peaks with a decrease in fold-change.
NC = No Change,
C = 7 days on a chow diet,
A = 7 days on an atherogenic Diet,
AC = 7 days on atherogenic diet followed by an additional 14 days on a chow diet,
CC = 21 days on a chow diet.
15wA = 15 weeks on an atherogenic diet,
15wC = 15 weeks on a chow diet,
WD = 7 days on a western diet Common Protein Profiles Differentially Associated with HDL in Hyperlipidemic Mouse Models.

To validate the identified protein profiles that distinguish HDL from mouse models of atherosclerosis from HDL from control mice, we further utilized other well-known mouse models of atherosclerosis including LDLR null mice fed a western diet and apoE null mice fed a chow diet. These mice are susceptible to atherosclerosis and have pro-inflammatory HDL (Navab et al. (2005) *Ann. Med.*, 37: 173-178; Shih et al. (1996) *J. Clin. Invest.*, 97: 1630-1639; Ridker (2002) *Circulation*, 105: 2-4). HDL samples from these atherogenic mice were subjected to SELDI analysis and the profiles were cross validated with the C57BL/6J mouse models. These studies not only eliminated artifacts/changes caused by short-term dietary changes and non-atherogenic factors, but also identified common biomarkers of HDL in multiple atherogenic models. Fourteen of the 21 peaks identified in C57BL/6J mouse models associated with pro-inflammatory HDL were common to those detected in HDL from LDLR null and apoE null mice (Table 9).

TABLE 9

Common SELDI peaks differentially associated with HDL from
three mouse models of atherosclerosis.

| Protein Peaks | Fold change in protein peaks obtained by comparing: | | |
|---|---|---|---|
| m/z (×10³) | WT | LDLR | ApoE |
| 7.4 | 2.5 | 5.2 | 2.2 |
| 7.8 | 1.9 | 2.9 | 1.9 |
| 9.3 | (2.4) | (2.4) | (2.1) |
| 14.9 | 5.9 | 2.0 | 3.2 |
| 15.1 | 6.8 | 2.8 | 3.2 |
| 15.6 | 4.7 | 4.1 | 4.4 |
| 15.8 | 5.0 | 2.7 | 3.5 |
| 15.9 | 4.8 | 2.3 | 3.1 |
| 16.2 | 4.0 | 2.8 | 4.2 |
| 16.5 | 3.2 | 3.5 | 4.0 |
| 18.6 | (3.1) | (3.2) | (2.2) |
| 19.5 | (3.3) | (2.2) | (2.4) |
| 81.0 | 2.6 | 3.1 | 2.5 |
| 163.7 | (2.1) | (2.2) | (1.7) |

Numbers in parentheses represent protein peaks with a decrease in fold-change.
WT = m/z peaks differentially associated with pro-inflammatory HDL in wild-type C57BL/6J mice,
LDLR = m/z peaks associated with pro-inflammatory HDL from LDLR null mice,
ApoE = m/z peaks associated with pro-inflammatory HDL from ApoE null mice.

Potential Serum Biomarkers Associated with Pro-Inflammatory HDL.

To further identify serum protein profiles that represent proteins associated with HDL on the atherogenic/hyperlipidemic diets, serum samples from all four mouse atherosclerosis models were subjected to SELDI analysis in the same manner as performed for HDL. SELDI analysis identified 13 peaks as the common biomarkers in atherogenic/hyperlipidemic mouse serum (Table 10). Furthermore, 8 of the 13 protein peaks detected in atherogenic/hyperlipidemic serum were common to those identified in HDL on the atherogenic/hyperlipidemic diets (14 peaks above) (Table 11). These imply that the identified 8 proteins are potential biomarkers associated with pro-inflammatory HDL that can be detected directly in mouse serum.

TABLE 10

Common SELDI peaks differentially associated with serum from
three mouse models of atherosclerosis.

| Protein Peaks | Fold change in protein peaks obtained by comparing: | | |
|---|---|---|---|
| m/z (×10³) | WT | LDLR | ApoE |
| 9.3 | (2.5) | (3.8) | (1.9) |
| 11.6 | (1.9) | (2.7) | (4.2) |
| 14.7 | 8.8 | 2.9 | 3.7 |
| 14.9 | 13.2 | 3.7 | 5.2 |
| 15.3 | 18.0 | 2.4 | 3.3 |
| 15.6 | 16.6 | 2.0 | 3.3 |
| 15.8 | 14.4 | 5.8 | 3.9 |
| 16.2 | 7.7 | 3.0 | 8.6 |
| 16.5 | 5.8 | 2.1 | 3.7 |
| 18.6 | (4.9) | (5.5) | (3.3) |
| 19.5 | (3.5) | (4.1) | (3.0) |
| 34.0 | 1.2 | 2.2 | 1.2 |
| 90.0 | (1.4) | (2.1) | (2.3) |

Numbers in parentheses represent protein peaks with a decrease in fold-change.
WT = m/z peaks differentially associated with atherogenic serum in wild-type C57BL/6J mice,
LDLR = m/z peaks associated with atherogenic/hyperlipidemic serum from LDLR null mice,
ApoE = m/z peaks associated with atherogenic serum from ApoE null mice.

TABLE 11

Common protein signature that is differentially associated with
HDL and serum in three C57BL/6J mouse models of atherosclerosis.

| m/z (×10³) | (9.3) | 14.9 | 15.6 | 15.8 | 16.2 | 16.5 | (18.6) | (19.5) |
|---|---|---|---|---|---|---|---|---|

Discussion

In recent years, it has become clear that HDL function may be a more selective therapeutic target than HDL-C, in the fight against atherosclerosis (Castellani et al. (1997) *J. Clin. Invest.*, 100: 464-474; Navab et al. (2005) *Ann. Med.*, 37: 173-178; Ridker (2002) *Circulation*, 105: 2-4; Ansell et al. (2003) *Circulation*, 108: 2751-2756). Although a number of proteins and enzyme activities are associated with HDL, very little is known of which particular protein profiles help to better distinguish normal/anti-inflammatory HDL from pro-inflammatory HDL. We have utilized ProteinChip technology in established mouse models of atherosclerosis and identified m/z peaks representing proteins that are differentially associated with HDL in mice on atherogenic diets.

All of our experiments were performed on individual mouse samples (n=8 per each group) and each sample was measured in triplicate. Moreover, only m/z peaks that were significant between groups (p<0.05) were accepted as candidate peaks for further analysis. In the first set of experiments, a total of 74 m/z peaks in HDL (Table 12) reverted to normal levels when the diet was changed from an atherogenic diet (7 days) to chow diet for an additional 14 days. To eliminate any artifacts due to short-term changes in diet these peaks were further compared against protein profiles obtained from HDL samples from mice fed an atherogenic diet for 15 weeks. Interestingly, only 24 (Table 7) of the original 74 peaks that were represented in HDL obtained from mice fed an atherogenic diet for 15 weeks suggesting that the remaining 59 m/z peaks may be due to short-term dietary changes and/or non-atherogenic factors. However, it is also possible that the remaining 59 m/z peaks still represent proteins that are associated with pro-inflammatory HDL in the early stages of atherogenic transformation of HDL.

TABLE 12

SELDI peaks associated with pro-inflammatory HDL from C57BL/6J mice.

| Protein Peaks | Fold change in peaks obtained by comparing: | |
|---|---|---|
| m/z (×10$^3$) | A to C | AA to CC |
| 5.1 | (1.4) | 3.1 |
| 5.3 | (1.8) | 4.0 |
| 5.4 | (1.7) | 2.2 |
| 5.5 | (1.9) | NC |
| 5.7 | (1.8) | 1.7 |
| 6.0 | (2.2) | 2.2 |
| 6.2 | 1.6 | NC |
| 6.5 | (2.1) | 3.0 |
| 6.9 | (1.8) | NC |
| 7.1 | (1.5) | NC |
| 7.2 | (1.8) | 2.3 |
| 7.3 | (1.6) | NC |
| 7.4 | 2.5 | NC |
| 7.8 | 1.9 | NC |
| 7.9 | (1.2) | 2.3 |
| 8.4 | (1.9) | 1.9 |
| 8.8 | (1.6) | (3.9) |
| 8.9 | (2.3) | 1.8 |
| 9.3 | (2.4) | NC |
| 10.3 | (4.2) | NC |
| 11.6 | (2.1) | 1.6 |
| 12.4 | 2.2 | NC |
| 12.7 | 2.9 | NC |
| 13.5 | (1.5) | NC |
| 13.7 | 1.6 | NC |
| 14.7 | 2.6 | (1.9) |
| 14.9 | 5.9 | NC |
| 15.1 | 6.8 | NC |
| 15.6 | 4.7 | NC |
| 15.8 | 5.0 | NC |
| 15.9 | 4.8 | NC |
| 16.2 | 4.0 | NC |
| 16.5 | 3.2 | 1.8 |
| 17.6 | (2.2) | 2.8 |
| 18.6 | (3.1) | (1.5) |
| 19.5 | (3.3) | (2.4) |
| 21.2 | (1.6) | 1.6 |
| 22.0 | (1.3) | 1.6 |
| 23.9 | (1.5) | 1.5 |
| 24.8 | (2.8) | NC |
| 25.7 | (1.5) | 2.0 |
| 28.0 | (1.9) | 2.2 |
| 35.3 | 1.5 | NC |
| 36.5 | 1.8 | NC |
| 38.7 | 2.4 | NC |
| 40.8 | 3.0 | NC |
| 43.2 | (1.4) | 1.7 |
| 44.3 | (1.6) | NC |
| 45.2 | (1.7) | NC |
| 46.0 | (8.7) | 1.9 |
| 47.4 | (3.7) | NC |

TABLE 12-continued

SELDI peaks associated with pro-inflammatory HDL from C57BL/6J mice.

| Protein Peaks | Fold change in peaks obtained by comparing: | |
|---|---|---|
| m/z (×10$^3$) | A to C | AA to CC |
| 49.6 | (2.5) | (1.30) |
| 53.4 | (1.8) | NC |
| 65.9 | 1.2 | NC |
| 73.3 | (1.5) | NC |
| 76.9 | 1.9 | NC |
| 81.0 | 2.6 | NC |
| 85.1 | (3.2) | NC |
| 88.2 | (1.9) | NC |
| 98.8 | (1.8) | NC |
| 106.6 | 3.3 | (1.9) |
| 110.2 | (2.3) | NC |
| 115.6 | (2.0) | 1.4 |
| 131.5 | (1.5) | NC |
| 142.9 | 2.0 | (1.6) |
| 154.0 | (2.6) | NC |
| 163.7 | (2.1) | (1.3) |
| 181.9 | (2.0) | NC |
| 196.8 | (1.8) | NC |
| 210.9 | 2.4 | NC |
| 219.9 | (2.5) | NC |
| 230.2 | (2.5) | NC |
| 238.1 | 2.9 | NC |
| 245.1 | (2.2) | NC |

Numbers in parentheses represent protein peaks with a decrease in fold-change.
NC = No Change,
C = 7 days on a chow diet,
A = 7 days on an atherogenic Diet,
AC = 7days on atherogenic diet followed by an additional 14 days on a chow diet,
CC = 21 days on a chow diet.

Interestingly, three proteins, m/z 5100, m/z 35300, and m/z 197000, were not represented in HDL from C57BL/6J mice fed an atherogenic diet (either short term or long term) when compared to protein profiles obtained from mice fed a western diet (Table 8). Since cholate is the main difference between the two diets used, it is possible that these three proteins represent proteins specific to cholate metabolism and toxicity. Identification and characterization of these proteins may prove to be useful for understanding HDL inflammatory properties related to bile acid metabolism. Surprisingly, when protein profiles were prepared from pro-inflammatory HDL obtained from two other animal models of atherosclerosis (LDLR null mice on a western diet and apoE null mice on a chow diet) and compared to the common protein profile for pro-inflammatory HDL from C57BL/6J mice, only 14 out of the 21 peaks were common among the three models (Table 8 and Table 9).

Serum protein profiling offers an easier and efficient strategy for the use of biomarkers in disease diagnosis and/or drug effectiveness. We identified a number of proteins that are different in serum (Table 13) compared to the profiles obtained from HDL. A core sequence of 13 peaks from all the different mouse models of atherosclerosis/hyperlipidemia was identified (Table 10). When we compared the final sets of protein profiles obtained from serum profiling and HDL profiling, we identified a common set of eight protein peaks (Table 10). The proteins representing these eight peaks could form a very important panel of markers to not only directly assay serum samples for the identification of pro-inflammatory HDL, but also for studies to further understand the nature of pro-inflammatory HDL.

TABLE 13

SELDI peaks differentially associated with atherogenic/hyperlipidemic serum from C57BL/6J mice.

| Protein Peaks m/z (×10³) | Fold change in peaks obtained by comparing: | |
|---|---|---|
| | A to C | AA to CC |
| 5.1 | 6.4 | NC |
| 5.2 | 4.4 | (2.6) |
| 5.3 | 3.5 | (2.8) |
| 5.4 | (1.6) | NC |
| 5.8 | 1.7 | NC |
| 6.0 | 2.1 | NC |
| 6.2 | 3.7 | (3.4) |
| 6.4 | 9.1 | NC |
| 6.8 | (2.8) | NC |
| 7.2 | 2.0 | NC |
| 7.5 | 5.9 | 1.5 |
| 7.8 | 3.6 | 1.8 |
| 8.0 | 2.6 | NC |
| 8.7 | (2.3) | NC |
| 8.8 | (1.9) | NC |
| 9.0 | (2.0) | (1.7) |
| 9.3 | (2.5) | (1.8) |
| 9.5 | (2.3) | NC |
| 9.9 | 4.3 | NC |
| 10.9 | 2.4 | 2.7 |
| 11.6 | (1.9) | (1.8) |
| 12.0 | (3.0) | 1.3 |
| 12.3 | (1.7) | NC |
| 12.8 | (4.0) | (1.7) |
| 13.2 | 2.2 | 1.5 |
| 13.5 | 1.9 | NC |
| 14.0 | 1.5 | (1.4) |
| 14.4 | (4.9) | NC |
| 14.7 | 8.8 | NC |
| 14.9 | 13.2 | NC |
| 15.1 | 9.4 | NC |
| 15.3 | 18.0 | 4.6 |
| 15.6 | 16.6 | NC |
| 15.8 | 14.4 | NC |
| 16.2 | 7.7 | NC |
| 16.5 | 5.8 | NC |
| 16.9 | 3.3 | NC |
| 17.2 | 2.3 | NC |
| 18.2 | 2.3 | NC |
| 18.6 | (4.9) | (2.5) |
| 19.5 | (3.5) | NC |
| 23.6 | 1.5 | (1.9) |
| 28.0 | (1.6) | 1.6 |
| 30.0 | 1.8 | NC |
| 30.7 | 2.0 | 1.4 |
| 32.1 | 1.5 | NC |
| 33.0 | 1.3 | (1.4) |
| 34.0 | 1.2 | (1.4) |
| 38.8 | (1.5) | NC |
| 41.5 | 1.9 | NC |
| 43.2 | 1.5 | NC |
| 44.3 | (1.9) | NC |
| 45.7 | (1.7) | NC |
| 47.4 | (1.5) | NC |
| 49.6 | (2.6) | NC |
| 50.9 | (2.4) | NC |
| 51.7 | (1.9) | NC |
| 53.3 | (3.7) | NC |
| 60.4 | 1.4 | NC |
| 72.3 | (3.8) | NC |
| 75.0 | (4.0) | NC |
| 81.1 | 11.3 | NC |
| 82.4 | 2.3 | NC |
| 84.5 | (2.7) | NC |
| 85.9 | 2.4 | NC |
| 88.1 | (1.3) | NC |
| 90.0 | (1.40) | NC |
| 102.8 | (1.6) | NC |
| 107.3 | 2.3 | NC |
| 115.6 | 91.4) | NC |
| 153.9 | (1.4) | NC |
| 164.5 | 2.5 | NC |
| 181.2 | (1.6) | NC |
| 210.9 | 7.9 | NC |
| 245.1 | (1.8) | NC |

Numbers in parentheses represent protein peaks with a decrease in fold-change.
NC = No Change,
C = 7 days on a chow diet,
A = 7 days on an atherogenic Diet,
AC = 7days on atherogenic diet followed by an additional 14 days on a chow diet,
CC = 21 days on a chow diet.

TABLE 14

Common SELDI peaks differentially associated with both short-term and long-term diet-induced C57BL/6J atherogenic/hyperlipidemic serum.

| Protein Peaks m/z (10³) | Fold change in protein peaks obtained by comparing: | | |
|---|---|---|---|
| | A to C | AC to CC | W15A to W15C |
| 5.1 | 6.4 | NC | 3.8 |
| 5.2 | 4.4 | (2.6) | 2.0 |
| 7.5 | 5.9 | 1.5 | 3.6 |
| 7.8 | 3.6 | 1.8 | 2.5 |
| 9.3 | (2.5) | (1.8) | (3.8) |
| 11.6 | (1.9) | (1.8) | (2.3) |
| 12.3 | (1.7) | NC | (1.8) |
| 12.8 | (4.) | (1.7) | (1.7) |
| 14.7 | 8.8 | NC | 4.8 |
| 14.9 | 13.2 | NC | 23.9 |
| 15.3 | 18.0 | 4.6 | 14.0 |
| 15.6 | 16.6 | NC | 19.3 |
| 15.8 | 14.4 | NC | 13.6 |
| 16.2 | 7.7 | NC | 7.1 |
| 16.5 | 5.8 | NC | 4.3 |
| 18.6 | (4.9) | (2.50) | (4.4) |
| 19.5 | (3.5) | NC | (6.3) |
| 34.0 | 1.2 | (1.4) | 1.5 |
| 60.4 | 1.4 | NC | 1.7 |
| 75.0 | (4.0) | NC | (2.2) |
| 82.4 | 2.3 | NC | 5.4 |
| 84.5 | (2.7) | NC | (2.0) |
| 88.1 | (1.3) | NC | (2.4) |
| 90.0 | (1.4) | NC | (1.5) |

Numbers in parentheses represent protein peaks with a decrease in fold-change.
NC = No Change,
C = 7 days on a chow diet,
A = 7 days on an atherogenic Diet,
AC = 7 days on atherogenic diet followed by an additional 14 days on a chow diet,
CC = 21 days on a chow diet.
W15A = 15 weeks on an atherogenic diet,
W15C = 15 weeks on a chow diet The proteins that represent these m/z peaks (Table 11) that are differentially associated with pro-inflammatory HDL from C57BL/6J mouse models of hyperlipidemia and atherosclerosis. As a first screen, normal and atherogenic serum were fractionated by ion exchange columns with different pH buffers, followed by SELDI analysis to obtain the pI values of each protein peak of interest (Kozak et al. (2005) *Proteomics*, 5: 4589-4596). Using the pI and mass information of each protein peak, we searched databases (TagIdent) and obtained candidate proteins representing the SELDI peak of interest. We determined that hemoglobin was found associated with HDL in mice fed the atherogenic diets. The details of these studies are given in Example 3.

In conclusion, we have characterized eight m/z SELDI biomarker peaks in pro-inflammatory HDL and confirmed their differential expression in atherogenic/hyperlipidemic serum. Together, these markers will help determine the molecular mechanisms that participate in the conversion of normal/anti-inflammatory HDL into pro-inflammatory HDL in mice. The identification of these markers as well as markers in human pro-inflammatory HDL facilitates the development of clinical assays to improve early detection of atherosclerosis and other pathologies characterized by an inflammatory response.

Example 3

Hemoglobin Associated with High Density Lipoproteins in Sera from Mice Fed Atherogenic/Hyperlipidemic Diets In Example 2, we identified eight specific protein fingerprints using strong anion exchange SELDI ProteinChip technology that distinguish normal/anti-inflammatory HDL from pro-inflammatory HDL in mouse models of atherosclerosis. Using micro-liquid chromatography-tandem mass spectrometry, we identified the SELDI peaks representing m/z 14,900 and m/z 15,600, as mouse hemoglobin alpha chain (Hb-Alpha, 14.9 kDa) and mouse hemoglobin beta chain (Hb-beta, 15.9 kDa), respectively. Western blot analysis confirmed the differential association of Hb with pro-inflammatory HDL when compared to normal HDL. Biochemical characterization of Hb associated with HDL further showed that the Hb associated with pro-inflammatory HDL possess distinct physical and chemical properties including reduced pI (pI 4.0 & pI 7.0 vs. pI 7.5 or higher for free Hb), and association with high molecular weight complexes found in fractions containing HDL. The main form of hemoglobin found associated with HDL was oxyhemoglobin (oxyHb). Based on the pro-oxidant nature of oxyHb, our data suggest that Hb may contribute to the pro-inflammatory nature of HDL under atherogenic conditions. Moreover, we conclude that HDL-associated Hb can serve as a novel biomarker for atherosclerosis and other pathologies characterized by an inflammatory response.

Experimental Procedures

Animal Experiments.

Wild type, low density lipoprotein receptor-deficient (LDLR null) and apoE null, C57BL/6J female mice (n=8 per group) at age of 8 to 12 weeks were used in experiments comparing the three mouse models. In these experiments the mice were fed one of two diets: chow diet (Ralston Purina Mouse Chow), or atherogenic diet containing 15.8% fat, 1.25% cholesterol, and 0.5% cholic acid w/w/w, (Teklad/Harlan Catalog). For short-term studies, mice (n=8 per group) were fed the described diet for 7 days, and for long-term studies mice were fed the described diet for 15 weeks. Serum samples were isolated from overnight fasted mice, cryopreserved in 10% sucrose and kept at −70° C. until use.

Lipoprotein Isolation.

Pooled serum samples were fractionated by a system consisting of dual Pharmacia Superose 6 columns in series. Serum (0.5 ml) was eluted with sterile PBS at a flow rate of 0.5 ml/min pumped by a non-metallic Beckman HPLC pump and fractionated for every 1 ml. The first ten 1 mL fractions were discarded and each subsequent 1 mL fraction collected was analyzed for cholesterol content (Thermo, Louisville, Colo.) and BCA protein assays (Promega, Madison, Wis.) according to manufacture's protocol. VLDL, LDL, HDL and post HDL fractions were pooled for all experiments. For some experiments, HDL from individual serum sample was freshly isolated with LipiDirect HDL reagent (Polymedco, Cortland Manor, N.Y.) according to the manufacturer's protocol. The supernatant containing HDL was assayed for cholesterol content and BCA protein assays and used within 48 hours following isolation.

Sample Preparation for SELDI Analysis.

Lipoproteins or serum samples were prepared and processed on normal phase (NP-20), strong anion exchange (Q10), and weak cation exchange (CM 10) ProteinChip arrays according to the manufacturer's protocols (Ciphergen Biosystems, Fremont, Calif.). Briefly, NP-20, Q10 and CM10 array spots were equilibrated with binding buffer (1×PBS/0.1% TRITON® X-100, pH 7) for 10 mm at room temperature. Diluted samples with binding buffer (serum at 1:25, lipoprotein fractions at 1:2) were spotted onto array chips and incubated in a humidity chamber for 30 mm at room temperature. The chips were washed twice with binding buffer and once with HPLC $H_2O$, and then air-dried. The chips were sequentially treated with sinapinic acid solution, first with 0.5 μl of a 100% saturated solution followed by 1 μl of a 50% saturated solution. The sinapinic acid solution was freshly prepared by saturating EAM solution (50% acetonitrile and 0.5% trifluoroacetic acid) with sinapinic acid (3,5-dimethoxy-4-hydroxycinnamic acid).

Ciphergen Protein Chip SELDI-TOF-MS Analysis.

The arrays were analyzed with the Ciphergen ProteinChip Reader (model PB SII) as described in Example 2.

Statistical Analysis.

The data were analyzed with ProteinChip data analysis software version 3.2 (Ciphergen Biosystems, Fremont, Calif.) described in Example 2.

Identification of Proteins Representing Specific m/z Peaks.

Serum Protein Fractionation.

Serum was desalted on P-6 Micro Bio-Spin chromatography columns (Bio-Rad, Hercules Calif.) according to the manufacturer's protocol. Serum samples were fractionated using Q10 anion exchange spin columns (Ciphergen Biosystems, Fremont, Calif.), by eluting with a series of buffers decreasing in pH: pH 8.5, 7.5, 7.0, 6.0, 5.0, 4.0, and 2.0 according to the manufacturer's protocol. Protein fractions were analyzed on SELDI-TOF-MS PSII with Q10 or CM10 ProteinChip arrays. Both arrays were equilibrated with 10 mM HCl in binding buffer prior to use.

Serum Protein Purification, Passive Elution and Confirmation by SELDI-TOF-MS.

Fractions confirmed by SELDI analysis to contain a significant majority of a peak of interest were pooled and dried by centrifugal evaporation. Fractions containing the proteins were further separated on SDS-PAGE, followed by staining with Simply Blue Safe stain (Invitrogen, Carlsbad, Calif.). The bands with molecular weights corresponding to the peaks of interest were excised, gel slices were cut in half, and half of the gel slice was passively eluted as described previously (Le Bihan et al. (2004) *Proteomics*, 4:2739-2753). Briefly, the gel was dehydrated, dried in a heat block and rehydrated in organic mixture. The gel was sonicated followed by vortex. The eluted protein was used to confirm the presence of peak of interest by SELDI ProteinChip analysis. The remaining half was used for in gel digestion as described below.

Tryptic Digestion.

In-gel tryptic digestion was performed as described previously (Gomez et al. (2003) *Mol Cell Proteomics* 2:1068-1085). Briefly, eluate (following confirmation by SELDI) containing peaks of interest was reduced with DTT, alkylated with iodoacetamide and treated with trypsin (Promega). Peptides were recovered by saturating the gel slices with HPLC grade water and extracted with acetonitrile/trifloroacetic acid. Extracts were dried in a cold SAVANT Speed Vac (Global Medical Instrumentation) and subjected to µLC-MSMS as described previously (Id.). The data were used to search mouse databases using Sonar ms/ms™ (Genomic Solutions) and TurboSEQUEST™ (Thermo Electron Corp).

Electrophoresis and Immunoblots.

IEF, Tris/HCl gels and all other reagents for electrophoresis were purchased from Bio-Rad (Hercules, Calif.). Serum sample (2 µL) was loaded on 15% SDSPAGE, IEF (pH3~10), Tris/HCl Native (4~15%) or IEF-Tris/HCl 2D gels. For 2D gels, each lane from IEF gels were cut and inserted into native gels according to manufacturer's protocol (Bio-Rad). Serum samples were loaded on gels and transferred to nitrocellulose membrane (GE Healthcare, Piscataway, N.J.) according to manufacture's protocol (Bio-Rad). The membrane was immunoblotted against hemoglobin at 1:1000 (MP Biomedicals, Irvine, Calif.) or apoA-1 at 1:10,000 (Bethyl Laboratory, Montgomery, Tex.). HRP-conjugated secondary antibody (GE Healthcare) was used at 1:10000 dilution and the bands were visualized with ECL detection reagent (GE Healthcare).

Spectrophotometric Determination of Hb.

FPLC fractions containing HDL were pooled for measuring Hb using a Beckman DU 640 spectrophotometer. The spectra of all samples and pure hemoglobin species were scanned from 380 to 700 nm. Spermine NONOate (Cayman Chemical, Michigan), a slow time-release NO donor, was added to samples containing oxyhemoglobin (oxyHb) to observe the conversion of oxyHb to methemoglobin (metHb). The concentrations of oxyHb and metHb were deconvoluted by fitting a set of pure species "basis spectra" to the measured spectra by means of linear regression (Vaughn et al. (2000) *J. Biol. Chem.*, 275:2342-2348). The validity of the deconvolution method was verified when the consumption of oxyHb to the generation of metHb exhibited a one to one ratio while the total hemoglobin was conserved in all samples.

Results.

SELDI Peaks m/z 14.9 k and m/z 15.6 k are Associated with Atherogenic/Hyperlipidemic Serum and HDL.

Figure 20:
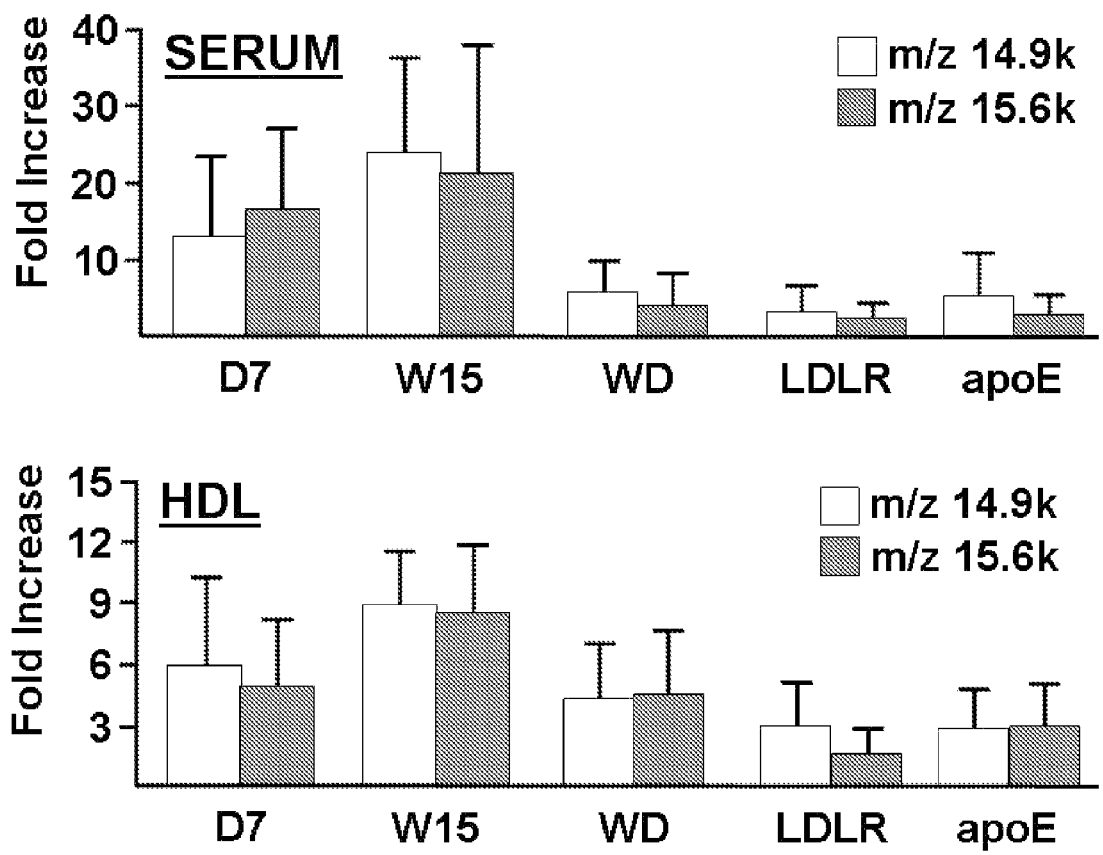
FIG. 20 shows that elevated levels of m/z 14.9 k (hemoglobin alpha chain) and m/z 15.6 k (hemoglobin beta chain) are present in four mouse models of atherosclerosis. Serum samples (n=8) from C57BL/6J mice on atherogenic diet (D7=for 7 days, W15=for 15 weeks) or western diet for 10 days (WD), or LDLR null mice on western diet for eight weeks (LDLR) or twelve week old apoE null mice on normal chow (apoE), were subjected to SELDI analysis with Q10 (pI<7) ProteinChip arrays. The two SELDI peak of interest (m/z 14.9 k and m/z 15.6 k) in atherogenic serum were compared with those of serum from the corresponding control group of mice on chow diet or in the case of apoE null mice with age matched C57BL/6J mice on chow diet, and the resulting intensities were statistically analyzed. The data presented are average fold increase in each peak. The data presented are all statistically significant with a p value of <0.05. Note that this analysis is for proteins captured on the Q10 protein-chip which brings down proteins and complexes that are both hydrophobic and which have a pI<7.0. The hemoglobin analyzed by this method represents HDL-associated hemoglobin.

SELDI analysis using strong anion exchange (Q10) ProteinChips showed that the peaks representing m/z 14.9 k and m/z 15.6 k were both elevated by a minimum of several fold compared to controls in serum (FIG. 20, top panel) and in HDL (FIG. 20, bottom panel) obtained from four different mouse models of atherosclerosis/hyperlipidemia. All the subsequent experiments for the identification and characterization of proteins representing SELDI peaks m/z 14.9 k and m/z 15.6 k were performed on serum and HDL samples obtained from C57BL/6J mice that have been subjected to the feeding of short-term (7 days) and long-term (15 weeks) atherogenic diet.

Identification of Potential Candidate Proteins SELDI Peaks m/z 14.9 and m/z 15, using size, pI and TagIdent.

Figure 21:
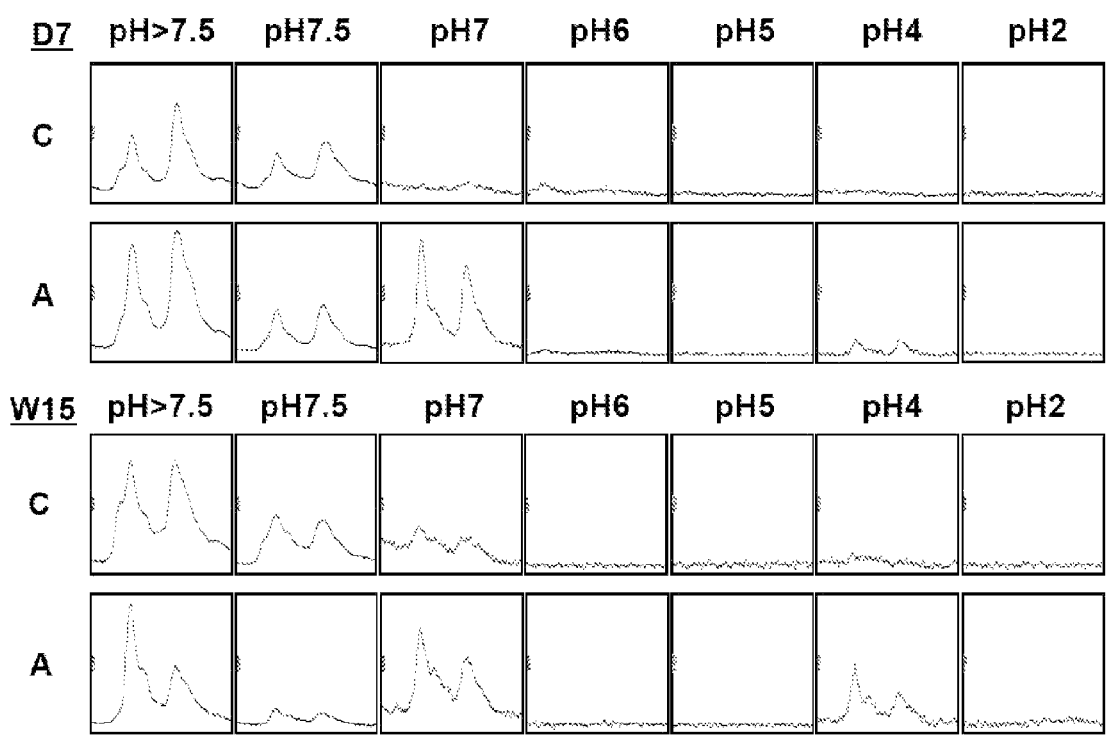
FIG. 21 illustrates determination of the pI for the peaks representing m/z 14.9 k (hemoglobin alpha chain) and m/z 15.6 k (hemoglobin beta chain). Individual serum samples from C57BL/6J mice (n=8) fed either a normal chow (C) or atherogenic diet (A) for 7 days (D7) or 15 weeks (W15) were desalted and fractionated by anion exchange spin columns with buffers at different pH as shown. The eluted fractions were subjected to SELDI analysis with cation exchange (CM 10: pI>4) or anion exchange (Q10: pI<4) ProteinChip arrays. Relative intensity at 14.9 k and at 15.6 k is shown.

To determine the identity of the proteins representing the two SELDI peaks, we first examined the pI range for the two peaks. Individual serum samples obtained from C57BL/6J mice (n=8 per group) fed a chow diet or atherogenic diet for either 7 days (short-term) or 15 weeks (long-term), were subjected to anion exchange fractionation as described under methods. The fractions were eluted with different pH buffers and further analyzed on CM10 and Q10 SELDI chips (FIG. 21). Most of the intensity representing the two peaks m/z 14.9 k and m/z 15.6 k eluted with buffers ranging from pH 7.5 and pH 8.0 (FIG. 21). An online TagIdent (protein database) search was performed using the size determined from SELDI-TOF-MS analysis and the corresponding pI as determined by anion exchange fractionation (FIG. 21). Using search criteria allowing for a 0.5% size error and +2 pI range, Hb-alpha and Hb-beta, were identified as potential candidate proteins for the 14.9 kDa and 15.6 kDa, respectively. Based on the literature the pI for free Hb ranges between 7.5-8.5. Interestingly, the two peaks representing m/z 14.9 k and m/z 15.6 k were also found associated with fractions from atherogenic serum eluted with pH 7.0 and pH 4.0 buffers (FIG. 21). These data suggested that, i) Hb in atherogenic samples has different chemical properties or ii) the proteins representing m/z 14.9 k and m/z 15.6 k are different from Hb. As indicated below, subsequent studies revealed that these peaks did in fact represent Hb and that the different physical and chemical properties of the HDL-associated Hb resulted from tight association with other HDL-associated proteins such as haptoglobin.

Fractionation and Tryptic Peptide Fragmentation and Analysis by Tandem Mass Spectrometry Confirmed the Identities of the two Biomarker Proteins as Hb-Alpha and Hb-Beta.

To further confirm the identities of the two biomarkers, the peaks corresponding to the respective sizes were partially purified from mouse serum following dealbuminization and anion exchange chromatography. The partially purified proteins were subjected to tryptic digestion followed by VLC-MSMS analysis and the resulting fragments were searched against human protein databases (Sonar and SEQUEST). The results confirmed the 14.9 kDa protein as alpha-Hb and the 15.6 kDa protein as beta-Hb.

Identification of Hemoglobin as a Potential Marker for Pro-Inflammatory HDL in the Mouse Model.

Figure 22A:
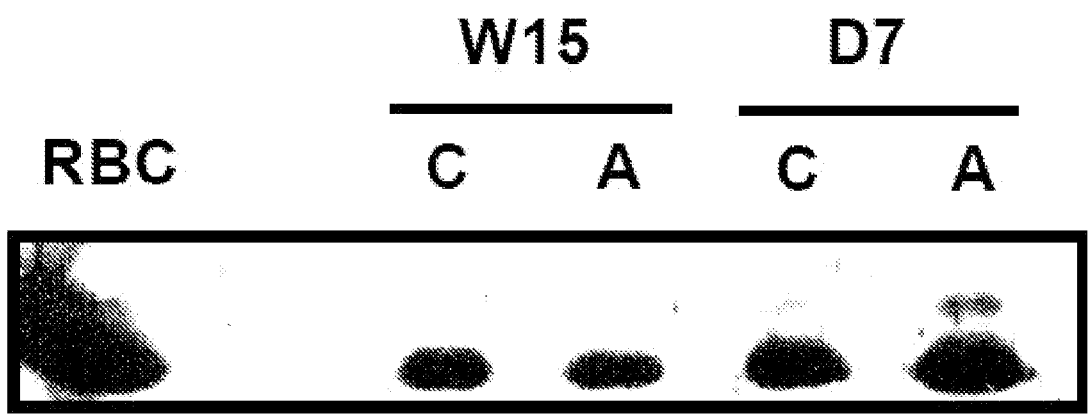
FIGS. 22A, 22B, and 22C compare non-RBC hemoglobin to RBC hemoglobin and compare the distribution of non-RBC hemoglobin among the lipoprotein and non-lipoprotein fractions of sera. Serum and lipoproteins were loaded on 15% SDS-PAGE and immunoblotted for hemoglobin. RBC lysate obtained from mice on chow diet was loaded as standard for hemoglobin.

To further validate the presence of Hb in atherogenic serum and HDL by a non-SELDI method, we first tested serum samples from mice on the atherogenic diet on SDS-PAGE followed by western blotting for Hb. The total amount of Hb in serum samples was not significantly different between normal and atherogenic serum (FIG. 22A).

It should be noted that the total concentration of Hb in serum (i.e. non-RBC Hb) is on the order of 10 micromolar. In contrast the concentration of Hb in whole blood is greater than 1 molar. Thus only about 0.001% of Hb is found in blood outside of RBC. As shown in FIG. 22A the amount of this non-RBC Hb in serum is not different in mice fed a normal chow diet compared to mice fed the atherogenic diet.

Figure 22B:
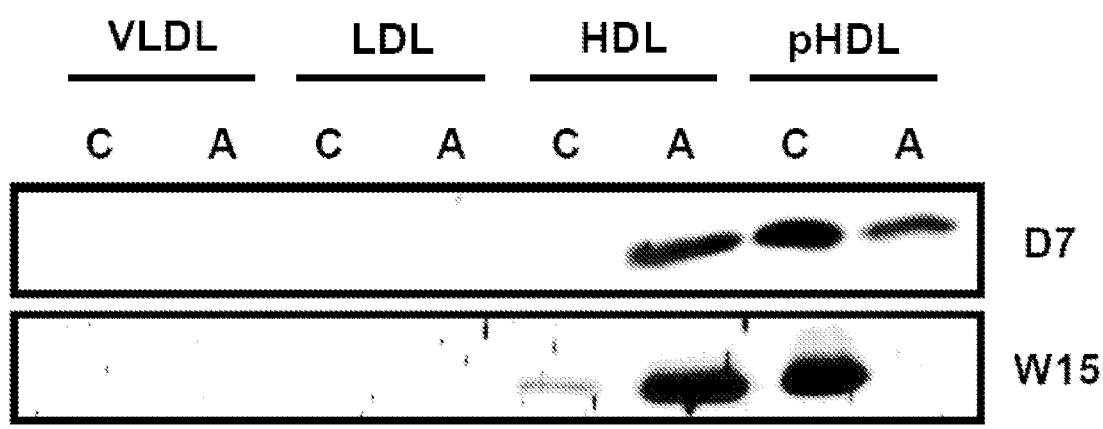
Figure 22C:
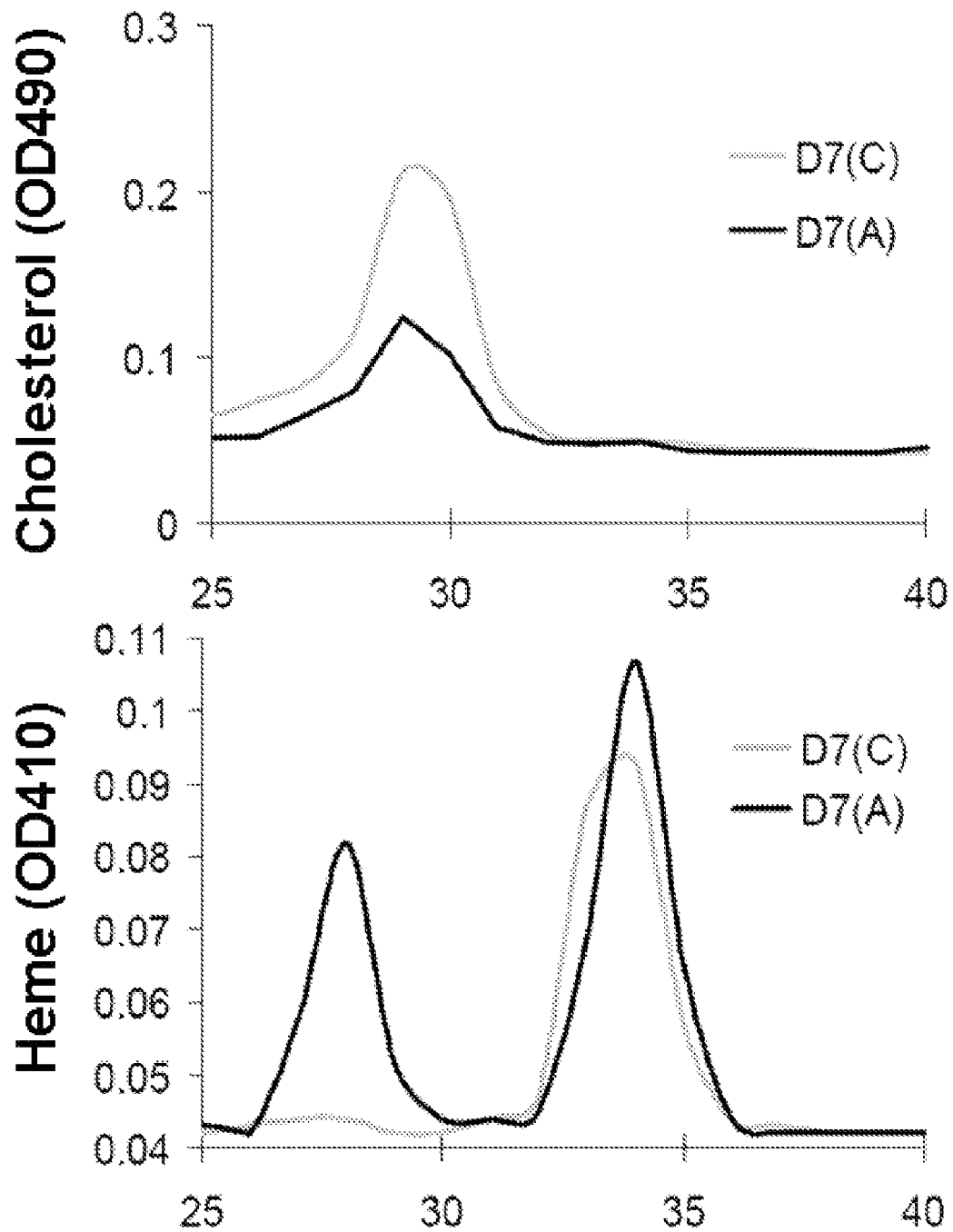

However, in FPLC fractionated lipoproteins of normal serum (i.e., serum from the mice fed the chow diet), Hb was associated with post HDL (pHDL) fractions, whereas Hb in atherogenic serum was associated with HDL fractions (FIG. 22B). Furthermore, the heme content of Hb obtained by OD measurements of individual FPLC fractions at 410 nm, confirmed the observations in FIG. 22B (FIG. 22C). In mice fed the atherogenic diet for 15 weeks, Hb was found exclusively in the HDL fractions (FIG. 22B). These experiments indicate that Hb is a marker of pro-inflammatory HDL in mice.

Hemoglobin Associated with Atherogenic Serum Exhibits Distinct Physical and Chemical Properties.

Western blot analysis of serum samples did not show significant differences in Hb mass between normal and atherogenic serum (FIG. 22A), suggesting that the association of Hb with HDL was changed upon feeding the atherogenic diet while the mass of hemoglobin remained constant. The experiments for the discovery of biomarkers associated with atherogenic serum were performed on SELDI using Q10 arrays, which select proteins with pI<7. Moreover, in the anion exchange fractionation experiments described above, significant amounts of the two peaks representing m/z 14.9 k and m/z 15.6 k were found associated with atherogenic serum fractions that eluted with pH 7.0 and pH 4.0 buffers (FIG. 21). These data suggest that, i) the mass of Hb is not significantly changed under atherogenic conditions, ii) the chemical properties of Hb are altered under atherogenic conditions as evidenced by distinct pI values (FIG. 21), and iii) as a result of changes in HDL and/or changes in Hb under atherogenic conditions Hb associates with HDL and after 15 weeks of the atherogenic diet, Hb was exclusively associated with HDL.

Figure 23A:
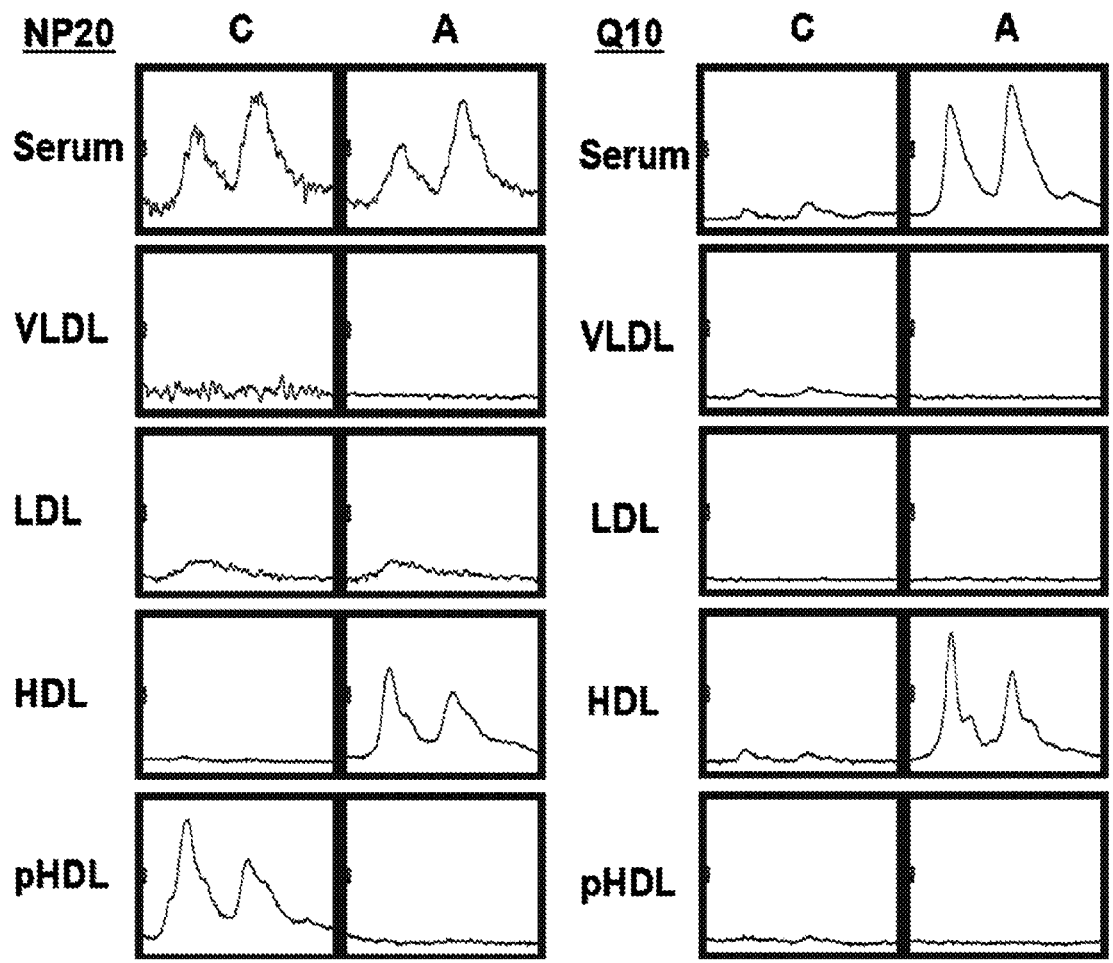
FIGS. 23A and 23B show that non-RBC hemoglobin in atherogenic serum and in HDL fractions on the atherogenic diet has distinct properties.
Figure 23B:
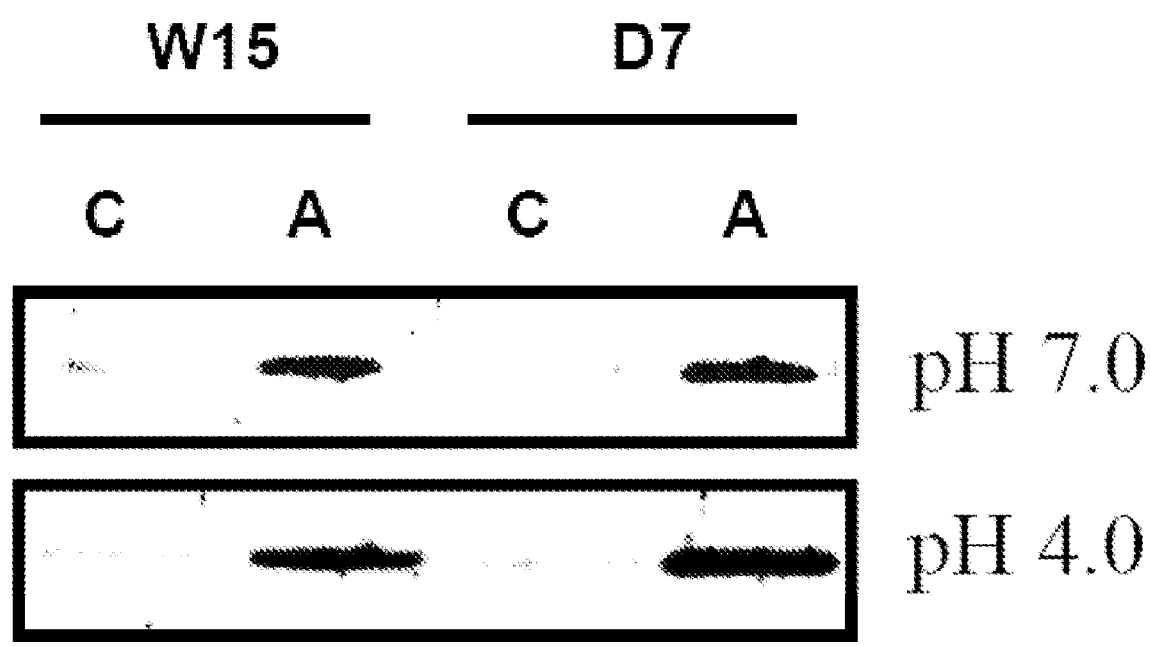

To characterize the distinct properties of Hb in atherogenic serum, SELDI analysis was performed on serum samples and FPLC lipoprotein fractions from the long-term study (W15) using NP20 and Q10 arrays. NP20 arrays, which bind all proteins, captured equal amounts of Hb from both normal and atherogenic serum samples (FIG. 23A, left panel). Furthermore, on NP-20 arrays Hb peaks were associated with pHDL fractions in non-atherogenic samples whereas entirely associated with HDL fractions in atherogenic samples (FIG. 23A, left panel). These data are in agreement with western blotting analysis following SDS-PAGE shown in FIG. 22B. On the other hand, Q10 arrays captured Hb in serum and HDL fractions obtained from only the atherogenic samples (FIG. 23A, right panel), suggesting that Hb associated in atherogenic serum has distinct properties and is associated with HDL. To further examine the occurrence of Hb with distinct pI under atherogenic conditions, SELDI-verified serum fractions of anion exchange columns from FIG. 21 were analyzed by SDS-PAGE followed by western analysis. The atherogenic serum contained Hb in the anion exchange column fractions from pH7 and pH4 (FIG. 23B).

Characterization of Hb Associated with HDL Fractions.

Figure 24:
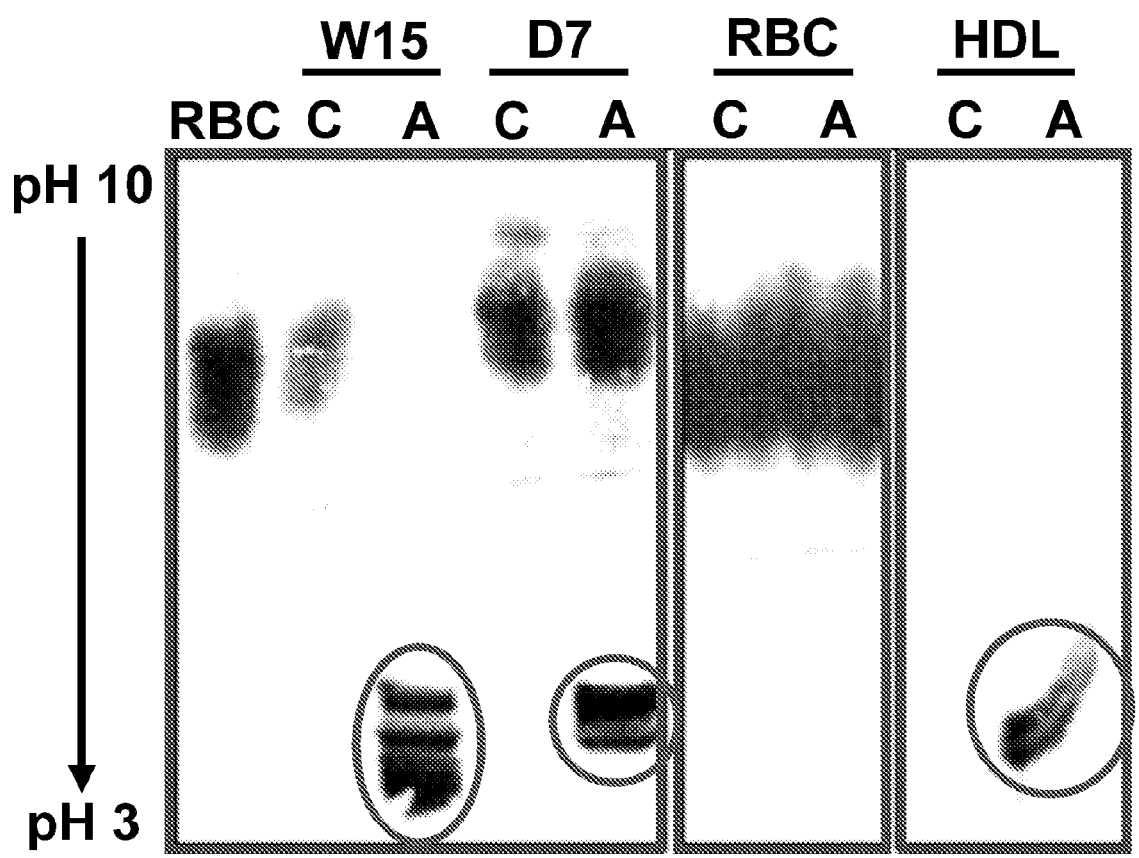
FIG. 24 shows that hemoglobin in atherogenic serum has distinct pI values. Serum samples (n=8) from C57BL/6J mice on either a normal chow (C) or atherogenic diet (A) for 7 days (D7) or 15 weeks (W15) were pooled prior to use. RBC from D7 mice were isolated by serum gradient, washed and lysed. Serum samples were fractionated by FPLC and HDL fractions from D7 mice were pooled. Pooled serum, HDL and RBC lysates were loaded on IEF gels (pH3~10) and immunoblotted for hemoglobin. RBC lysate from mice on chow (left lane) was loaded as a standard for hemoglobin. The figure indicates that the properties of the RBC hemoglobin were not different from mice on the chow or atherogenic diets. The figure also shows that there was no hemoglobin associated with HDL from the mice fed a chow diet but there was hemoglobin associated with the HDL from the mice fed the atherogenic diet and its pI was distinctly different from RBC hemoglobin.
Figure 25:
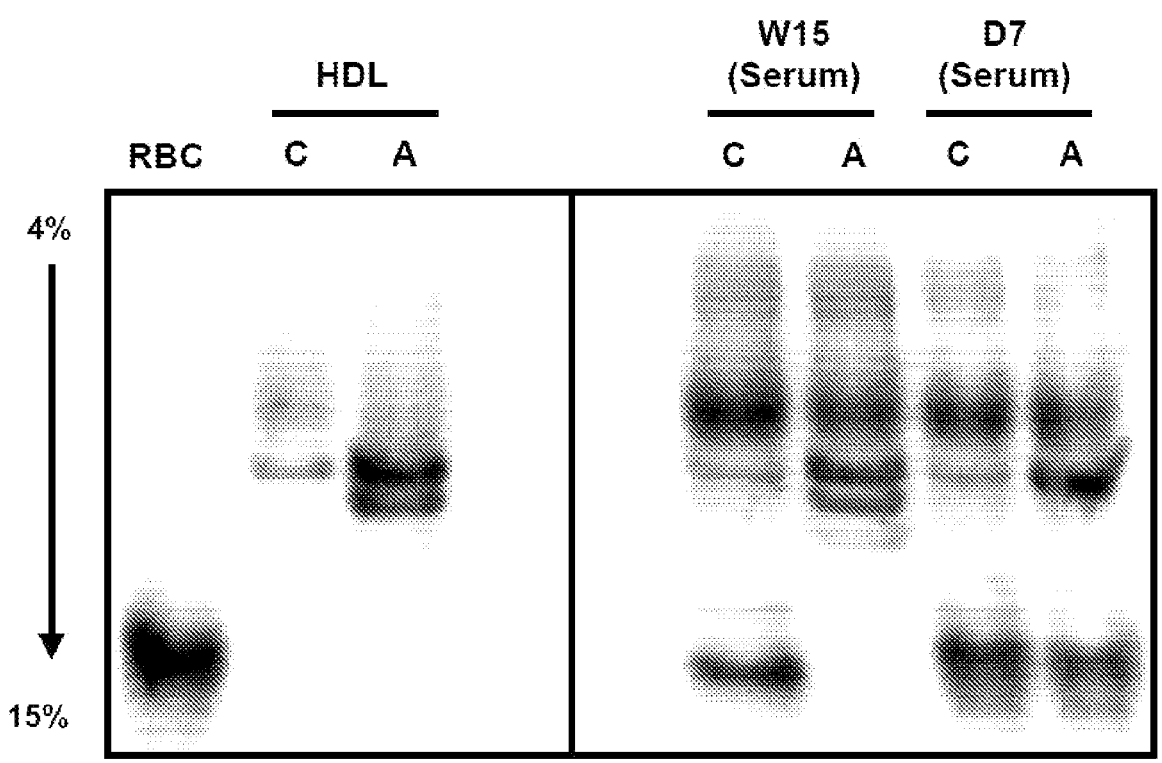
FIG. 25 shows that non-RBC hemoglobin associates with HDL fractions on the atherogenic diet (left panel) and non-RBC hemoglobin that migrates similar to RBC hemoglobin is lost after 15 weeks of feeding the atherogenic diet (right panel). Pooled serum samples from C57BL/6J mice (n=8) fed either a normal chow (C) or atherogenic diet (A) for 7 days (D7) or 15 weeks (W15) (right panel) or pooled fractions of HDL from D7 (left panel) were loaded on native-PAGE and immunoblotted for hemoglobin. RBC lysate from mice on chow was also loaded on to the gels (far left of left panel).
Figure 26A:
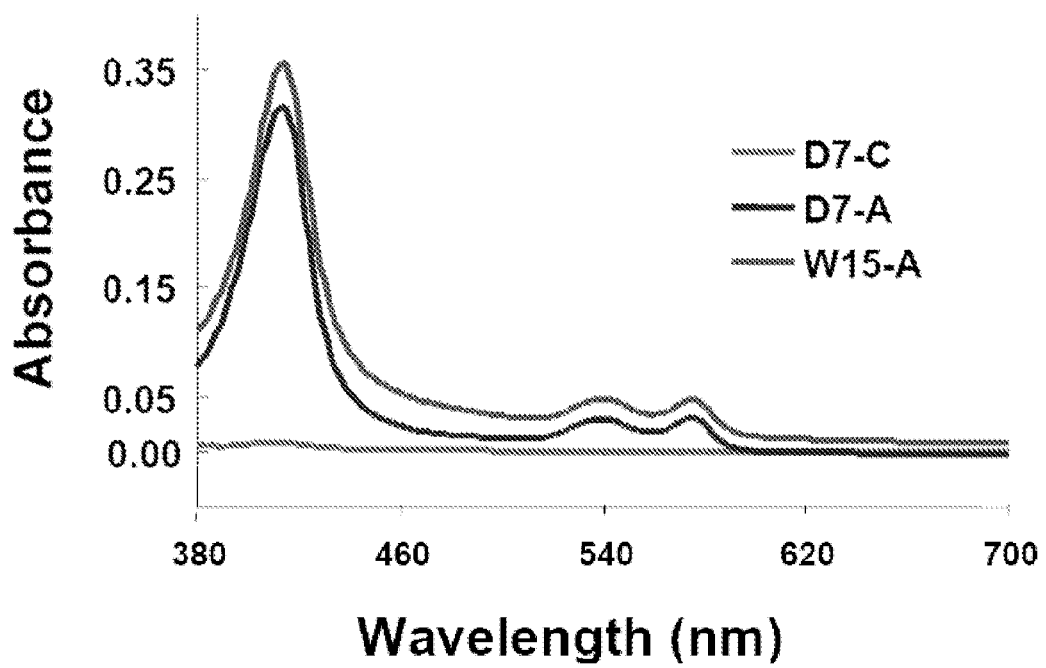
FIGS. 26A and 26B show the results of a spectrophotometric determination of Hb in HDL. Amounts and forms of Hb were determined from pooled FPLC fractions containing HDL, using a Beckman DU 640 spectrophotometer. The spectra of all samples and pure species were scanned from 380 to 700 nm (FIG. 26A). Spermine NONOate, a slow time-release NO donor, was added to samples to observe the conversion of oxyHb to metHb (FIG. 26B, representative graph). The concentrations of oxyHb and metHb were deconvoluted by fitting a set of pure species "basis spectra" to the measured spectra by means of linear regression (Vaughn et al. (2000) *J. Biol. Chem.*, 275:2342-2348).
Figure 26B:
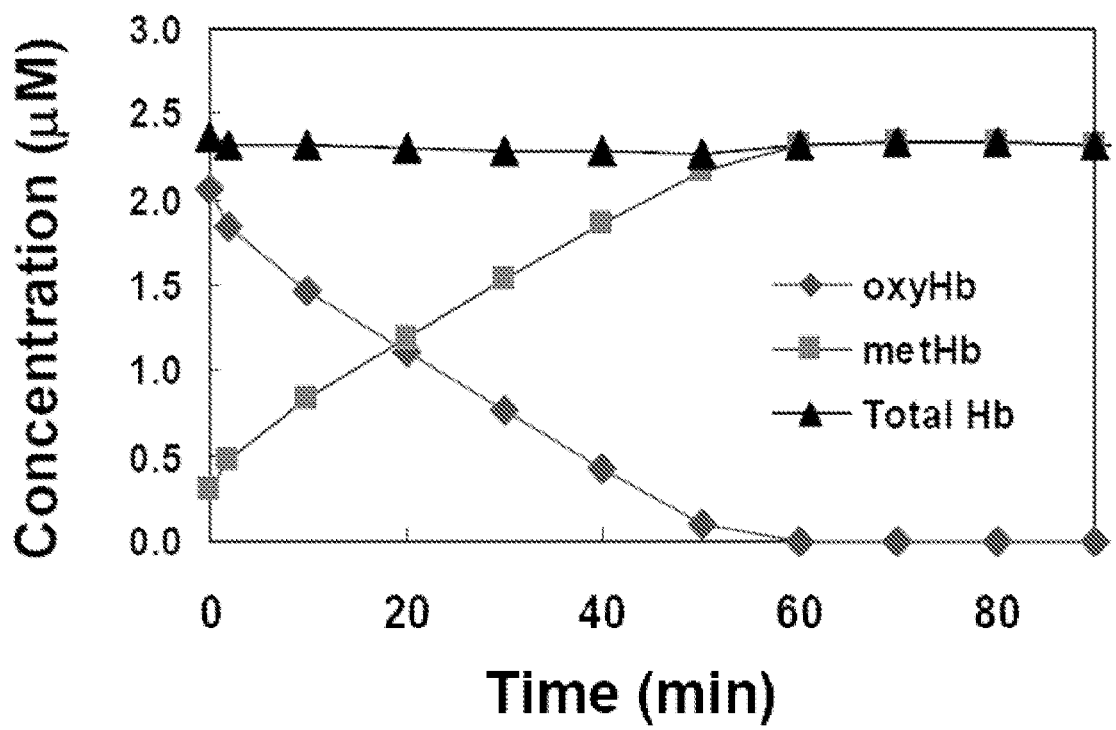

To further validate the physical and chemical properties of Hb associated with HDL, serum samples from D7 and W15 groups and HDL fractions from D7 group were subjected to iso-electric focusing (IEF) and native gel electrophoresis. IEF gels demonstrated that Hb in the atherogenic serum had a reduced pI value around 4, while normal Hb had a pI around 7.5 (FIG. 24). The transition of the normal Hb (pI 7.5) to the modified Hb (pI 4.0) was clearly seen in samples from the D7 group (FIG. 24). These changes were not due to changes in RBC since RBC isolated from the same groups of mice showed Hb with a normal pI (FIG. 24). Furthermore, Hb associated with HDL fractions from the D7 group showed the modified version of Hb (FIG. 24). Native gels showed the association of Hb immunoreactivity with high molecular weight (HMW) particles in atherogenic serum samples, which was exclusively associated with HDL after 15 weeks of feeding the atherogenic diet (FIG. 25). Furthermore, IEF/native 2D gels (FIG. 12) confirmed that Hb from atherogenic serum has multiple forms (based on pI), which associate primarily with HMW particles. To determine the specific form of Hb (oxyHb or metHb) that was associated with HDL, pooled fractions of HDL were subjected to spectrophotometric analysis. The main form of Hb associated with HDL was found to be oxyHb with a minor amount of metHb (FIG. 26 and Table 15).

TABLE 15

Concentration of oxyHb and metHb associated with HDL in D7 and W15 mice.

|  | [oxyHb] | % oxyHb | [metHb] | % metHb | Total [Hb] |
| --- | --- | --- | --- | --- | --- |
| 7D-C | 0.798 | 82% | 0.1764 | 18% | 0.9744 |
| 7D-A | 12.42 | 87% | 1.818 | 13% | 14.238 |
| W15A | 14.58 | 92% | 1.248 | 8% | 15.828 |

Discussion

Protein profiling is an efficient way to determine differentially expressed and/or associated proteins in serum samples, and allows rapid evaluation of biologically important functions. Ciphergen Biosystems (Fremont, Calif.) has developed ProteinChip technology coupled with surface-enhanced laser desorption/ionization time-of-flight mass spectrometry (SELDI-TOF-MS) to facilitate protein profiling of complex biological mixtures (Rubin and Merchant (2000) Am. Clin. Lab. 19:28-29; Weinberger et al. (2002) *Curr. Opin. Chem. Biol.* 6:86-91; Fung et al. (2001) *Curr. Opin. Biotechnol.* 12:65-69; Issaq et al. (2002) *Biochem. Biophys. Res. Commun.* 292:587-592). SELDI is unique in its ability to analyze trace (low femtomole) analytes from complex sources (serum, urine, feces, CSF, tissue culture extracts, cell lysates). A "preactivated" surface ProteinChip array also serves as an open platform for a variety of different selectivities with covalently attaching "bait" molecules (e.g. charges, hydrophobicity, specific binding affinity, antibodies) to the chip surface when the target analytes of interest are known. The efficacy of the SELDI-TOF-MS technology for the discovery of cancer protein markers in serum has recently been demonstrated (Wright et al. (1999) *Prostate Cancer Prostatic Dis.* 2:264-276; Li et al. (2002) *Clin. Chem.* 48: 1296-1304). We have successfully utilized SELDI-TOF-MS system and previously reported the identification of biomarkers for the early detection of ovarian cancer (Kozak et al. (2003) *Proc. Natl. Acad. Sci., USA,* 100:12343-12348; Kozak et al. (2005) *Proteomics*5: 45 89-96).

Database searches, following pI determination of two peaks representing m/z 14.9 k and m/z 15.6 k (FIG. 21), identified Hb-alpha and Hb-beta as potential biomarkers associated with pro-inflammatory HDL in atherogenic serum. These findings were confirmed using μLC-MSMS methods. We were initially concerned with this finding since mechanical handling and/or sample preparation can potentially result in RBC lysis and Hb release. However, subsequent careful repetitions of these experiments determined that Hb is not an artifact but rather a specific and significant marker of pro-inflammatory HDL present in atherogenic serum. First, we showed that total Hb mass is not different between serum samples obtained from chow and atherogenic diet fed mice (FIG. 22B). The total concentration of Hb in serum (i.e., non-RBC Hb) is on the order of 10 micromolar. In contrast the concentration of Hb in whole blood is greater than 1 molar. Thus only about 0.001% of Hb is found in blood outside of RBC. As shown in FIG. 22A the amount of this non-RBC Hb in serum is not different in mice fed a normal chow diet compared to mice fed the atherogenic diet.

Second, during the conversion of normal HDL into pro-inflammatory HDL (D7 chow vs. D7 atherogenic diet), we did not find any modification of Hb (mass and quality) in RBC lysates obtained from the same mice, once again suggesting that Hb association with pro-inflammatory HDL is a specific phenomenon under pro-inflammatory conditions. Third, the association of Hb with pro-inflammatory HDL is dependent on the extent of pro-inflammatory conditions as evident by comparing Hb in D7 and W15 lipoprotein samples (FIG. 22B and FIGS. 24 and 25). Finally, in four different models of atherosclerosis/hyperlipidemia including apoE null mice, which have pro-inflammatory HDL on a chow diet, Hb was found associated with HDL. Taken together, these results indicate that HDL-associated Hb is a marker of pro-inflammatory HDL.

Normal pI for Hb has been reported to be between pI 7.0 and 8.0. We found that Hb associated with pro-inflammatory HDL has at least two Hb species with distinct pI values (FIG. 21 and FIG. 24). After 15 weeks on the atherogenic diet all of the Hb associated with HDL demonstrated this abnormal pI. The changes in the pI of Hb after feeding the atherogenic diet was found not to be due to changes in hemoglobin but rather to the proteins that the hemoglobin tightly associated with in HDL. Since most of the Hb under these conditions was found to be oxyhemoglobin it is likely that the oxidative stress induced by the atherogenic diet is responsible for these changes. The absence of such changes in RBC Hb from the same mice suggests that free Hb may have been differentially affected under these conditions. The fact that total serum Hb was not different on the chow or atherogenic diets suggests that increased RBC lysis was not a factor in this process.

Haptoglobin (Hp) and Hemopexin (Hx) are plasma proteins with the highest binding affinity for hemoglobin (Hb) ($K_d$1 pM) and heme ($K_d$<1 pM), respectively. They are expressed mainly in the liver and belong to the family of acute phase proteins, whose synthesis is induced during inflammatory processes (Bowman and Kurosky (1982) *Adv Hum Genet.* 12:189-261; Altruda et al. (1985) *Nucleic Acids Res.* 13:3841-3859). It is well established that Hb (the most abundant and functionally important protein in erythrocytes), once released from red blood cells, becomes highly toxic because of the oxidative properties of heme, which participates in the Fenton reaction to produce reactive oxygen species causing cell injury (Hoffman et al. (1995) *Hematology: Basic Principle and Practice.* 2nd ed. New York, N.Y.: Churchill Livingstone). The toxicity of heme is increased by heme hydrophobicity, which enables it to intercalate into lipid membranes and other lipophylic compartments when not associated with proteins (Balla et al. (1993) *Proc. Natl. Acad. Sci., USA,* 90:9285-9289). Usually, low amounts of extravascular hemolysis occur during enucleation of erythroblasts and destruction of senescent erythrocytes, thus causing Hb release into plasma. Under intravascular hemolysis-linked pathologic conditions, such as hemorrhage, hemoglobinopathies, ischemia reperfusion, or malaria, large amounts of free Hb are released (Wagener et al. (2001) *Trends Pharmacol Sci.* 22:52-54). Once in the plasma, free Hb rapidly dissociates in dimers that are bound by Hp. Metabolism of plasma Hb is considered a main function of tissue macrophages, which can take up Hb-Hp complexes through the macrophage scavenger receptor CD1 63 (Schaer et al. (2006) *Blood* 107:373-380; Fabriek et al. (2005) *Immunobiology* 210:153-160) and internalize them (Kristiansen et al. (2001) *Nature* 409:198-201). Interestingly, a very recent study identified low-density lipoprotein receptor-related protein (LRP)/CD9 1 (Hvidberg et al. (2005) *Blood* 106:2572-2579) as the receptor responsible for scavenging hemopexin-heme complexes. LRP/CD9 1 is expressed in several cell types including macrophages, and hepatocytes, which can internalize the heme-Hx complex through receptor-mediated endocytosis (Hunt et al. (1996) *J Cell Physiol.* 168: 71-80). In the experiments reported here, we did not see a release of Hb from RBC but rather a conversion of existing Hb into a form (not reported previously) that associates with HDL fractions. It is possible that under oxidative stress conditions, Hb-Hp-Hx complexes are formed and associated with HDL for rapid clearance from the circulation. Indeed, Hp has been reported to associate with apoA1, the major protein component of HDL (Rademacher et al. (1987) *Anal Biochem.* 160:119-126; Kunitake et al. (1994) *Biochemistry* 33:1988-1993; Porta et al. (1999) *Zygote* 7:67-77; Spagnuolo et al. (2005) *J. Biol. Chem.* 280:1193-1198). Hp association of apoA1 alters HDL function (Balestrieri et al. (2001) *Mol Reprod Dev.* 59:186-191; Cigliano et al. (2001) *Steroids* 66:889-896). The data in FIGS. 12-15 suggest that non-RBC hemoglobin, haptoglobin, and hemopexin are all in the same complex in HDL under atherogenic conditions.

Hb is a known marker for injuries and diseases associated with glycemia, oxidative stress, hypertension, insulin resistance, obesity, and diabetes (Zhang et al. (2004) *Proteomics* 4: 244-256; de Valk and Marx (1999) *Arch Intern Med.* 159: 1542-1548; Alayash et al. (2001) *Antioxid Redox Signal* 3:313-327). Hb is also considered to be toxic since free Hb is also a potential oxidant due to its heme (Fe) and heme-bound reactive radicals (Alayash (1999) *Nat Biotechnol.* 17:545-549), which have also been shown to oxidize LDL in vivo (Paganga et al. (1992) *FEBS Lett.* 303:154-158; Miller et al. (1996) *Arch Biochem Biophys.* 326:252-260; Ziouzenkova et al. (1999) *J. Biol. Chem.* 274: 18916-18924). Our findings show for the first time that in an oxidative stress environment Hb associates with HDL fractions in mice. Pro-inflammatory HDL in atherogenic serum contains lipid hydroperoxides (LOOH), lacks paraoxonase activity, activates monocytes, fails to prevent the oxidation of LDL and exhibits less cholesterol efflux. Here we report that Hb specifically associates with pro-inflammatory HDL in atherogenic mice. Without being bound to a particular theory we believe that Hb association with HDL is involved in the conversion of HDL from anti-inflammatory to pro-inflammatory.

In conclusion, Hb associates with pro-inflammatory HDL in animal models of atherosclerosis. By extension to humans, we believe HDL-associated Hb, can serve as a marker of pro-inflammatory HDL.

Example 4

Protocol for LDL Aggregation Assay Using Qiagen Albumin Depletion Columns

Materials.

Typical materials for an LDL aggregation assay using an albumin depletion column are shown in Table 16.

TABLE 16

Materials for LDL aggregation assay.

| | Materials | Vendor/Source | Catalog Number |
|---|---|---|---|
| 1 | Qproteome Albumin/IgG Depletion Columns | Qiagen | 37521 |
| 2 | LDL | Ultracentrifuge | N/A |
| 3 | 50 mM Tris, 150 mM NaCl, 2 mM CaCl2 buffer | N/A | |
| 4 | 96 well plates | Costar | 3596 |
| 5 | Phospholipase C from *Bacillus cereus* (PLC) | Sigma | P6621 |

Methods:

Preparation of the Samples.

1. Dilute 25 μL of serum or plasma with 75 μL dilution buffer.

2. Centrifuge an albumin/IgG depletion spin column briefly at 500× g to remove resin from the screw cap.

3. Remove the screw cap, break off the bottom closure of the spin column, and drain the storage buffer by gravity flow.

4. Equilibrate the spin column by pipetting 2×0.5 mL aliquots of dilution buffer onto the spin column and letting each run out by gravity flow.

5. Close the spin column with the caps for QIAfilter Cartridges.

6. Apply the sample prepared in step 1 onto the column.

7. Close the lid of the spin column and shake vigorously to obtain a homogenous suspension. Incubate for 5 min on a shaker at room temp.

8. Remove the QIAfilter Cartridge and transfer the spin column to a clean centrifuge tube.

9. Loosen the cap of the column a quarter turn.

10. Collect the flow-through by centrifugation at 500× g for 10 s.

11. Wash the column with 2×100 μL aliquots of dilution buffer, collecting each wash fraction by centrifugation at 500× g for 10 s.

12. Combine the flow-through fraction from step 10 and the two wash fractions from step 11.

Removal of Apo B Containing Proteins and Cholesterol Determination

1. ApoB containing proteins are removed from the albumin depleted sample by dextran sulfate precipitation. For precipitation with dextran sulfate, Sigma HDL cholesterol reagent containing dextran sulfate and magnesium ions was dissolved in distilled water. Fifty microliters of dextran sulfate (1.0 mg/ml) was mixed with 500 uL of each sample and incubated at room temperature for 5 min and subsequently centrifuged at 3,000 g for 10 min. The supernatant containing HDL was used in the experiments.

2. Total cholesterol is measured in the albumin/apoB depleted HDL supernatant using a standard cholesterol assay.

3. HDL supernatant is added at a concentration of 10 μg to each well.

Preparation of Phospholipase C (PLC)

1. To a vial of PLC (250 units/vial), add enough ddH$_2$O to make 56.3 units/mL. e.g., add 4.4 mL ddH$_2$O to a vial containing 250 units.

2. Vortex briefly.

3. Aliquot 200 μL of PLC solution into eppendorf tubes. Freeze @ −20° C.

Incubation of LDL+Samples

1. Make additions to wells accordingly (run all controls, samples, etc in triplicate:

TABLE 17

Components of wells.

| Samples | Buffer (μL) | LDL (μL) | Sample |
|---|---|---|---|
| LDL alone | 190 | 10 | |
| LDL + PLC | 170 | 10 | |
| LDL + PLC + sample | 130 | 10 | 40 |

Note:
Each well should have 75 μg LDL (e.g. if concentration of LDL is 8.6 mg/mL, add 8.7 μL). Values may change depending upon concentrations of LDL and sample.

2. Incubate plate for 1 hour at 37° C. on nutator.

3. Read plate on plate reader at a wavelength of 478 nm.

Incubation with PLC

1. Each well except for "LDL alone" receives 20 μL of PLC solution.

2. Add 200 μL of buffer to the 200 μL of PLC solution.

3. Vortex briefly.

4. Add 20 μL of the diluted PLC solution to each well as indicated.

5. Read plate at 478 nm @ 0 min, 5 min, 10 min, 30 min, 45 min, and 60 min.

Example 5

D-4F Treatment Decreases the Association of Hemoglobin and its Scavengers with High Density Lipoprotein in Mice Objective.

We have previously reported that an apolipoprotein A-I (apoA-I) mimetic, D-4F, converted HDL from pro-inflammatory to anti-inflammatory in mice and monkeys. Having discovered that hemoglobin (Hb) associates with HDL in animal models of atherosclerosis and contributes to the pro-inflammatory nature of HDL under atherogenic conditions, we sought to determine whether D-4F treatment can decrease the association of Hb with pro-inflammatory HDL in an animal model of atherosclerosis.

Methods and Results.

Figure 2:
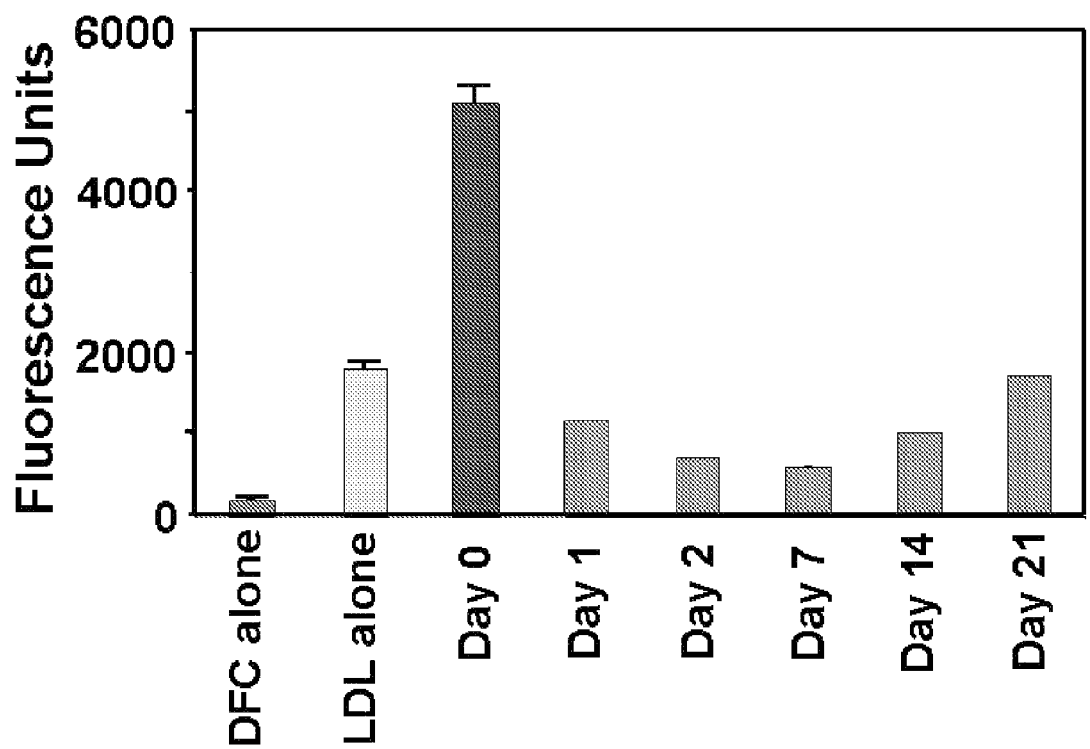
FIG. 2 shows that ApoE null mouse HDL is pro-inflammatory on a chow diet and is converted to anti-inflammatory after treatment with oral D-4F. Nine-month-old female apoE null mice on a chow diet (n=4 mice per group) were bled prior to treatment (Day 0) and after treatment with the apolipoprotein A-I mimetic peptide D-4F (50 µg/mL drinking water) for the number of days shown on the X-axis. The ability of the apoE null mouse HDL to inhibit the fluorescence of LDL plus DCF was determined as a measure of its inflammatory properties. The data show that apoE null mouse HDL was pro-inflammatory prior to treatment ((i.e. addition of the Day 0 apoE null HDL increased the fluorescence above that induced by LDL alone), but became anti-inflammatory after treatment with D-4F (Days 1-21).
Figure 3:
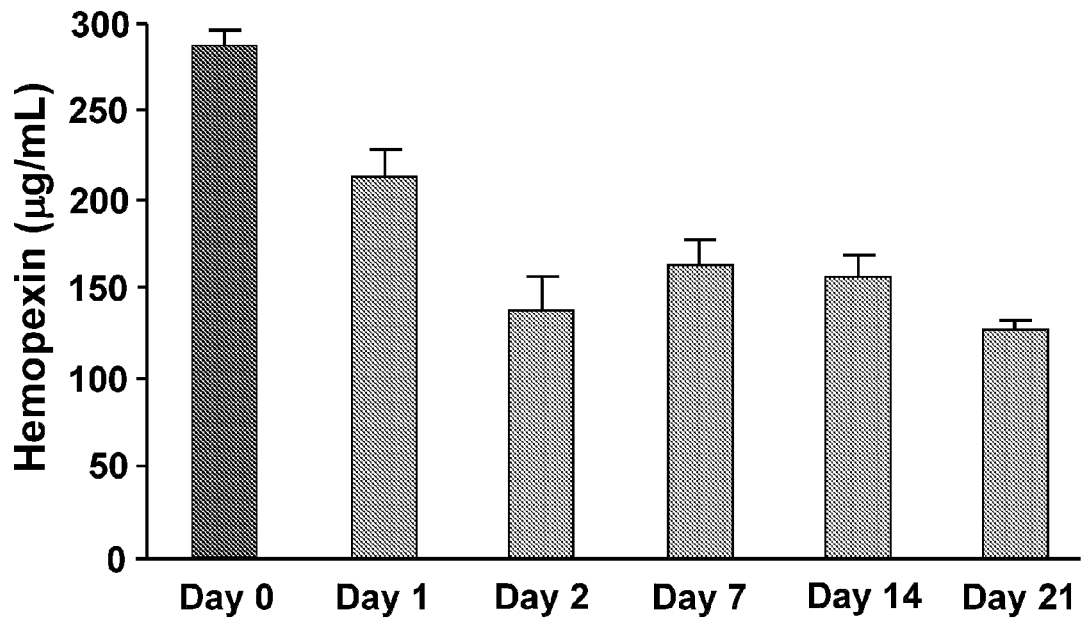
FIG. 3 shows that serum concentrations of hemopexin decrease after D-4F treatment. Serum concentrations of hemopexin in the mice described in FIG. 2 above were determined by ELISA.
Figure 4:
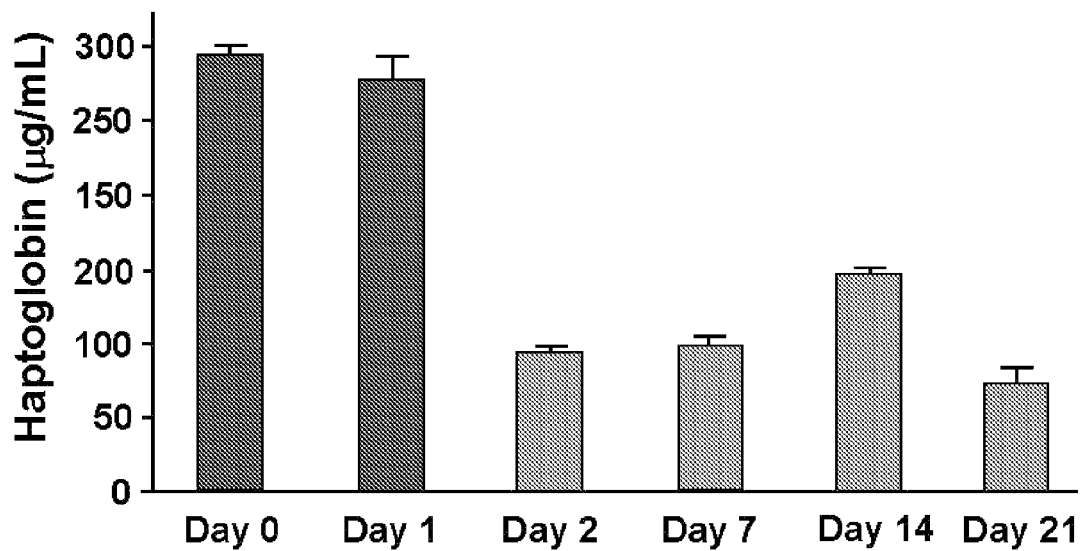
FIG. 4 shows that serum concentrations of haptoglobin decrease after D-4F treatment. The serum concentrations of haptoglobin in the mice described in FIG. 2 above were determined by ELISA.

The data in FIG. 2 indicate that HDL taken from apoE null mice (a mouse model of atherosclerosis) is pro-inflammatory. After administration of an oral apoA-I mimetic peptide (D-4F) the HDL was converted to anti-inflammatory. As shown in FIGS. 3 and 4, concomitant with the change in the inflammatory properties of HDL, there was a decrease in the concentrations of hemopexin and haptoglobin in the sera of the mice.

Figure 29:
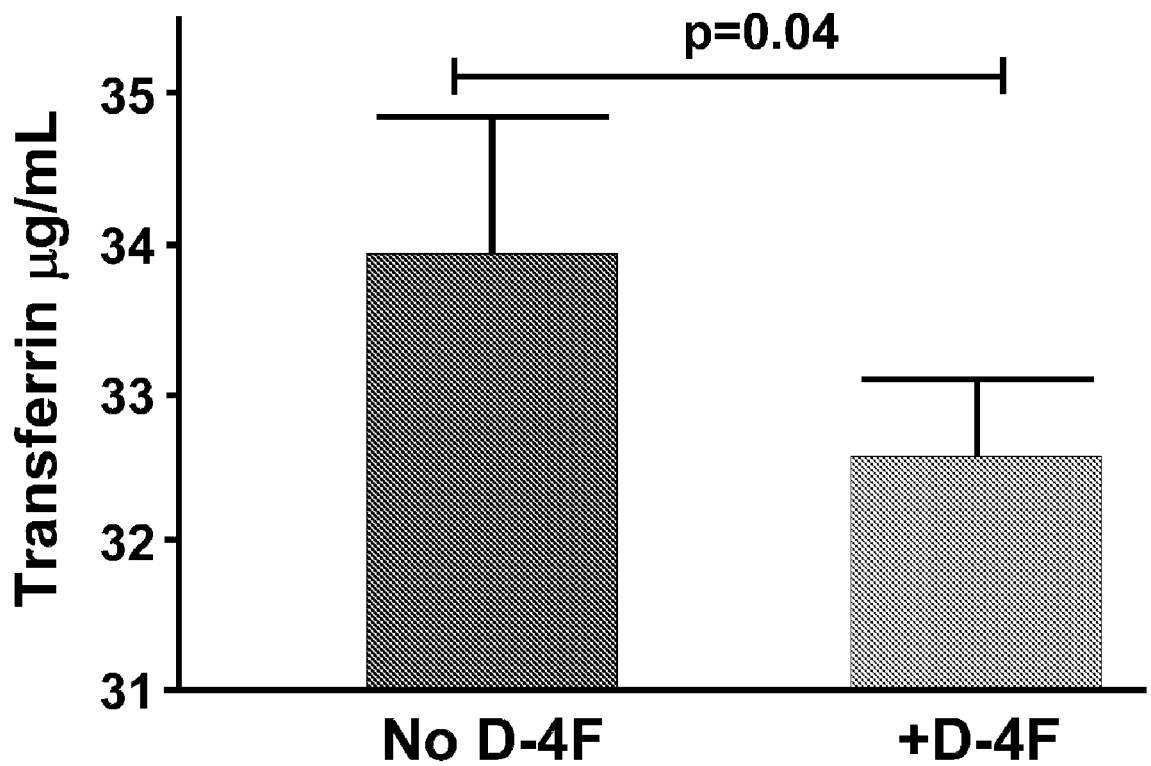
FIG. 29 demonstrates that adding D-4F to the drinking water (+D-4F) of 4 month old apoE null mice (n=8 per group) for 2 months resulted in a significant decrease in the content of transferrin in HDL-supernatants from the mice compared to mice that received drinking water without D-4F (No D-4F).
Figure 30:
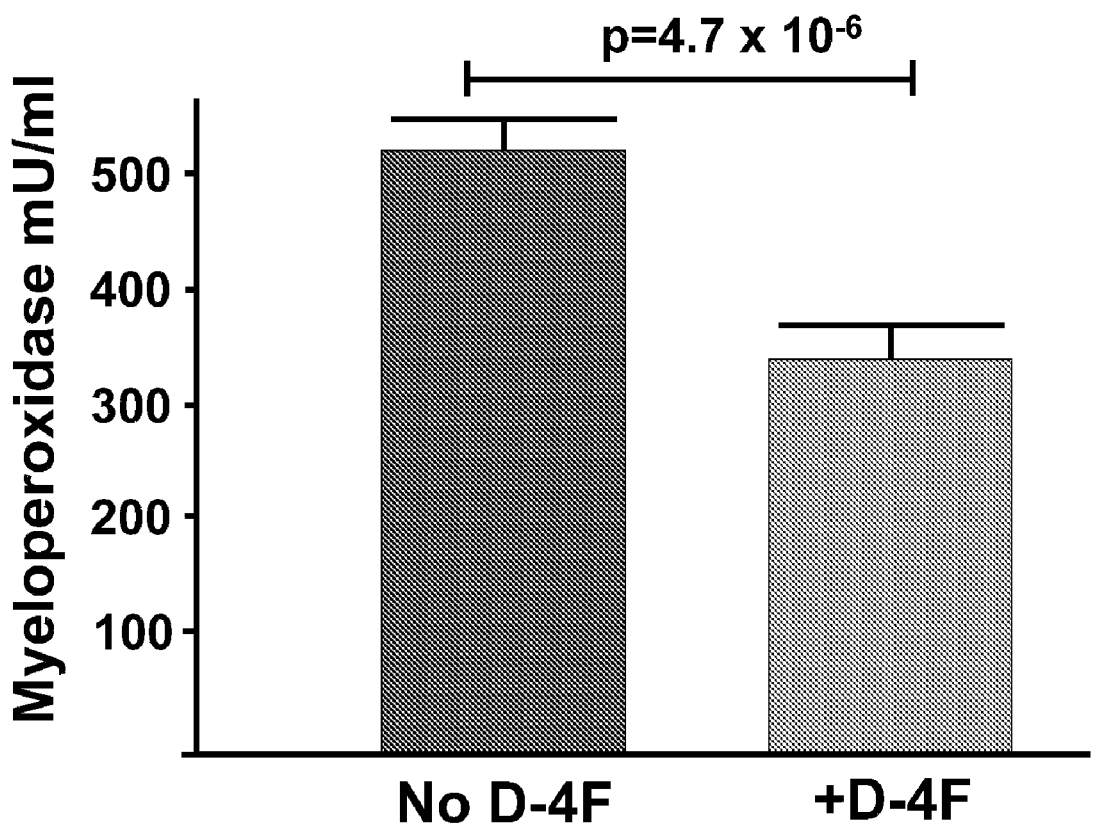
FIG. 30 demonstrates that adding D-4F to the drinking water (+D-4F) of 4 month old apoE null mice (n=8 per group) for 2 months resulted in a very significant decrease in the content of myeloperoxidase in HDL-supernatants from the mice compared to mice that received drinking water without D-4F (No D-4F).

Analysis of the HDL from the mice indicated that paralleling the conversion of the pro-inflammatory HDL to anti-inflammatory there was also a decrease in the content of haptoglobin and hemopexin in the mouse HDL without a change in the content of apoA-I in the HDL (FIG. 5). Paralleling the decreased levels of serum and HDL hemopexin and haptoglobin there was an increase in the concentration of non-RBC hemoglobin that migrated with properties similar to that of normal RBC hemoglobin (FIG. 6) and there was a decrease in the hemoglobin content of HDL (FIG. 7 far right bar graphs). As shown in FIGS. 29 and 30, administration of D-4F also significantly reduced the content of transferrin and myleoperoxidase in HDL-supernatants.

CONCLUSION

Hb and its scavenger proteins hemopexin and haptoglobin are components of pro-inflammatory HDL. One of the mechanisms by which D-4F converts pro-inflammatory HDL to anti-inflammatory HDL may be by preventing and/or reversing the association of pro-oxidant Hb containing proteins with HDL. Treatment with an agent that converts pro-inflammatory HDL to anti-inflammatory HDL was clearly paralleled by changes in HDL-associated hemoglobin, haptoglobin hemopexin, transferrin, and myeloperoxidase. These results indicate that the assays described herein will be useful in monitoring therapies that improve dysfunctional HDL and reduce atherosclerosis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting or quantifying pro-inflammatory HDL in a mammal, said method comprising:
   measuring the level of heme-containing and/or heme-binding protein(s) associated with HDL from said mammal, where said heme-containing and/or heme-binding proteins are selected from the group consisting of hemoglobin, haptoglobin, hemopexin, transferrin, soluble CD163, and myeloperoxidase; and
   scoring said measurement as a positive indicator of pro-inflammatory HDL where there is an elevated level of heme-containing and/or heme-binding protein(s) as compared to the level of heme-containing and/or heme-binding protein found in normal anti-inflammatory HDL.

2. The method of claim 1, wherein said method comprises measuring the amount of hemoglobin associated with HDL and measuring the amount of haptoglobin associated with HDL.

3. The method of claim 2, wherein said method comprises calculating the product of hemoglobin and haptoglobin associated with HDL.

4. The method of claim 1, further comprising measuring the level of the same heme-containing and/or heme-binding proteins in the non-lipoprotein fraction of plasma where an increased ratio of heme-containing and/or heme-binding protein in HDL to heme-containing and/or heme-binding protein in the non-lipoprotein fraction of plasma as compared to the ratio found in subjects having normal anti-inflammatory HDL indicates that the HDL from said mammal is pro-inflammatory HDL.

5. The method of claim 1, wherein said measuring comprises an immunoassay.

6. The method of claim 1, wherein said measuring comprises an ELISA.

7. A method of detecting or quantifying pro-inflammatory HDL in a mammal, said method comprising:
   determining the level of heme associated with HDL from said mammal, where an elevated level of heme associated with HDL as compared to the level of heme associated with protective HDL indicates that said HDL is pro-inflammatory HDL.

8. The method of claim 7, where the elevated level is statistically significant at a confidence level equal to or greater than 90%.

* * * * *